(12) United States Patent
Oswald et al.

(10) Patent No.: US 12,011,466 B2
(45) Date of Patent: Jun. 18, 2024

(54) **MODIFIED *ESCHERICHIA COLI* STRAIN NISSLE AND TREATMENT OF GASTROINTESTINAL DISORDER**

(71) Applicants: INSERM (INSTITUT NATIONAL DE LA SANTÉ ET DE LA RECHERCHE MÉDICALE), Paris (FR); UNIVERSITÉ TOULOUSE III—PAUL SABATIER, Toulouse (FR); ECOLE NATIONALE VÉTÉRINAIRE DE TOULOUSE, Toulouse (FR); INSTITUT NATIONAL DE RECHERCHE POUR L'AGRICULTURE, L'ALIMENTATION ET L'ENVIRONNEMENT (INRAE), Paris (FR); CENTRE HOSPITALIER UNIVERSITAIRE DE TOULOUSE, Toulouse (FR)

(72) Inventors: Eric Oswald, Toulouse (FR); Jean-Philippe Nougayrede, Toulouse (FR); Clémence Massip, Toulouse (FR); Patricia Martin, Toulouse (FR); Priscilla Branchu, Toulouse (FR)

(73) Assignees: INSERM (INSTITUT NATIONAL DE LA SANTÉ ET DE LA RECHERCHE MÉDICALE), Paris (FR); UNIVERSITÉ PAUL SABATIER TOULOUSE III, Toulouse (FR); ECOLE NATIONALE VÉTÉRINAIRE DE TOULOUSE, Toulouse (FR); INSTITUT NATIONAL DE RECHERCHE POUR L'AGRICULTURE, L'ALIMENTATION ET L'ENVIRONNEMENT, Paris (FR); CENTRE HOSPITALIER UNIVERSITAIRE DE TOULOUSE, Toulouse (FR)

( * ) Notice: Subject to any disclaimer, the term of this patent is extended or adjusted under 35 U.S.C. 154(b) by 74 days.

(21) Appl. No.: 17/625,220

(22) PCT Filed: Jul. 7, 2020

(86) PCT No.: PCT/EP2020/069124
§ 371 (c)(1),
(2) Date: Jan. 6, 2022

(87) PCT Pub. No.: WO2021/005059
PCT Pub. Date: Jan. 14, 2021

(65) Prior Publication Data
US 2022/0265731 A1 Aug. 25, 2022

(30) Foreign Application Priority Data
Jul. 8, 2019 (EP) .................... 19184867

(51) Int. Cl.
*A61K 35/741* (2015.01)
*A61P 1/00* (2006.01)
(Continued)

(52) U.S. Cl.
CPC .............. *A61K 35/741* (2013.01); *A61P 1/00* (2018.01); *C12N 1/205* (2021.05); *C12N 9/485* (2013.01); *C12R 2001/19* (2021.05)

(58) Field of Classification Search
CPC .......... C12N 1/205; C12N 1/20; C12N 9/485; A61K 35/741
See application file for complete search history.

(56) References Cited

PUBLICATIONS

Massip et al. "Deciphering the interplay between the genotoxic and probiotic activities of *Escherichia coli* Nissle 1917" Deciphering the interplay between the genotoxic and probiotic activities of *Escherichia coli* Nissle 1917. PLoS Pathog 15(9): e1008029. (Year: 2019).*
Blain—2013 "In Vivo Evidence for a Prodrug Activation Mechanism during Colibactin Maturation" ChemBioChem 2013, 14, 1194-1197 (Year: 2013).*
Olier et al. "Genotoxicity of *Escherichia coli* Nissle 1917 strain cannot be dissociated from its probiotic activity" Gut Microbes 3:6, 501-509; Nov./Dec. 2012; (Year: 2012).*
Xiaoying Bian et al, "Two more pieces of the colibactin genotoxin puzzle from *Escherichia coli* show incorporation of an unusual 1-aminocyclopropanecarboxylic acid moiety", Chemical Science, vol. 6, No. 5, Jan. 1, 2015 (Jan. 1, 2015), p. 3154-3160.
(Continued)

*Primary Examiner* — Thane Underdahl
(74) *Attorney, Agent, or Firm* — WC&F IP

(57) ABSTRACT

The invention relates to the field of modified *Escherichia coli* strain Nissle 1917 (EcN) and its use for treating gastro-intestinal disorders. The invention is based on the study of the mechanisms implicated in the probiotic properties of the *Escherichia coli* strain Nissle 1917 (EcN). This study has allowed the inventors to decouple the probiotic activity of EcN from its genotoxic activity by demonstrating that EcN ClbP protein, the enzyme that activates the genotoxin colibactin, is also required for the siderophore-microcins activity of probiotic EcN, but interestingly, not its enzymatic domain that cleaves precolibactin to form active colibactin. Furthermore, inventors demonstrate in an in vivo animal model infected by a bacterial pathogen that administration of an EcN modified strain with clbP gene encoding ClbP protein inactive for the peptidase domain, is non-genotoxic (do not produce colibactin) but keeps the bacterial antagonist activity, and reduces colonization and virulence of the pathogen by maintaining the siderophore-microcin production. Thus this study opens the way to safe use of EcN and accordingly the present invention provides an *Escherichia coli* strain Nissle 1917 (EcN) bacterium carrying a gene encoding ClbP protein which is inactive for the peptidase domain, and its use as a drug and more particularly for use in the treatment of gastro-intestinal disease.

Figure 1A:
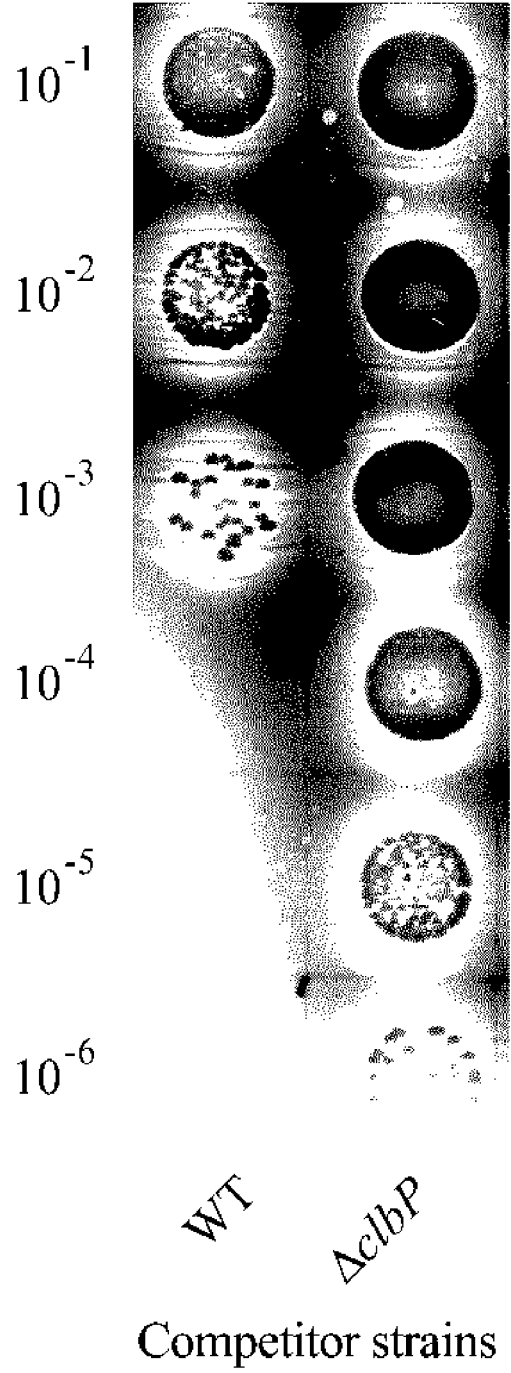

17 Claims, 14 Drawing Sheets
Specification includes a Sequence Listing.

(51) Int. Cl.
*C12N 1/20* (2006.01)
*C12N 9/48* (2006.01)
*C12R 1/19* (2006.01)

(56) References Cited

PUBLICATIONS

Emily P. Balskus, "Colibactin: understanding an elusive gut bacterial genotoxin", Natural Product Reports, vol. 32, No. 11, Jan. 1, 2015 (Jan. 1, 2015), p. 1534-1540.
D. Dubois et al, "ClbP Is a Prototype of a Peptidase Subgroup Involved in Biosynthesis of Nonribosomal Peptides", Journal of Biological Chemistry, vol. 286, No. 41, Oct. 14, 2011 (Oct. 14, 2011), p. 35562-35570.
Carolyn A. Brotherton et al, "A Prodrug Resistance Mechanism Is Involved in Colibactin Biosynthesis and Cytotoxicity", Journal of the American Chemical Society, vol. 135, No. 9, Feb. 20, 2013 (Feb. 20, 2013), p. 3359-3362.
Nougayrède Jean-Philippe et al, "*Escherichia coli* induces DNA double-strand breaks in eukaryotic cells", Science, American Association for the Advancement of Science, vol. 313, No. 5788, Aug. 11, 2006 (Aug. 11, 2006), p. 848-851.
Clémence Massip et al, "Deciphering the interplay between the genotoxic and probiotic activities of *Escherichia coli* Nissle 1917", PLOS Pathogens, vol. 15, No. 9, Sep. 23, 2019 (Sep. 23, 2019), p. e1008029.

\* cited by examiner

A

MODIFIED ESCHERICHIA COLI STRAIN NISSLE AND TREATMENT OF GASTROINTESTINAL DISORDER

FIELD OF THE INVENTION

The invention generally relates to the field of modified *Escherichia coli* strain Nissle 1917 (EcN) and its use for treating gastro-intestinal disorders.

BACKGROUND OF THE INVENTION

The probiotic *Escherichia coli* strain Nissle 1917 (EcN) was isolated during World War I by Alfred Nissle in a soldier who resisted a severe diarrhea outbreak (1,2). EcN was initially studied for its ability to fight bacterial gastrointestinal infections. It was demonstrated to impede intestinal colonization by *Salmonella enterica* serovar *Typhimurium* (*S. Typhimurium*) (3,4) and to exhibit an antibacterial activity against enterohemorrhagic *E. coli* strains (5). EcN is an excellent colonizer of the human gut, and exhibits beneficial effects in various intestinal dysfunctions such as acute diarrhea in infants and toddlers (6), chronic constipation (7), and abdominal pain in patients with irritable bowel syndrome (8). It has been widely used in the treatment of inflammatory bowel diseases (1) and has proven to be as effective as the gold standard mesalazine for the maintenance of remission in ulcerative colitis in children and adults (9).

EcN probiotic activity is believed to be based on multiple peculiar properties and fitness determinants, including antibacterial activities against other bacteria (10). Thanks to an extensive list of siderophores (enterobactin, salmochelin, yersiniabactin, and aerobactin) and multiple siderophore receptors and iron transport systems, EcN reduces *S. Typhimurium* intestinal colonization by competing for iron (3). Enterobactin, salmochelin and yersiniabactin are nonribosomal peptides (NRP) or polyketide (PK)-NRP hybrids, which are synthesized by NRP synthetases and PK synthases (NRPS and PKS) activated by a cognate phosphopantetheinyl transferase (PPTase). In addition to this competition for a limiting nutrient, EcN exhibits a direct antibacterial activity linked to the production of two microcins (Mcc), H47 (MccH47) and M (MccM) (4,11-13). Mcc are secreted low-molecular weight peptides that are synthesized by ribosomes and posttranslationally modified, and which display a potent bactericidal activity against phylogenetically-related bacteria (14,15). MccH47 and MccM are called "siderophore-Mcc" because they are modified posttranslationally by the linkage of a catechol siderophore (13,16). The C-terminus of the Mcc peptide is covalently bound with a linearized and glycosylated derivative of enterobactin (13, 16,17). This siderophore moiety is recognized by the catecholate-siderophore receptors of the target bacterium (12, 16). The siderophore-Mcc can therefore enter and kill the sensitive bacterium by a "Trojan Horse" stratagem, by mimicking the iron-siderophore complexes.

Comparative genomic analyses have shown that EcN is closely related to pathogenic *E. coli* strains such as the uropathogenic strain CFT073 (18-20). EcN and CFT073 share eight genomic islands, including the pks/clb island encoding a NRPS-PKS assembly line that synthesizes the genotoxin colibactin (21, 22). Colibactin is produced as a prodrug moiety that is exported in the periplasm by the efflux pump ClbM (23) and then hydrolyzed by the periplasmic membrane-bound ClbP protein with a peptidase activity, which releases the active colibactin (24,25). Colibactin is not only a bona fide virulence factor (26,27) but also a putative procarcinogenic compound. Colibactin alkylates the host cell DNA, resulting in DNA crosslinks, double-strand breaks, chromosome aberrations and gene mutations both in vitro and in vivo (21,22,28-30). Colibactin-producing *E. coli* are overrepresented in biopsies of patients with colorectal cancer (31,32) and they were shown to promote colorectal cancer in mouse models (31,33).

The ambivalence between the pathogenic and probiotic potential of EcN was uncovered when inventors showed that certain enzymes of the pks/clb island enable the synthesis of analgesic lipopeptides (34) and that the probiotic properties of EcN are related to the presence of the pathogenicity island (35). In the Olier et al. (2012) study, inventors inactivated the gene that encodes the phosphopantetheinyl transferase (PPTase) ClbA, which was thought to be specific for colibactin synthesis. However, more recent work has shown that ClbA has a pleiotropic effect and also modulates the synthesis of siderophores as well as that of the analgesic lipopeptides (34,36). As might be expected, use of a probiotic strain that produces a genotoxin is a public health concern. Inventors therefore attempted to clearly decouple the genotoxic from the probiotic activities. In this study, inventors used their knowledge of the biosynthetic pathway of colibactin and other secondary metabolites produced directly or indirectly by the pks/clb island to specifically abrogate the genotoxic activity of colibactin. Inventors examined the ability of mutants to inhibit the growth of pathogenic bacteria while still producing beneficiary secondary metabolites. Inventors successfully decoupled the probiotic activity from the genotoxic activity, consequently opening the way to optimize EcN. However, inventors were surprised to observe that the pks/clb island was even more intimately connected to EcN probiotic activity than we expected, and that there was a co-evolution of pathogenic and probiotic properties in bacteria. EcN is, to some extent, like the "miracle drug" aspirin. Although, like aspirin, this bacterial strain has been used successfully for over a century, it is crucial to understand the method of action and to take into account the safety and potential side effects.

SUMMARY OF THE INVENTION

The invention is based on the study of the mechanisms implicated in the probiotic properties of the *Escherichia coli* strain Nissle 1917 (EcN). In addition to the production of two siderophore-microcins (Mcc) responsible for its direct antibacterial effect, EcN synthesizes the genotoxin colibactin encoded by the pks island. Colibactin is a virulence factor and a putative pro-carcinogenic compound. Therefore, this study has allowed the inventors to decouple the probiotic activity of EcN from its genotoxic activity. They demonstrated that the pks-encoded ClbP, the enzyme that activates the genotoxin colibactin, is required for the siderophore-microcins activity of probiotic EcN, but interestingly, not its enzymatic domain that cleaves precolibactin to form active colibactin. This study has allowed the inventors to decouple the siderophore-microcins from the genotoxic activities by specifically targeting the peptidase domain of ClbP which opens the way to safe use of EcN. Indeed, ClbP peptidase activity mandatory for colibactin production, has no role in siderophore-microcin production, which provides a way to construct a non-genotoxic strain that retains its antibacterial activity. Furthermore, inventors demonstrate in an in vivo animal model infected by an intestinal bacterial pathogen (*S. Typhimurium*) that administration of an EcN modified strain with clbP gene encoding ClbP protein inactive for the peptidase domain (ie. ClbP mutated at position S95), is non-genotoxic (do not produce colibactin) but keeps the bacterial antagonist activity, and reduces colonization and virulence of the pathogen (FIG. 8) by maintaining the siderophore-microcin production.

Thus, in a first aspect, the present invention provides an *Escherichia coli* strain Nissle 1917 (EcN) bacterium carrying a gene encoding ClbP protein which is inactive for the peptidase domain, wherein the peptidase domain of ClbP protein having the amino acid sequence of SEQ ID NO:3 is involved in activation of the genotoxin colibactin.

A second object of the invention relates to an *Escherichia coli* strain Nissle 1917 (EcN) bacterium, as defined above for use as a drug.

A third object of the invention relates to an *Escherichia coli* strain Nissle 1917 (EcN) bacterium, as defined above for use in the treatment of gastro-intestinal disease.

DETAILED DESCRIPTION OF THE INVENTION

Modified *Escherichia coli* Strain Nissle 1917

In a first aspect, the present invention provides an *Escherichia coli* strain Nissle 1917 (EcN) bacterium carrying an gene encoding a ClbP protein which is inactive for the peptidase domain, wherein the peptidase domain of ClbP protein having the amino acid sequence of SEQ ID NO:3 is involved in activation of the genotoxin colibactin.

The inventors have shown that the natural (wild-type) ClbP protein having the amino acid sequence of SEQ ID NO:1, the enzyme that activates the genotoxin colibactin, is also required for the siderophore-microcins activity of probiotic EcN, but interestingly, not its enzymatic domain that cleaves precolibactin to form active colibactin. In particular, the inventors have shown that, mutants EcN bacteria for the gene encoding the ClbP protein which is inactivate only for the peptidase domain according to the invention (ie. mutant S95A, S95R, K98T or ClbP-3H), these mutant maintain in vitro and in vivo its antibacterial activity (through siderophore-MCC production) but not mutant EcN bacteria with an inactivated gene encoding the whole ClbP protein (i.e. see FIG. 4 of Example section). These results evidence that ClbP peptidase activity mandatory for colibactin production, has no role in siderophore-microcin production, which provides a way to construct a non-genotoxic EcN strain that retains its antibacterial activity. Consequently, the mutants EcN bacteria, according to the invention, trigger a more safe and protective response, and thus constitute very promising new probiotic as demonstrated with the in vivo data using modified EcN strain according to the invention (see FIG. 8).

The term "*Escherichia coli* strain Nissle 1917" (also called EcN or DSM6601) means a probiotic *Escherichia coli* strain which was isolated during World War I by Alfred Nissle in a soldier who resisted a severe diarrhea outbreak (1,2). EcN was initially studied for its ability to fight bacterial gastrointestinal infections. It was demonstrated to impede intestinal colonization by *Salmonella enterica* serovar *Typhimurium* (3,4) and to exhibit an antibacterial activity against enterohemorrhagic *E. coli* strains (5). EcN is an excellent colonizer of the human gut, and exhibits beneficial effects in various intestinal dysfunctions such as acute diarrhea in infants and toddlers (6), chronic constipation (7), and abdominal pain in patients with irritable bowel syndrome (8). It has been widely used in the treatment of inflammatory bowel diseases (1) and has proven to be as effective as the gold standard mesalazine for the maintenance of remission in ulcerative colitis in children and adults (9).

*Escherichia coli* Nissle 1917 (EcN) is the active component of Mutaflor® (Ardeypharm GmbH, Herdecke, Germany), a probiotic drug licensed in several countries for the treatment of multiple intestinal disorders (10). EcN is known to harbour a genomic island, named pks, which carries a cluster of genes that enables the synthesis of hybrid peptide polyketides and especially a genotoxin called colibactin (21). Colibactin is a structurally uncharacterized PK-NRP that is thought to arise from a pro-drug called precolibactin, which has also not been fully structurally elucidated (Li, Z. R. et al. Nat Chem Biol 12, 773-5 (2016); Bode, H. B. Angew Chem Int Ed Engl 54, 10408-11 (2015)). This toxin is produced by a complex biosynthetic machinery involving the sequential action of proteins ClbA to ClbS (Taieb, F., et al EcoSal Plus 7(2016)). The core machinery consists of three polyketide synthases, three non-ribosomal peptide synthetases and two hybrids PKS-NRPS. The machinery also employs additional maturation proteins and efflux pump(s).

Colibactin is produced as a prodrug moiety that is exported in the periplasm by the efflux pump ClbM (23) and then hydrolyzed by the periplasmic membrane-bound ClbP protein with a peptidase activity, which releases the active colibactin (24,25). Colibactin is not only a bona fide virulence factor (26,27) but also a putative procarcinogenic compound.

The term "ClbP protein" means a peptidase encoded by the pks genomic island of *Escherichia coli* (and other *Enterobacteriaceae*). ClbP protein contains an N-terminal signal sequence that targets the protein to the inner membrane, a periplasmic peptidase domain containing the active site of protease (the AA residues forming the peptidase being 39-337), and three C-terminal transmembrane helices (the AA residues forming the three transmembrane helices being 390-412, 433-455, and 465-485). ClbP crystal structure and mutagenesis experiments revealed a serine-active site and original structural features, associated with a peptidase activity (24) ClbP allows the maturation of precolibactin in genotoxic colibactin through ClbP peptidase activity that removes the N-acyl-D-asparagine prodrug scaffold from precolibactin (24,25). S95 K98 and Y186 are key residues for ClbP peptidase activity, and mutants for these residues fail to cleave precolibactin to release mature active genotoxin (24,25).

The sequences of ClbP are indicated in the following Table 1:

| ClbP | Sequence | | | |
|---|---|---|---|---|
| Acid amino sequence of ClbP wild type (SEQ ID NO: 1) | MTIMEHVSIK ERLSTLIHQR SQKANTLDTV ITYLPEMRLN PMPGSAVAQQ | TLYHLLCCML MQEAKVPALS YELGSMSKAF YQGKPASLTV LRNENLLFAP | LFISAMCALA VSVTIKGVRQ TGLVVQILIQ ADFLYHTSGL GAKFSYASAN | QEHEPIGAQD RFVYGVADVA EGRLRQGDDI PFSTLARLEN YDVLGAVIEN |

| ClbP | Sequence |
|---|---|
| | VTGKTFTEVI AERLTQPLGM SATVAVKGDE IIVNKASGYK<br>LGFGKPVLFH APLARNHVPA AYIHSTLPDM EIWIDAWLHR<br>KALPATLREA MSNSWRGNSD VPLAADNRIL YASGWFIDQN<br>QGPYISHGGQ NPNFSSCIAL RPDQQIGIVA LANMNSNLIL<br>QLCADIDNYL RIGKYADGAG DAITATDTLF VYLTLLLCFW<br>GAVVVVRGAF RVYRATAHGP GKQQRLRLRV<br>RDYIIALAVP GLVAAMLYVA PGILSPGLDW RFILVWGPSS<br>VLAIPFGIIL LAFVLTLNHQ IKRILLHNKE WDDE |
| Nucleic sequence (ADNc) of ClbP wild type (SEQ ID NO:_2) | atgacaataatggaacacgttagcattaaaacattatatcatctcctgtgctgtatgctgctctttatt<br>tccgctatgtgcgctttggcgcaagaacatgagcctatcggggcgcaagatgagcgcctgtcg<br>acattaattcaccaacggatgcaggaggccaaggtcccagcccttccgtaagtgtgaccatta<br>aggggggtacgtcagcgatttgtctacggtgttgccgatgtggctagtcagaaagcgaatactcta<br>gacacagtttacgagctgggatcgatgagtaaggcgtttaccggacttgtggtgcaaatactgat<br>tcaggaaggcagactccggcaaggggatgatatcattacctatctgccggaaatgcgcttgaat<br>tatcagggaaaacctgatccctgaccgtggctgatttcctttatcatacatcaggattgccttttttc<br>aacactggctcggctggaaaaccctatgcctgggagcgctgtggcacagcaactgcgcaacg<br>agaatctgctgtttgcgccgggtgcgaagtttagctatgcctccgccaattatgatgtgttgggcg<br>cggtgattgaaaatgtgacgggaaaaaccttta cagaggtcattgcggaacgactcacgcagc<br>cgctgggcatgtcggcgactgtggcagttaaggggaagtgagattattgtcaacaaggcaagcg<br>gctataaactgggattcggcaaaccc gttctgtttcatgcgcctctgtgcccggaaccatgttcctg<br>ccgcctatatccatagcactctgcctgatatggaaatatggatagacgcctggttgcacagaaag<br>gctttgccggcaacgctgcgtgaggcgatgagtaacagttggcgtggtaatagtgatgttccgc<br>ttgccgcagacaatcgtatcctctatgccagcggttggtttatcgaccagaatcaaggcccttaca<br>tcagtcacggtgggcagaatccaaacttttcttcttgcattgcgttgcgaccggatcagcagattg<br>gcattgttgcgctggcaaatatgaattcgaatctgatactacagctttgcgcggatatcgataatta<br>tctgcgcattggcaaatatgctgacggcgctggtgatgcaattacagccaccgataccctttcgt<br>ctacctcacgttgttgctgtgtttttgggggcggtggttgtagtgcgcggtgctttccgtgtttatc<br>gcgcaacggcgcatggccctggaaaacagcagaggttacgtttacgcgtacgtgactatatcat<br>cgccttggcggttcctgggctcgtggccgccatgctctatgtcgcaccgggtatactatctccag<br>gacttgactggcgttttatcttggtatggggtccatcgagcgtgttggcgataccgttcggaattat<br>cctgttagctttcgttctgacattaaatcatcaaattaaacgaattctattacacaacaaggagtgg<br>gacgatgagtaa |
| Acid amino sequence of peptidase domain ClbP (SEQ ID NO:_3) | QD ERLSTLIHQR MQEAKVPALS VSVTIKGVRQ<br>RFVYGVADVA SQKANTLDTV YELGSMSKAF TGLVVQILIQ<br>EGRLRQGDDI ITYLPEMRLN YQGKPASLTV ADFLYHTSGL<br>PFSTLARLEN PMPGSAVAQQ LRNENLLFAP GAKFSYASAN<br>YDVLGAVIEN VTGKTFTEVI AERLTQPLGM SATVAVKGDE<br>IIVNKASGYK LGFGKPVLFH APLARNHVPA AYIHSTLPDM<br>EIWIDAWLHR KALPATLREA MSNSWRGNSD VPLAADNRIL<br>YASGWFIDQN QGPYISHGGQ NPNF SSC |

According to the invention, the term "a gene encoding a ClbP protein which is inactive for the peptidase domain", means that it is meant a gene with mutation that encodes either a non-functional peptidase domain (such as ClbP S95, K98, Y186 mutants) or no peptidase domain at all ((such as ClbP-3H mutants). According to the invention, the inactivation of a specific domain of a gene can be carried out by the various methods known by the skilled person. Examples of methods for inactivating a gene are particularly the directed mutagenesis or the homologous recombination, as described in Conde-Alvarez R. et al., Cell Microbiol 2006 August; 8(8):1322-35. A man skilled in the art, also knows as to design a specific "nuclease" or "endonuclease" (such as CRISPR) in order to introduce a genetic point mutations to inactivate the peptidase domain of ClbP protein or to genetically recombinate specifically the peptidase domain of ClbP protein in order to replace with an non active equivalent.

A particular method for inactivating a specific domain of a gene according to the invention is also described in the experimental section (Gene mutagenesis performed by the lambda Red recombinase method (see 37)).

Thus typically, an EcN mutant according to the invention (i) has the capacity to have an antibacterial activity (through synthesis of siderophore-MCC: MccH47 and MccM); and ii) which is devoid of the capacity to activate the genotoxin colibactin (with an inactivate ClbP peptidase domain).

The skilled in the art can easily determine whether EcN bacterium according to the invention is biologically active. For example, the capacity to have an antibacterial activity can for example be determined by any routine test well known by the man skills in the art: antibiograms, Competitive growth assay, . . . .

The effect of antibacterial activity can be measured by monitoring reduction of the target bacterial strains (sensible to EcN such as *E. coli* strain LF82) present in a surface prior to and after application with the mutant EcN compositions according to the invention, using in vitro assays (Competitive growth assay). Both the producing and the target strains (ie. EcN or EcN mutants and LF82 respectively) are inoculated as previously described ((3) and also as described in Example+FIGS. 1 to 5).

The determination of a genotoxic effect induced by colibactin (for EcN mutant candidate) can be measured by monitoring the cellular senescence induced by colibactin with the associated cell enlargement called megalocytosis. As previously described (40), HeLa cells are infected for 4 hours with the EcN candidate. The genotoxicity of EcN and the EcN mutant (ie clbP-S95R) is confirmed by an In-Cell Western procedure, as previously described (36). In brief, HeLa cells are infected for 4 hours at a given multiplicity of infection (number of bacteria per cell at the onset of infection). Four hours after the end of infection cells are fixed, permeabilized and stained with rabbit monoclonal anti-gamma-H2AX followed by an infrared fluorescent secondary antibody.

As used herein, a "biologically active" EcN mutant according to the invention refers to an EcN mutant exhibiting all, of the biological activities of an EcN mutant, provided the biologically active mutant retains the wild-type EcN capacity of antibacterial activity but are devoid of the capacity to activate the genotoxin colibactin. The biologically active EcN mutant according to the invention may for example be characterized in that it is capable of having an antibacterial activity (through production of siderophore-MCC); and ii) is devoid of the capacity to activate the genotoxin colibactin (having an inactivate ClbP peptidase domain) (see Example and FIG. 5).

In particular embodiment of the invention, the ClbP protein inactivate for the peptidase domain, is selected from the list consisting of ClbP protein mutated at position S95,
ClbP protein mutated at position K98,
ClbP protein mutated at position Y186
ClbP protein without peptidase domain (SEQ ID N° 3)

In the present invention the numbering of amino acids regarding mutations (punctual mutation or recombination of the peptidase domain) is according to the wild type ClbP protein sequence (SEQ ID NO: 1).

In a preferred embodiment the ClpP protein mutated at position S95, is preferably not substituted with an equivalent polar and non-charged amino acid of Serine. Accordingly, the ClbP protein mutated at position S95 is preferably not substituted with Threonine, Asparagine or Glutamine.

In a preferred embodiment the ClpP protein mutated at position K98, is preferably not substituted with an equivalent positively charged amino acid of Lysine. Accordingly, ClbP protein mutated at position K98, is preferably not substituted with Arginine, Asparagine or Histidine.

In a preferred embodiment the ClbP protein mutated at position Y186, is preferably not substituted with an equivalent amino acid with hydrophobic side chain of Tyrosine. Accordingly, ClbP protein mutated at position Y186, is preferably not substituted with alanine, Valine, Isoleucine, Leucine, Methionine, Phenylalanine or Tryptophan.

In a preferred embodiment the ClbP protein without peptidase domain, the peptidase domain of ClbP is substituted or replace with a peptidic domain having a molecular weight between 15 and 150 kDa, preferably between 25 and 100 kDa, more preferably between 30 and 80 kDa, even more preferably between 30 and 50 kDa.

This substitution with a peptidic domain (equivalent in weight but devoid of any ClbP peptidase activity which consist to remove the N-acyl-D-asparagine prodrug scaffold from precolibactin to form colibactin (24,25)) allow to maintain the three-dimensional structure and organisation of the mutant ClbP protein and to maintain the antibacterial activity.

Example of peptidic domain which can used to replace the peptidase domain of ClbP is the mature form of the alkaline phosphatase PhoA encoded by the *Escherichia coli* phoA gene, or the mature form of the enzyme beta-lactamase, encoded by the bla gene, or the mature form of the enzyme β-galactosidase encoded by the *Escherichia coli* lacZ gene.

These examples of peptidic domain (alkaline phosphatase PhoA, enzyme beta-lactamase enzyme β-galactosidase) are the most commonly used, especially alkaline phosphatase PhoA (as in the present study) as reporter protein for gene fusion studies in prokaryotes, especially for transmembrane fusion protein having a periplasmic domain (see the review van Geest M. and. Lolkema J S. Microbiol Mol Biol Rev. 2000 March; 64(1): 13-33).

In a preferred embodiment, the ClbP protein inactivate for the peptidase domain without peptidase domain, is ClbP protein with a peptidase domain substituted by alkaline phosphatase enzymatic domain of PhoA (SEQ ID N° 11). The capacity to create gene fusion is well known by the man skills in the art. Regarding this ClbP fusion protein, only the mature part of PhoA, lacking its signal sequence, is fused behind C-terminal truncated parts of a membrane protein (see also the review van Geest M. and. Lolkema J S. Microbiol Mol Biol Rev. 2000 March; 64(1): 13-33). More precisely the PhoA domain is fused with the ClbP N-terminal signal sequence which allows the translocation to periplasm, and the ClbP C-terminal sequence from amino-acid 390; the residues forming the three transmembrane helices being 390-412, 433-455, and 465-485 (see Example section).

As used herein, the term "amino acid" refers to natural or unnatural amino acids in their D and L stereoisomers for chiral amino acids. It is understood to refer to both amino acids and the corresponding amino acid residues, such as are present, for example, in peptidyl structure. Natural and unnatural amino acids are well known in the art. Common natural amino acids include, without limitation, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr), and valine (Val).

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan and tyrosine are classified as both polar and aromatic amino acids. Amino acids may further be classified as non-charged, or charged (positively or negatively) amino acids. Examples of positively charged amino acids include without limitation lysine, arginine and histidine. Examples of negatively charged amino acids include without limitation glutamic acid and aspartic acid. Additional amino acids that are classified in each of the above groups are known to those of ordinary skill in the art.

"Equivalent amino acid" means an amino acid which may be substituted for another amino acid in the peptide compounds according to the invention without any appreciable loss of function. Equivalent amino acids will be recognized by those of ordinary skill in the art. Substitution of like amino acids is made on the basis of relative similarity of side chain substituents, for example regarding size, charge, hydrophilicity and hydrophobicity as described herein. The phrase "an equivalent amino acid" when used following a list of individual amino acids means an equivalent of one or more of the individual amino acids included in the list.

In a more particular embodiment of the invention, the ClbP protein inactivate for the peptidase domain, encoded by the gene is selected from the list consisting of ClbP S95A mutant (SEQ ID N° 4),
ClbP K98T mutant (SEQ ID N° 6),
ClbP S95R mutant (SEQ ID N° 8)
ClbP Y186G mutant (SEQ ID N° 10)
ClbP protein with a peptidase domain substituted by alkaline phosphatase enzymatic domain of PhoA (SEQ ID N° 11).

The sequences of mutated ClbP according to the invention are indicated in the following Table 2:

| Mutant ClbP | Sequence |
|---|---|
| Acid amino sequence of ClbP S95A (SEQ ID NO: 4) | MTIMEHVSIK TLYHLLCCML LFISAMCALA QEHEPIGAQD ERLSTLIHQR MQEAKVPALS VSVTIKGVRQ RFVYGVADVA SQKANTLDTV YELGAMSKAF TGLVVQILIQ EGRLRQGDDI ITYLPEMRLN YQGKPASLTV ADFLYHTSGL PFSTLARLEN PMPGSAVAQQ LRNENLLFAP GAKFSYASAN YDVLGAVIEN VTGKTFTEVI AERLTQPLGM SATVAVKGDE IIVNKASGYK LGFGKPVLFH APLARNHVPA AYIHSTLPDM EIWIDAWLHR KALPATLREA MSNSWRGNSD VPLAADNRIL YASGWFIDQN QGPYISHGGQ NPNFSSCIAL RPDQQIGIVA LANMNSNLIL QLCADIDNYL RIGKYADGAG DAITATDTLF VYLTLLLCFW GAVVVVRGAF RVYRATAHGP GKQQRLRLRV RDYIIALAVP GLVAAMLYVA PGILSPGLDW RFILVWGPSS VLAIPFGIIL LAFVLTLNHQ IKRILLHNKE WDDE |
| Nucleic sequence (ADNc) of ClbP S95A (SEQ ID NO: 5) | Atgacaataatggaacacgttagcattaaaacattatatcatctcctgtgctgtatgctgctctttat tccgctatgtgcgctttggcgcaagaacatgagcctatcggggcgcaagatgagcgcctgtcg acattaattcaccaacggatgcaggaggccaaggtcccagccctttccgtaagtgtgaccatta aggggtacgtcagcgatttgtctacggtgttgccgatgtggctagtcagaaagcgaatactcta gacacagtttacgagctgggagcgatgagtaaggcgtttaccggacttgtggtgcaaatactga ttcaggaaggcagactccggcaaggggatgatatcattacctatctgccggaaatgcgcttgaa ttatcagggaaaacctgatccctgaccgtggctgatttccttatcatacatcaggattgccttttc aacactggctcggctggaaaaacctatgcctgggagcgctgtggcacagcaactgcgcaacg agaatctgctgtttgcgccgggtgcgaagtttagctatgcctccgccaattatgatgtgttgggcg cggtgattgaaaatgtgacgggaaaaaccttacagaggtcattgcggaacgactcacgcagc cgctgggcatgtcggcgactgtggcagttaaggggatgagattattgtcaacaaggcaagcg gctataaactgggattcggcaaacccgttctgtttcatgcgcctctggcccggaaccatgttcctg ccgcctatatccatagcactctgcctgatatgagaatatggatagacgcctggttgcacagaaag gctttgccggcaacgctgcgtgaggcgatgagtaacagttggcgtggtaatagtgatgttccgc ttgccgcagacaatcgtatcctctatgccagcggttggtttatcgaccagaatcaaggcccttaca tcagtcacggtgggcagaatccaaacttttcttcttgcattgcgttgcgaccggatcagcagattg gcattgttgcgctggcaaatatgaattcgaatctgatactacagctttgcgcggatatcgataatta tctgcgcattggcaaatatgctgacggcgctggtgatgcaattacagccaccgatacccttficgt ctacctcacgttgttgctgtgtttttgggggcggtggttgtagtgcgcggtgctttccgtgtttatc gcgcaacggcgcatggccctggaaaacagcagaggttacgtttacgcgtacgtgactatatcat cgccttggcggttcctgggctcgtggccgccatgctctatgtcgcaccgggtatactatctccag gacttgactggcgttttatcttggtatggggtccatcgagcgtgttggcgataccgttcggaattat cctgttagctttcgttctgacattaaatcatcaaattaaacgaattctattacacaacaaggagtgg gacgatgagtaa |
| Acid amino sequence of ClbP K98T (SEQ ID NO: 6) | MTIMEHVSIK TLYHLLCCML LFISAMCALA QEHEPIGAQD ERLSTLIHQR MQEAKVPALS VSVTIKGVRQ RFVYGVADVA SQKANTLDTV YELGSMSTAF TGLVVQILIQ EGRLRQGDDI ITYLPEMRLN YQGKPASLTV ADFLYHTSGL PFSTLARLEN PMPGSAVAQQ LRNENLLFAP GAKFSYASAN YDVLGAVIEN VTGKTFTEVI AERLTQPLGM SATVAVKGDE IIVNKASGYK LGFGKPVLFH APLARNHVPA AYIHSTLPDM EIWIDAWLHR KALPATLREA MSNSWRGNSD VPLAADNRIL YASGWFIDQN QGPYISHGGQ NPNFSSCIAL RPDQQIGIVA LANMNSNLIL QLCADIDNYL RIGKYADGAG DAITATDTLF VYLTLLLCFW GAVVVVRGAF RVYRATAHGP GKQQRLRLRV RDYIIALAVP GLVAAMLYVA PGILSPGLDW RFILVWGPSS VLAIPFGIIL LAFVLTLNHQ IKRILLHNKE WDDE |
| Nucleic sequence (ADNc) of ClbP mutated at position S95 (SEQ ID NO: 7) | atgacaataatggaacacgttagcattaaaacattatatcatctcctgtgctgtatgctgctctttatt tccgctatgtgcgctttggcgcaagaacatgagcctatcggggcgcaagatgagcgcctgtcg acattaattcaccaacggatgcaggaggccaaggtcccagccattccgtaagtgtgaccatta aggggtacgtcagcgatttgtctacggtgttgccgatgtggctagtcagaaagcgaatactcta gacacagtttacgagctgggagcgatgagtaaggcgtttaccggacttgtggtgcaaatactga ttcaggaaggcagactccggcaaggggatgatatcattacctatctgccggaaatgcgcttgaa ttatcagggaaaacctgatccctgaccgtggctgatttccttatcatacatcaggattgccttttc aacactggctcggctggaaaaacctatgcctgggagcgctgtggcacagcaactgcgcaacg agaatctgctgtttgcgccgggtgcgaagtttagctatgcctccgccaattatgatgtgttgggcg cggtgattgaaaatgtgacgggaaaaaccttacagaggtcattgcggaacgactcacgcagc cgctgggcatgtcggcgactgtggcagttaaggggatgagattattgtcaacaaggcaagcg gctataaactgggattcggcaaacccgttctgtttcatgcgcctctggcccggaaccatgttcctg ccgcctatatccatagcactctgcctgatatgaaatatggatagacgcctggttgcacagaaag |

| Mutant ClbP | Sequence |
|---|---|
| | gctttgccggcaacgctgcgtgaggcgatgagtaacagttggcgtggtaatagtgatgttccgc<br>ttgccgcagacaatcgtatcctctatgccagcggttggtttatcgaccagaatcaaggcccttaca<br>tcagtcacggtgggcagaatccaaacttttatcttgcattgcgttgcgaccggatcagcagattg<br>gcattgttgcgctggcaaatatgaattcgaatctgatactacagctttgcgcggatatcgataatta<br>tctgcgcattggcaaatatgctgacggcgctggtgatgcaattacagccaccgatacccttttcgt<br>ctacctcacgttgttgctgtgttttttgggggggcggtggttgtagtgcgcggtgctttccgtgtttatc<br>gcgcaacggcgcatggccctggaaaacagcagaggttacgtttacgcgtacgtgactatatcat<br>cgccttggcggttcctgggctcgtggccgccatgctctatgtcgcaccgggtatactatctccag<br>gacttgactggcgttttatcttggtatggggtccatcgagcgtgttggcgataccgttcggaattat<br>cctgttagctttcgttctgacattaaatcatcaaattaaacgaattctattacacaacaaggagtgg<br>gacgatgagtaa |
| Acid amino sequence<br>of ClbP S95R<br>(SEQ ID NO: 8) | MTIMEHVSIK TLYHLLCCML LFISAMCALA QEHEPIGAQD<br>ERLSTLIHQR MQEAKVPALS VSVTIKGVRQ RFVYGVADVA<br>SQKANTLDTV YELGRMSKAF TGLVVQILIQ EGRLRQGDDI<br>ITYLPEMRLN YQGKPASLTV ADFLYHTSGL PFSTLARLEN<br>PMPGSAVAQQ LRNENLLFAP GAKFSYASAN YDVLGAVIEN<br>VTGKTFTEVI AERLTQPLGM SATVAVKGDE IIVNKASGYK<br>LGFGKPVLFH APLARNHVPA AYIHSTLPDM EIWIDAWLHR<br>KALPATLREA MSNSWRGNSD VPLAADNRIL YASGWFIDQN<br>QGPYISHGGQ NPNFSSCIAL RPDQQIGIVA LANMNSNLIL<br>QLCADIDNYL RIGKYADGAG DAITATDTLF VYLTLLLCFW<br>GAVVVVRGAF RVYRATAHGP GKQQRLRLRV<br>RDYIIALAVP GLVAAMLYVA PGILSPGLDW RFILVWGPSS<br>VLAIPFGIIL LAFVLTLNHQ IKRILLHNKE WDDE |
| Nucleic sequence<br>(ADNc) of ClbP S95R<br>(SEQ ID NO: 9) | atgacaataatggaacacgttagcattaaaacattatatcatctcctgtgctgtatgctgctctttatt<br>tccgctatgtgcgctttggcgcaagaaacatgagcctatcggggcgcaagatgagcgcctgtcg<br>acattaattcaccaacggatgcaggaggccaaggtcccagcccctttccgtaagtgtgaccatta<br>agggggtacgtcagcgatttgtctacggtgttgccgatgtggctagtcagaaagcgaatactcta<br>gacacagtttacgagctgggacggatgagtaaggcgtttaccggacttgtggtgcaaatactga<br>ttcaggaaggcagactccggcaaggggatgatatcattacctatctgccggaaatgcgcttgaa<br>ttatcagggaaaacctgatccctgaccgtggctgatttccttatcatacatcaggattgccifittc<br>aacactggctcggctggaaaacccatgcctgggagcgctgtggcacagcaactgcgcaacg<br>agaatctgctgtttgcgccgggtgcgaagtttagctatgcctccgccaattatgatgtgttgggcg<br>cggtgattgaaaatgtgacgggaaaaacctttacagaggtcattgcggaacgactcacgcagc<br>cgctgggcatgtcggcgactgtggcagttaaggggggatgagattattgtcaacaaggcaagcg<br>gctataaactgggattcggcaaacccgttctgtttcatgcgcctctggcccggaaccatgttcctg<br>ccgcctatatccatagcactctgcctgatatggaaatatggatagacgcctggttgcacagaaag<br>gctttgccggcaacgctgcgtgaggcgatgagtaacagttggcgtggtaatagtgatgttccgc<br>ttgccgcagacaatcgtatcctctatgccagcggttggtttatcgaccagaatcaaggcccttaca<br>tcagtcacggtgggcagaatccaaacttttcttcttgcattgcgttgcgaccggatcagcagattg<br>gcattgttgcgctggcaaatatgaattcgaatctgatactacagctttgcgcggatatcgataatta<br>tctgcgcattggcaaatatgctgacggcgctggtgatgcaattacagccaccgataccctificgt<br>ctacctcacgttgttgctgtgttttttgggggggcggtggttgtagtgcgcggtgctttccgtgtttatc<br>gcgcaacggcgcatggccctggaaaacagcagaggttacgtttacgcgtacgtgactatatcat<br>cgccttggcggttcctgggctcgtggccgccatgctctatgtcgcaccgggtatactatctccag<br>gacttgactggcgttttatcttggtatggggtccatcgagcgtgttggcgataccgttcggaattat<br>cctgttagctttcgttctgacattaaatcatcaaattaaacgaattctattacacaacaaggagtgg<br>gacgatgagtaa |
| Acid amino sequence<br>of ClbP Y186G<br>(SEQ ID NO: 10) | MTIMEHVSIK TLYHLLCCML LFISAMCALA QEHEPIGAQD<br>ERLSTLIHQR MQEAKVPALS VSVTIKGVRQ RFVYGVADVA<br>SQKANTLDTV YELGSMSKAF TGLVVQILIQ EGRLRQGDDI<br>ITYLPEMRLN YQGKPASLTV ADFLYHTSGL PFSTLARLEN<br>PMPGSAVAQQ LRNENLLFAP GAKFSGASAN YDVLGAVIEN<br>VTGKTFTEVI AERLTQPLGM SATVAVKGDE IIVNKASGYK<br>LGFGKPVLFH APLARNHVPA AYIHSTLPDM EIWIDAWLHR<br>KALPATLREA MSNSWRGNSD VPLAADNRIL YASGWFIDQN<br>QGPYISHGGQ NPNFSSCIAL RPDQQIGIVA LANMNSNLIL<br>QLCADIDNYL RIGKYADGAG DAITATDTLF VYLTLLLCFW<br>GAVVVVRGAF RVYRATAHGP GKQQRLRLRV<br>RDYIIALAVP GLVAAMLYVA PGILSPGLDW RFILVWGPSS<br>VLAIPFGIIL LAFVLTLNHQ IKRILLHNKE WDDE |
| Acid amino sequence<br>of ClbP-3H: ClbP<br>protein with a peptidase<br>domain substituted by<br>alkaline phosphatase<br>enzymatic domain of<br>PhoA (fusion protein)<br>(SEQ ID NO: 11) | MTIMEHVSIKTLYHLLCCMLLFISAMCALAQEHEPIGAMPV<br>LENRAAQGDITAPGGARRLTGDQTAALRDSLSDKPAKNI<br>ILLIGDMGDSEITAARNYAEGAGGFFKGIDALPLTGQY<br>THYALNKKTGKPDYVTDSAASATAWSTGVKTYNGALGV<br>DIHEKDHPTILEMAKAAGLATGNVSTAELQDATPAALVA<br>HVTSRKCYGPSATSEKCPGNALEKGGKGSITEQLLNARA<br>DVTLGGGAKTFAETATAGEWQGKTLREQAQARGYQLV<br>SDAASLNSVTEANQQKPLLGLFADGNMPVRWLGPKATY<br>HGNIDKPAVTCTPNPQRNDSVPTLAQMTDKAIELLSKNE<br>KGFFLQVEGASIDKQDHAANPCGQIGETVDLDEAVQRAL<br>EFAKKEGNTLVIVTADHAHASQIVAPDTKAPGLTQALNT<br>KDGAVMVMSYGNSEEDSQEHTGSQLRIAAYGPHAANVV |

| Mutant ClbP | Sequence |
|---|---|
| | GLTDQTDLFYTMKAALGLKIALRPDQQIGIVALANMNSNL<br>ILQLCADIDNYLRIGKYADGAGDAITATDTLFVYLTLLLCFW<br>GAVVVVRGAFRVYRATAHGPGKQQRLRLRVRDYIIALAVP<br>GLVAAMLYVAPGILSPGLDWRFILVWGPSSVLAIPFGIILLAF<br>VLTLNHQIKRILLHNKEWDDE |
| Nucleic sequence<br>(ADNc) of ClbP-3H:<br>ClbP protein with a<br>peptidase domain<br>substituted by alkaline<br>phosphatase enzymatic<br>domain of PhoA<br>(fusion protein)<br>(SEQ ID NO: 12) | atgcctgttctggaaaaccgggctgctcagggcgatattactgcacccggcggtgctcgccgtt<br>taacgggtgatcagactgccgctctgcgtgattctcttagcgataaacctgcaaaaaatattttt<br>gctgattggcgatgggatgggggactcggaaattactgccgcacgtaattatgccgaaggtgc<br>gggcggcttttttaaaggtatagatgccttaccgcttaccgggcaatacactcactatgcgctgaa<br>taaaaaaaccggcaaaccggactacgtcaccgactcggctgcatcagcaaccgcctggtcaa<br>ccggtgtcaaaacctataaccggcgcgctgggcgtcgatattcacgaaaaagatcacccaacga<br>ttctggaaatggcaaaagccgcaggtctggcgaccggtaacgtttctaccgcagagttgcagg<br>atgccacgcccgctgcgctggtggcacatgtgacctcgcgcaaatgctacggtccgagcgcg<br>accagtgaaaaatgtccgggtaacgctctggaaaaaggcggaaaaggatcgattaccgaaca<br>gctgataacgctcgtgccgacgttacgcttggcggcggcgcaaaaacctttgctgaaacggc<br>aaccgctggtgaatggcagggaaaaacgctgcgtgaacaggcacaggcgcgtggttatcagt<br>tggtgagcgatgctgcctcactgaattcggtgacggaagcgaatcagcaaaaaccctgcttg<br>gcctgtttgctgacggcaatatgccagtgcgctggctaggaccgaaagcaacgtaccatggca<br>atatcgataagcccgcagtcacctgtacgccaaatccgcaacgtaatgacagtgtaccaaccct<br>ggcgcagatgaccgacaaagccattgaattgttgagtaaaaatgagaaaggattttcctgcaa<br>gttgaaggtgcgtcaatcgataaacaggatcatgctgcgaatcctttgtgggcaaattggcgaga<br>cggtcgatctcgatgaagccgtacaacgggcgctggaattcgctaaaaaggagggtaacacg<br>ctggtcatagtcaccgctgatcacgcccacgccagcagattgttgcgccggataccaaagctc<br>cgggcctcacccaggcgctaaataccaaagatggcgcagtgatggtgatgagttacgggaact<br>ccgaagaggattcacaagaacataccggcagtcagttgcgtattgcggcgtatggcccgcatg<br>ccgccaatgttgttggactgaccgaccagaccgatctcttctacaccatgaaagccgctctggg<br>gctgaaa |

Mutations (or substitution) in ClbP peptidase domain are indicated in bold in AA sequence. In the present invention the numbering of amino acids is according to the wild-type ClbP protein sequence (SEQ ID NO: 1).

Method for Treating Gastro-Intestinal Disorder

A second object of the invention relates to the *Escherichia coli* strain Nissle 1917 (EcN) bacterium, as defined above for use as a drug.

A previously indicated EcN was initially studied for its ability to fight bacterial gastrointestinal infections. It was demonstrated to impede intestinal colonization by *Salmonella enterica* serovar *Typhimurium* (3,4) and to exhibit an antibacterial activity against enterohemorrhagic *E. coli* strains (5). EcN is an excellent colonizer of the human gut, and exhibits beneficial effects in various intestinal dysfunctions such as acute diarrhea in infants and toddlers (6), chronic constipation (7), and abdominal pain in patients with irritable bowel syndrome (8). It has been widely used in the treatment of inflammatory bowel diseases (1) and has proven to be as effective as the gold standard mesalazine for the maintenance of remission in ulcerative colitis in children and adults (9). Furthermore, inventors demonstrate in an in vivo animal model infected by a bacterial intestinal pathogen (*S. Typhimurium*) that administration of an EcN modified strain with clbP gene encoding ClbP protein inactive for the peptidase domain (ie. ClbP mutated at position S95), is non-genotoxic (do not produce colibactin) but keeps the bacterial antagonist activity, and reduces colonization and virulence of the pathogen (see FIG. 8) by maintaining the siderophore-microcin production.

Accordingly, the third object of the invention relates to an *Escherichia coli* strain Nissle 1917 (EcN) bacterium, as defined above for in use the treatment of gastrointestinal disease.

Accordingly, another object of the present invention relates to a method of treating gastrointestinal disease in a subject thereof, the method comprising administering the subject a therapeutically effective amount of EcN bacterium of the invention.

Treatment may be for any purpose, including the therapeutic treatment of subjects suffering from pain, as well as the prophylactic treatment of subjects who do not suffer from pain (e.g., subjects identified as being at high risk for gastrointestinal disease). As used herein, the terms "treatment," "treat," and "treating" refer to reversing, alleviating, inhibiting the progress of a disease or disorder as described herein (i.e. gastro-intestinal disease), or delaying, eliminating or reducing the incidence or onset of a disorder or disease as described herein, as compared to that which would occur in the absence of the measure taken. The terms "prophylaxis" or "prophylactic use" and "prophylactic treatment" as used herein, refer to any medical or public health procedure whose purpose is to prevent the disease herein disclosed (i.e. gastro-intestinal disease). As used herein, the terms "prevent", "prevention" and "preventing" refer to the reduction in the risk of acquiring or developing a given condition (i.e. gastro-intestinal disease), or the reduction or inhibition of the recurrence or said condition (i.e. gastrointestinal disease) in a subject who is not ill, but who has been or may be near a subject with the condition (i.e. gastro-intestinal disease)

In a specific *Escherichia coli* strain Nissle 1917 (EcN) bacterium may be used to treat gastrointestinal disease such as bacterial gastrointestinal infection, gut inflammatory disease and visceral pain.

There are a very large number of Bacteria that cause gastrointestinal disease (*E. coli, Salmonella, Shigella, Campylobacter, Clostridium*). Most of the time bacterial infections of the intestines result in diarrhea or dysentery, nausea, vomiting, and abdominal pain or cramping. If the bacterial infection is in the small intestine symptoms include watery diarrhea and/or vomiting. Bacterial infections in the large intestine usually result in dysentery (small fecal volume, with mucus and many times blood). Some diseases follow certain predisposing conditions (antibiotic therapy: pseudomembranous colitis). Not all of these diseases follow infection but can occur following ingestion of preformed toxin (staphylococcal food poisoning). Usually symptoms (vomiting, diarrhea) of intoxication occur soon (few hours) after ingestion of the toxin. There are several ways of categorizing this set of diseases. Some categorize them based on location in the intestines (small vs. large intestine), others by how the disease was acquired (food vs. water vs. person to person), and still others categorize these diseases based on what the infectious agent does to the host (intoxication vs. gastroenteritis vs. noninflammatory diarrhea vs. inflammatory diarrhea vs. enteric fever). All of these means of categorizing these etiologies are used to help the physician narrow down the possible causes of the symptoms. GI tract infections are very common. Diarrhea is the most common cause of death in developing countries (2.5 million deaths/year). Pathogens causing diarrhea can be transmitted to humans in three basic ways: in food, in water, and person to person. Many of these infections are self-limiting and do not require treatment. Some can spread to other sites in the body and require treatment to prevent further damage. The trick is in knowing when to treat and how to treat patients.

In a particular embodiment bacterial gastrointestinal infections are *Salmonella enterica* serovar *Typhimurium* infection or enterohemorrhagic *E. coli* infection.

In a more particular embodiment bacterial gastrointestinal infections are *Salmonella enterica* infection.

In a specific embodiment *Escherichia coli* strain Nissle 1917 (EcN) bacterium may be used to treat gastrointestinal disease such as gut inflammatory diseases. Such gut inflammatory diseases are for instance Inflammatory Bowel Diseases (IBD) or Irritable Bowel Syndrome (IBS).

As used herein, the term "inflammatory bowel diseases (IBD)" is a group of inflammatory diseases of the colon and small intestine.

In particular embodiment Inflammatory Bowel Diseases (IBD), is selected from the group consisting of Crohn's Disease, Ulcerative Colitis Celiac disease, Gluten hypersensitivity and Pouchitis.

As used herein, the term "Irritable Bowel Syndrome (IBS)" is a term for a variety of pathological conditions causing discomfort in the gastro-intestinal tract. It is a functional bowel disorder characterized by chronic abdominal pain, discomfort, bloating, and alteration of bowel habits in the absence of any organic cause. It also includes some forms of food-related visceral hypersensitivity, such as Gluten hypersensitivity (ie. Celiac disease).

Another type of gastrointestinal disease is also visceral pain which includes pain associated with inflammatory bowel disease (IBD). Visceral pain is pain associated with the viscera, which encompasses the organs of the abdominal cavity. These organs include spleen and part of the digestive system. Pain associated with the viscera can be divided into digestive visceral pain and non-digestive visceral pain. Commonly encountered gastrointestinal (GI) disorders inducing pain include functional bowel disorder (FBD) and inflammatory bowel disease (IBD). These GI disorders include a wide range of disease states that are currently only moderately controlled including in respect of FBD-, gastro-oesophageal reflux, dyspepsia, irritable bowel syndrome (IBS) and functional abdominal pain syndrome (FAPS) and—in respect of IBD—Crohn's disease, ileitis and ulcerative colitis, all of which regularly produce visceral pain.

In some embodiments the method of the present invention is particularly suitable for the treatment of visceral pain resulting from gastrointestinal disorders, including functional bowel disorder (FBD) and inflammatory bowel disease (IBD) gastro-oesophageal reflux, dyspepsia, irritable bowel syndrome (IBS) and functional abdominal pain syndrome (FAPS), and, in respect of IBD, Crohn's disease, ileitis, ulcerative colitis dysmenorrhea, cystitis and pancreatitis and pelvic pain.

In a specific embodiment, visceral pain is selected from the group consisting of Inflammatory Bowel Diseases (IBD) or Irritable Bowel Syndrome (IBS).

In some embodiments, the prophylactic methods of the invention are particularly suitable for subjects who are identified as at high risk for pain. Typically subject that are risk for pain include patient that will have a surgical operation.

Said EcN bacterium of the present invention can be used as a drug, in particular as probiotic.

The term "probiotic" has its general meaning in the art and refers to a live microorganisms that, when administered in adequate amounts, confer a health benefit on the host" (see: Clinical Infectious Diseases, Volume 46, Issue Supplement_2, 1 Feb. 2008, Pages S58-S61, https://doi.org/10.1086/523341).

It will be understood that the daily dose of the compounds and the composition of the present invention will be decided by the attending physician within the scope of sound medical judgment. The specific therapeutically effective dose for any particular patient will depend upon a variety of factors including the type and severity of the disorder to treat; activity of the specific compound employed; the specific composition employed, the age, body weight, general health, sex and diet of the patient; the time and route of administration and the rate of excretion of the specific compound employed; the duration of the treatment; drugs used in combination or coincidental with the specific bacterium employed and other factors well known in the medical arts. For example, within the skill of the art it is recommended to start the treatment with doses of the compound at levels lower than those required to achieve the desired therapeutic effect and to gradually increase the dosage until the desired effect is achieved.

The compound of the invention may be administered by any suitable route of administration. For example, the compound according to the invention it can be administered by oral (including buccal and sublingual), rectal, nasal, topical, pulmonary, vaginal, or parenteral (including intramuscular, intra-arterial, intrathecal, subcutaneous and intravenous).

In a preferred embodiment of the invention, the therapeutic composition containing the compound of the invention is administered intrarectally, topically or orally. A rectal administration preferably takes place in the form of a suppository, enema or foam. Intrarectal administration is particularly suitable for intestinal diseases which affect the lower intestinal sections, for example the colon.

Pharmaceutical Composition

The EcN bacterium of the present invention, together with one or more conventional adjuvants, carriers, or diluents may be placed into the form of pharmaceutical compositions and unit dosages.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The pharmaceutical composition and unit dosage forms may comprise conventional ingredients in conventional proportions, with or without additional active compounds or principles, and the unit dosage forms may contain any suitable effective amount of the active ingredients commensurate with the intended daily dosage range to be employed. The pharmaceutical composition may be employed as solids, such as tablets or filled capsules, semisolids, powders, sustained release formulations, or liquids such as solutions, suspensions, emulsions, elixirs, or filled capsules for oral use; or in the form of suppositories for rectal administration; or in the form of sterile injectable solutions for parenteral uses. Formulations containing about one (1) milligram of active ingredient or, more broadly, about 0.01 to about one hundred (100) milligrams, per tablet, are accordingly suitable representative unit dosage forms.

The compound of the present invention may be formulated in a wide variety of oral administration dosage forms. The pharmaceutical compositions and dosage forms may comprise compounds of the present invention or pharmaceutically acceptable salts thereof as the active component. The pharmaceutically acceptable carriers may be either solid or liquid. Solid form preparations include powders, tablets, pulls, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid, which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch gelatin, tragacanth, methylcellulose sodium carboxymethylcellulose, a low melting wax, cocoa butter, and the like.

The term "preparation" is intended to include the formulation of the active compound with an encapsulating material as carrier, providing a capsule in which the active component, with or without carriers, is surrounded by a carrier, which is in association with it. Similarly, cachets and lozenges are included. Tablets, powders, capsules, pulls, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavours, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavours, stabilizers, buffers, artificial and natural sweeteners, dispersants, thickeners, solubilising agents, and the like.

Alternatively, the active ingredient may be in powder form, obtained by aseptic isolation of sterile solid or by lyophilization from solution for constitution before use with a suitable vehicle, e.g., sterile, pyrogen-free water.

The invention will be further illustrated by the following figures and examples. However, these examples and figures should not be interpreted in any way as limiting the scope of the present invention.

FIGURES

Figure 1B:
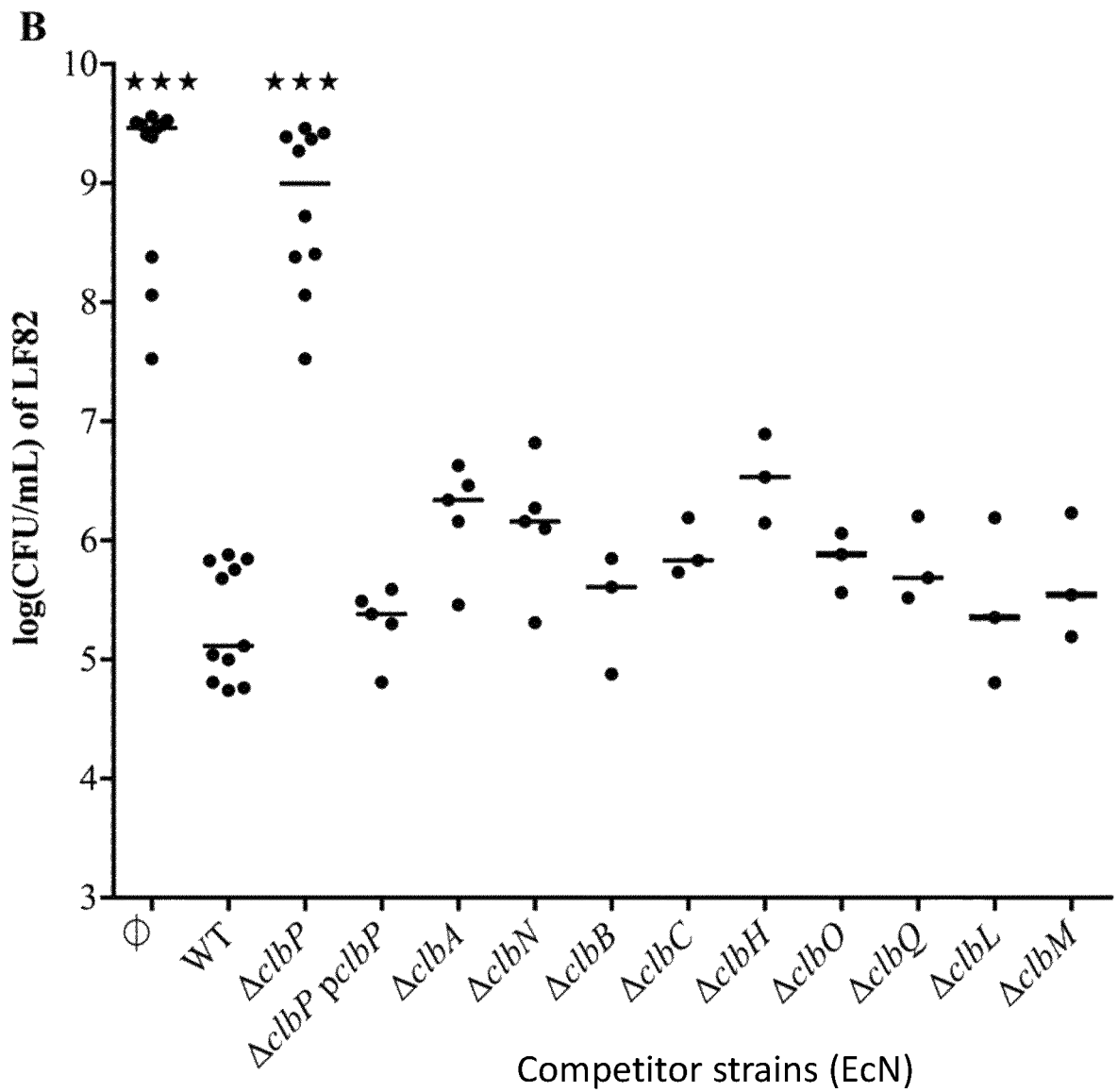

FIG. 1. Role of the pks/clb island in EcN antibacterial activity on LF82. (A) Serial dilutions of 24-hour cocultures of *E. coli* LF82 (rifampicin resistant) with wild-type (WT) *E. coli* strain Nissle 1917 (EcN) or the mutant for the colibactin maturing peptidase ClbP, spotted (10 µL) on LB plate containing rifampicin and incubated overnight at 37° C. (B) Colony forming unit (CFU) counts of *E. coli* LF82 following a 24-hour co-culture in M63 medium with WT EcN, gene deletion for the phosphopantetheinyl transferase ClbA, the peptidase ClbP and the corresponding complemented mutant (pclbP), the polyketide synthases (PKS) ClbC and ClbO, the nonribosomal peptide synthases (NRPS) ClbH and ClbN, the hybrid PKS-NRPS ClbB, the putative amidase ClbL, the efflux pump ClbM, and the thioesterase ClbQ. LF82 was also cultured alone as a control (Ø). The medians and individual results of independent experiments are shown. One-way ANOVA and Bonferroni post-tests in comparison with co-culture with WT; ★★★$P<0.001$.

Figure 2:
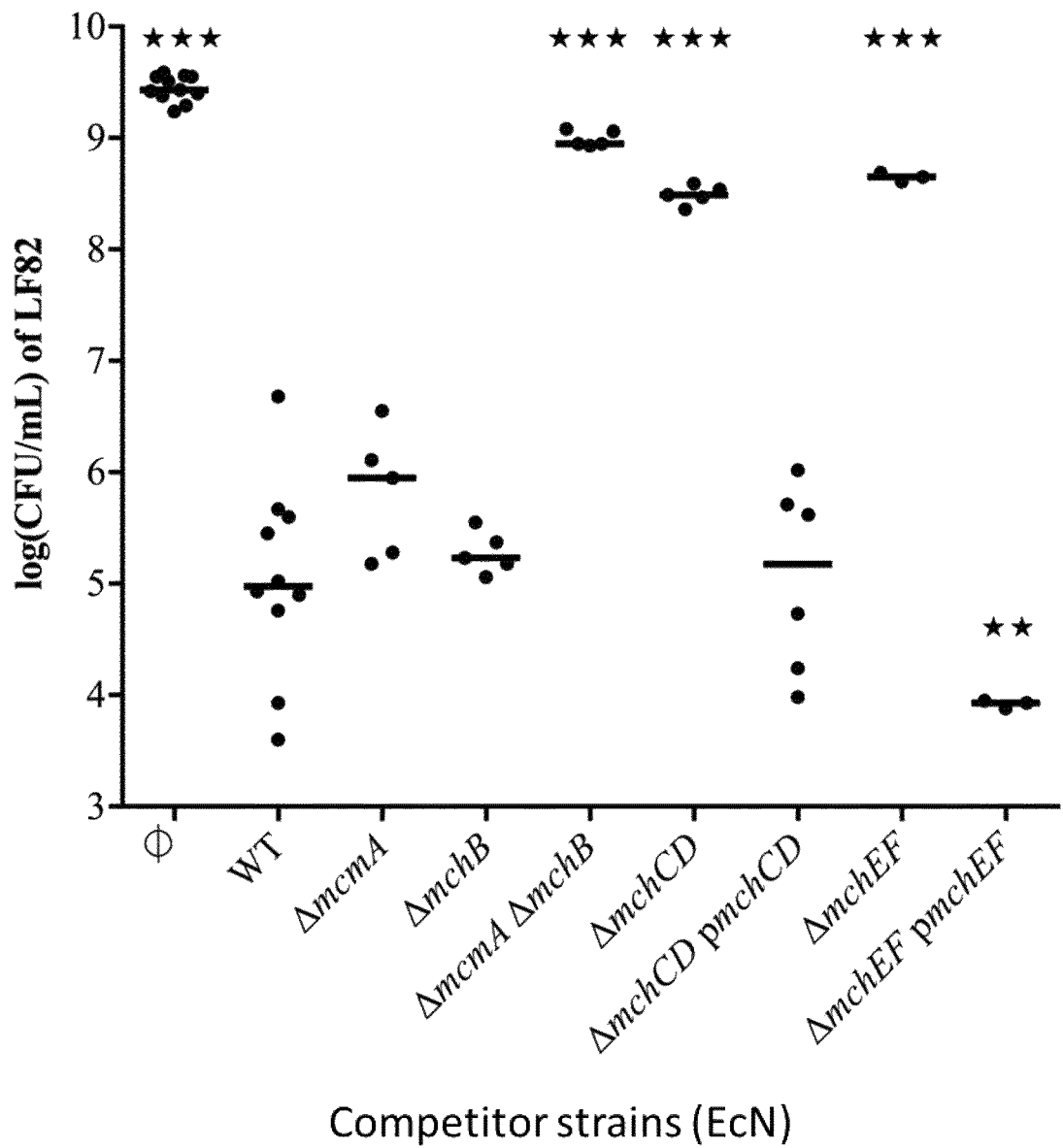

FIG. 2: Role of the microcin gene cluster in EcN antibacterial activity on LF82. Colony forming unit (CFU) counts of *E. coli* LF82 following a 24-hour co-culture in M63 medium with wild-type (WT) *E. coli* strain Nissle 1917 (EcN), EcN mutant for microcin M (MccM) precursor gene mcmA, for microcin H47 (MccH47) precursor gene mchB, for both mcmA mchB genes; EcN mutants and complemented strains for mchC mchD genes responsible for post-translational modifications, and for mchE mchF genes that encode the MccM and MccH47 efflux pump. LF82 was also cultured alone as a control (Ø). The medians and individual results of independent experiments are shown. One-way ANOVA and Bonferroni post-tests in comparison with co-culture with WT; ★★$0.001<P<0.01$; ★★★$P<0.001$.

Figure 3:
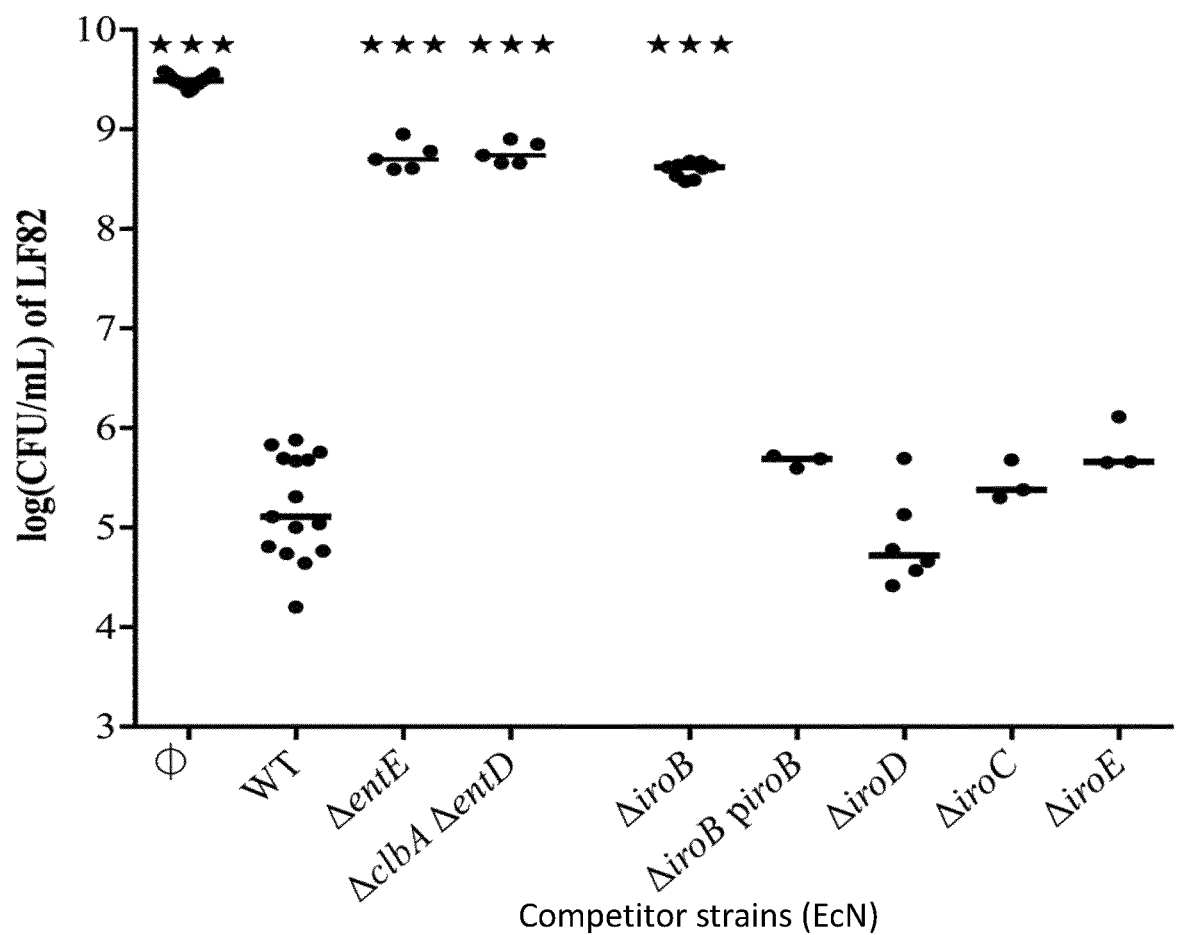

FIG. 3: Role of siderophores in EcN antibacterial activity on LF82. (A) Colony forming unit (CFU) counts of *E. coli* LF82 following a 24-hour co-culture in M63 medium with wild-type (WT) *E. coli* strain Nissle 1917 (EcN), EcN mutant for entE that encodes the enterobactin synthase E, and the double mutant for the phosphopantetheinyl transferases ClbA and EntD; EcN mutant and complemented strain for the glucosyltransferase IroB, the cytoplasmic esterase IroD, the periplasmic esterase IroE, and the export protein IroC. LF82 was also cultured alone as a control (Ø). The medians and individual results of independent experiments are shown. One way ANOVA and Bonferroni post-tests in comparison with co-culture with WT; ★★★$P<0.001$.

Figure 4:
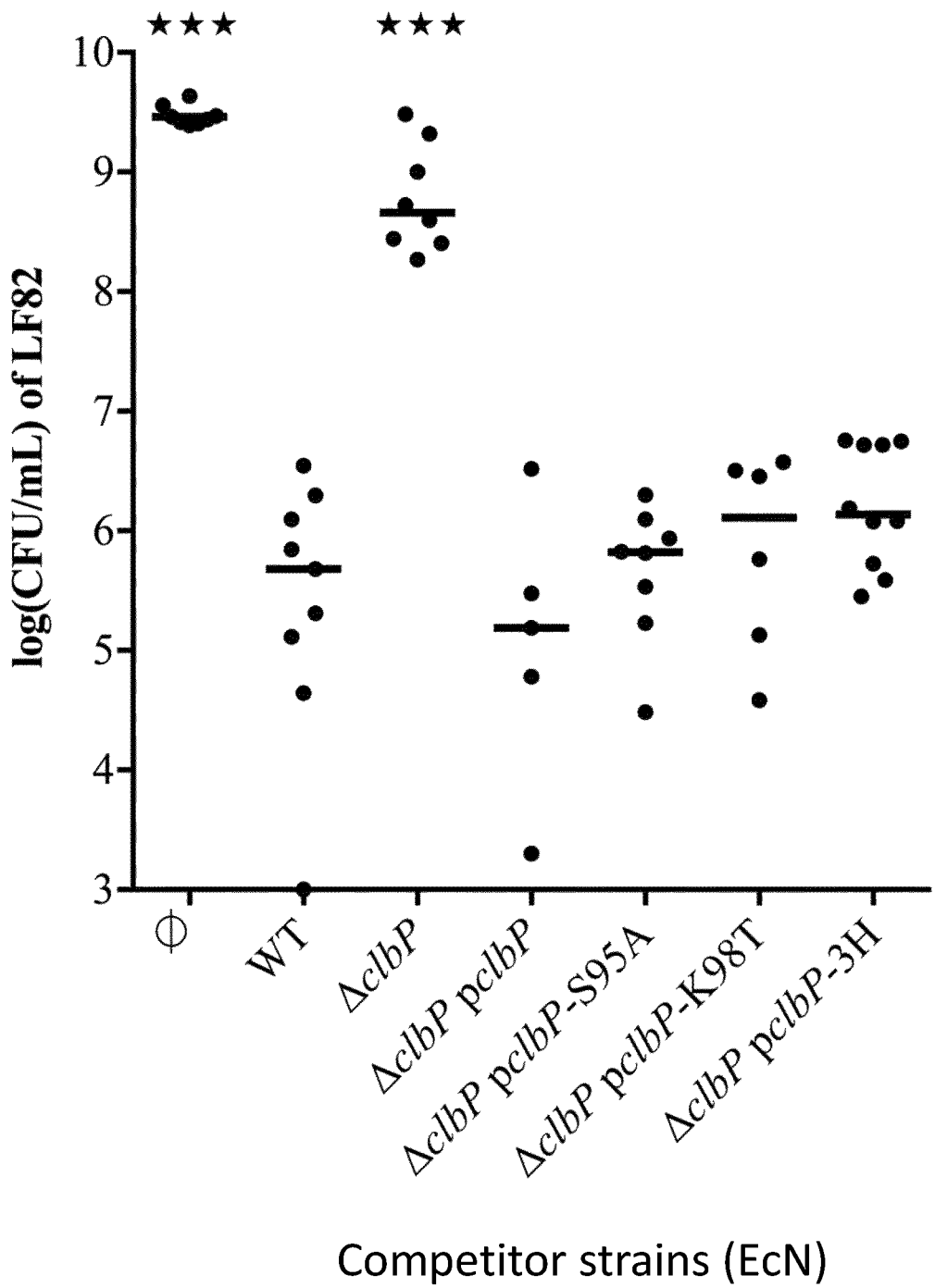

FIG. 4: Role of ClbP catalytic and transmembrane domains in EcN antibacterial activity on LF82.

Colony forming unit (CFU) counts of *E. coli* LF82 following a 24-hour co-culture in M63 medium with wild-type (WT) *E. coli* strain Nissle 1917 (EcN), the clbP gene deletion and complemented mutant with a plasmid that encodes wild-type ClbP (pclbP), plasmids that encode ClbP with a mutation S95A or K98T in the catalytic site, and a plasmid that encodes a fusion between the alkaline phosphatase PhoA and the ClbP C-terminal sequence from amino-acid 390 (pclbP-3H). LF82 was also cultured alone as a control (Ø). Medians and individual results of independent experiments are shown. One way ANOVA and Bonferroni post-tests in comparison with co-culture with WT; ★★★P<0.001.

Figure 5A:
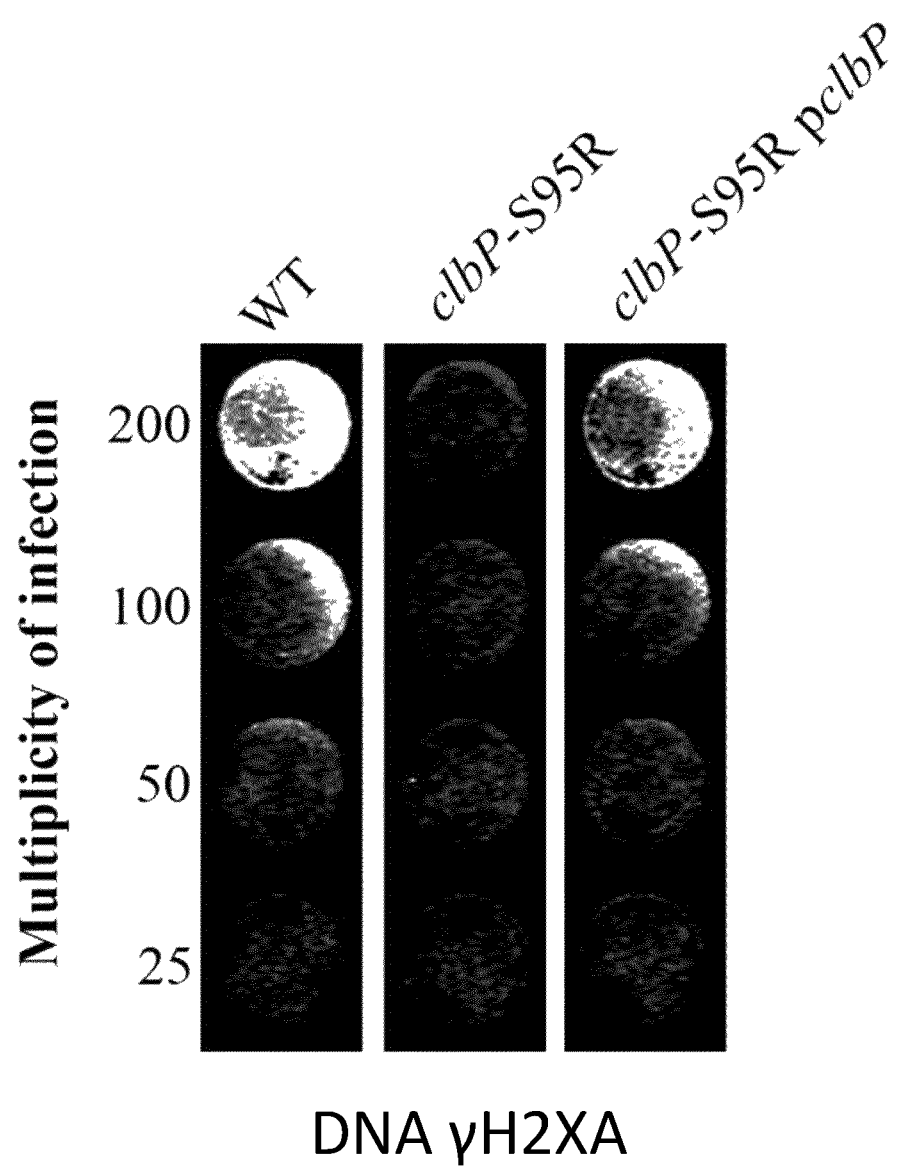
Figure 5B:
Figure 5C:
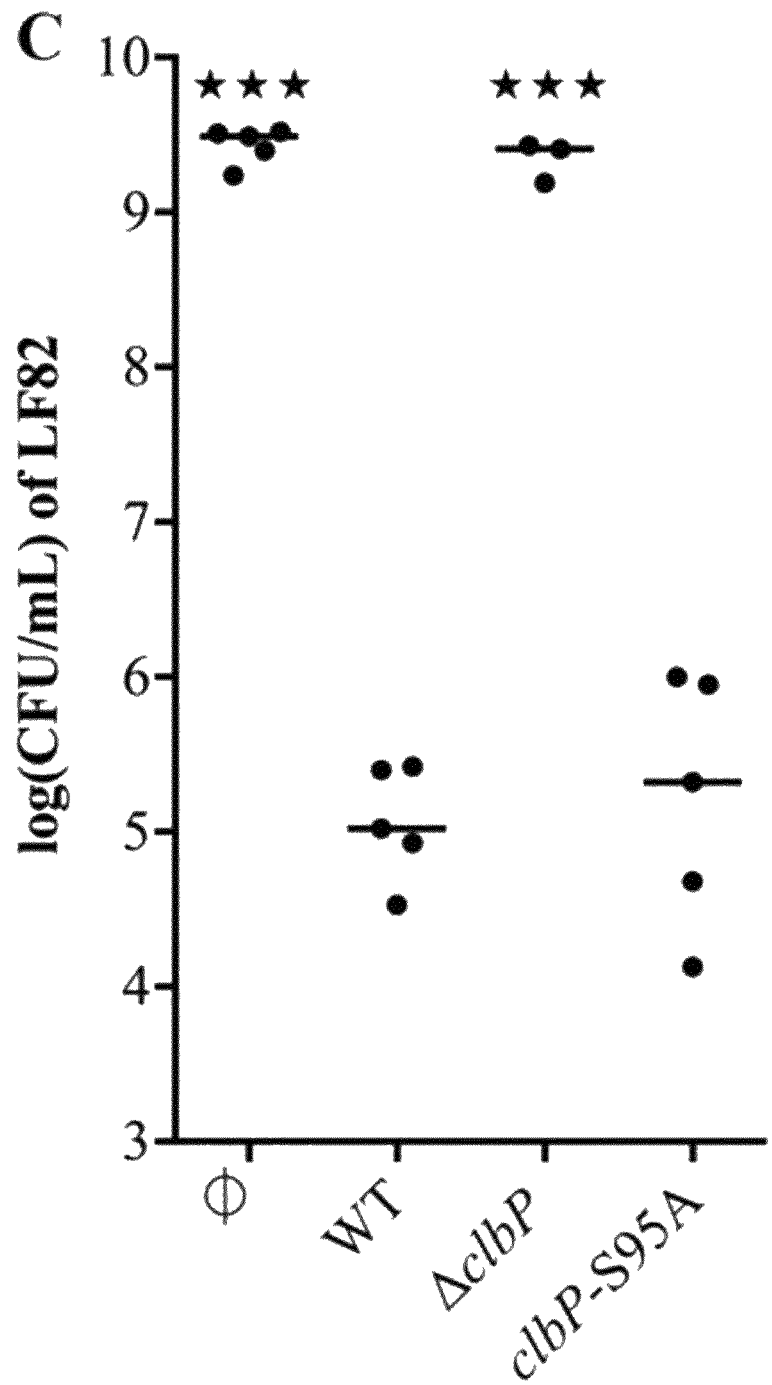

FIG. 5: A genomic point mutation that inactivates ClbP catalytic domain abrogates EcN genotoxicity but not the antibacterial activity on LF82. (A) HeLa cells were transiently infected with wild-type E. coli Nissle (WT), a genome edited mutant with a single chromosomal nucleotide change in the clbP gene that inactivates the catalytic site (clbP-S95R), and the genome edited mutant complemented with the plasmid pclbP. Cells were then fixed, permeabilized and stained with rabbit monoclonal anti-gamma-H2AX followed by an infrared fluorescent secondary antibody. DNA was counterstained with RedDot2. (B) HeLa cells were transiently infected with wild-type E. coli Nissle (photo B), a clbP gene deletion mutant (C), and the genome edited clbP-S95R mutant (D). These cells were then washed and incubated with gentamicin for 72 hours before staining with Giemsa. The control is shown in photo A. Bars represent 50 (C) Colony forming unit (CFU) counts of E. coli LF82 following a 24-hour co-culture in M63 medium with wild-type (WT) E. coli strain Nissle 1917 (EcN), the clbP gene deletion mutant (ΔclbP), and the genome edited mutant with a single nucleotide change in the clbP gene that results in an S95R mutation in the catalytic site (clbP-S95R). LF82 was also cultured alone as a control (Ø). Medians and individual results of independent experiments are shown. One way ANOVA and Bonferroni post-tests in comparison with co-culture with WT; ★★★P<0.001

Figure 6:
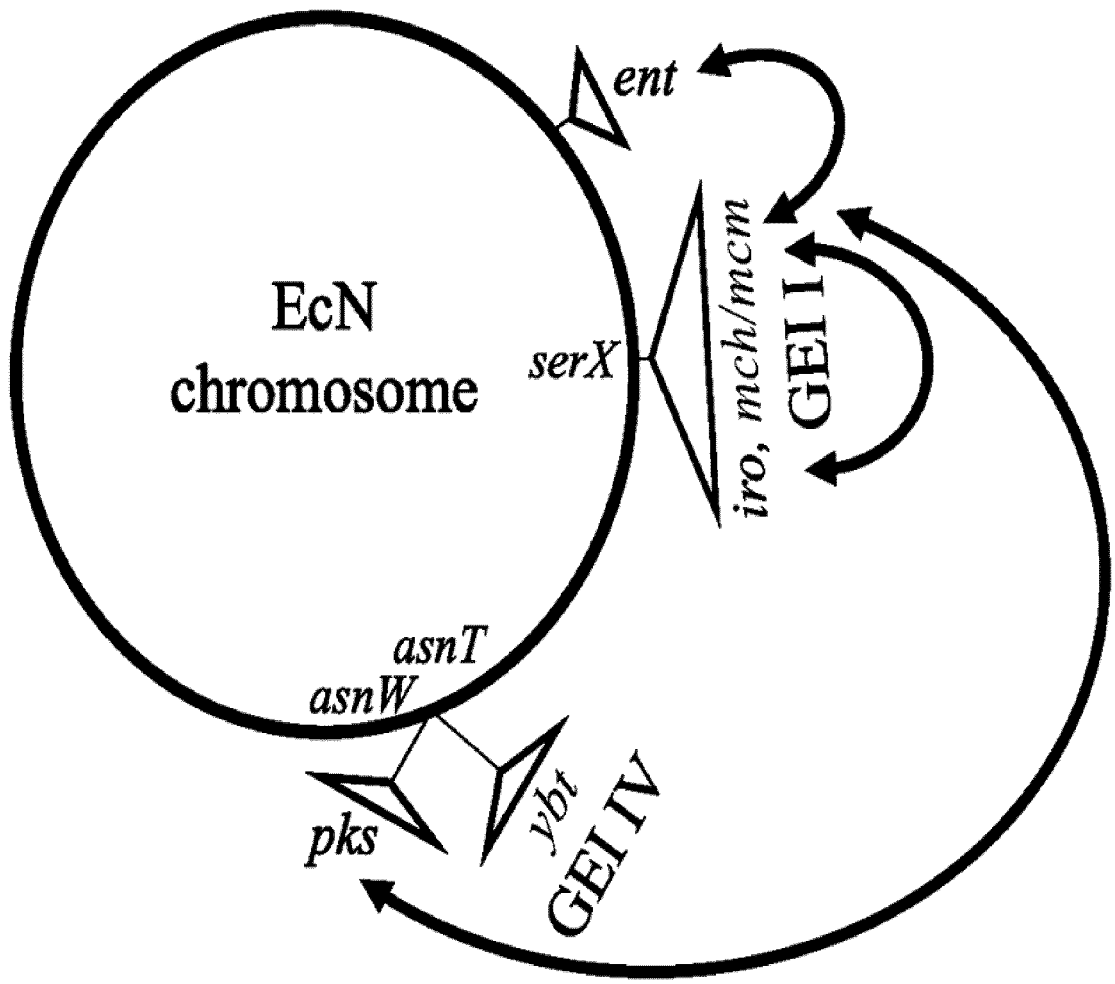

FIG. 6: Gene clusters involved in the production of microcins H47 and M (MccH47 and M) in E. coli strain Nissle (EcN) represented on a genomic map. The loci that encode enterobactin (ent), colibactin (pks), yersiniabactin (ybt) on EcN genomic island (GEI) IV, salmochelin (iro) and MccH47 (mch) and M (mcm) on GEI I are represented. The arrows represent the interplays between the different gene clusters involved in MccH47 and M production in EcN.

Figure 7:
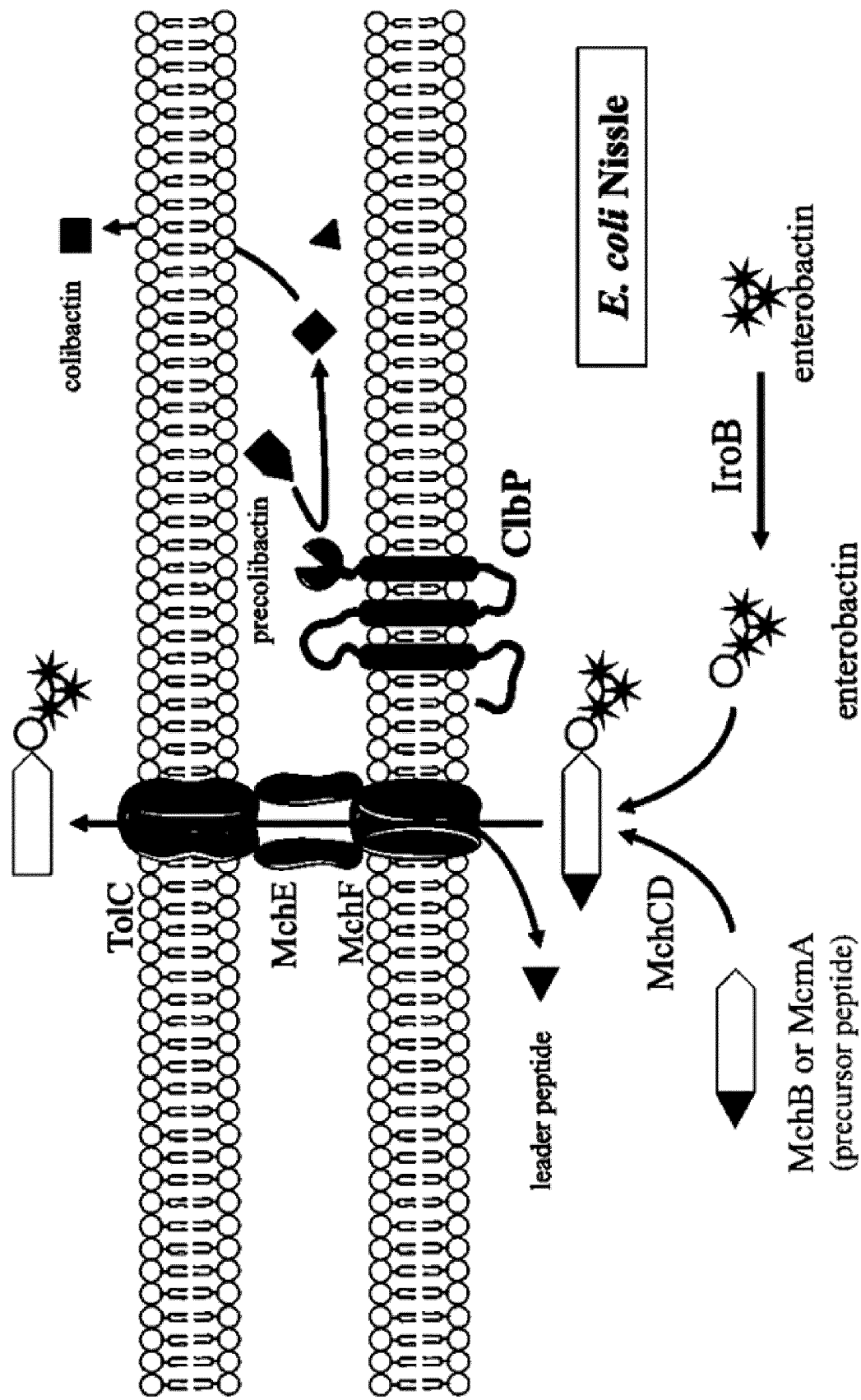

FIG. 7: Model proposed for biosynthesis of siderophore-microcins H47 and M in E. coli Nissle. An enterobactin precursor is modified by the enterobactin glucosyltransferase IroB. This siderophore moiety is transferred onto the C-terminal extremity of the precursor peptide by the MchCD complex. The active form of the siderophore-microcin is the result of the leader peptide cleavage during its export by the specific efflux pump MchEF-TolC. The C-terminal domain of ClbP allows this final step of siderophore-microcin production, while its N-terminal enzymatic domain cleaves precolibactin to produce colibactin.

FIG. 8: A clbP deletion, but not a genomic point mutation that inactivates ClbP catalytic domain, impairs EcN protection against the enteric pathogen Salmonella Typhimurium in mice.

C57BL/6 female mice were treated with 20 mg streptomycin per os, then 24 h later infected orally with $10^9$ S. Typhimurium (STm) in PBS or co-administered with $10^9$ S. Typhimurium and $10^9$ EcN wild-type, ΔclbP or clbPS95R strains. (A) The mice were monitored for clinical signs (weight loss, diarrhea, signs of abdominal pain) daily during 4 days. Each point corresponds to the mean clinical score+/− SEM of 10 to 15 animals per group in three independent experiment. The animals were scored blindly (without knowledge of the infecting bacteria) in the last two of the three experiments. Two way ANOVA with Bonferonni post-test compared to STm+EcN, a: p<0.05, c: p<0.001. (B) The fecal shedding of STm was examined by enumeration of the feces collected at day 2 and 4 after infection. The median and individual result are shown. One way ANOVA of log-transformed CFU counts compared to STm+PBS, a: p<0.05 (C) Fecal counts of STm and EcN were used to determine the competitive index (CFU STm/CFU EcN). One way ANOVA compared to STm+EcN clbPS95R, a: p<0.05.

Figure 9:
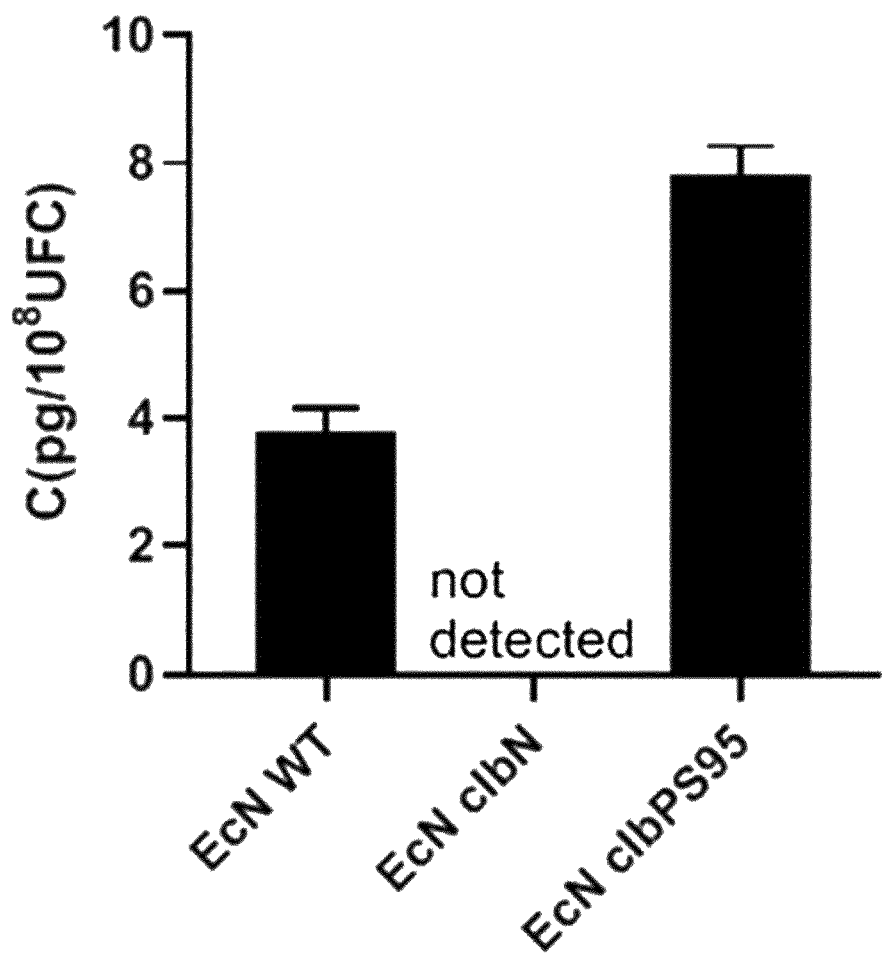

FIG. 9: Detection of N-acyl-Asn-GABAOH in EcN wild-type, ΔclbN and clbPS95R strains.

EcN wild-type, ΔclbN or clbPS95R strains were grown 8 hours in DMEM Hepes then N-acyl-Asn-GABAOH was quantified in bacterial pellets by high-performance liquid chromatography (Agilent 1290 Infinity) coupled to a triple quadrupole mass spectrometer (G6460 Agilent). The concentration C is shown as picogram per 1E+8 CFU).

EXAMPLE

Material & Methods
Bacterial Strains, Mutants and Plasmids

The bacterial strains and plasmids used in this study are listed in Table 3. Gene mutagenesis was performed by the lambda Red recombinase method (37). The double mutants were constructed sequentially. The mutations and deletion of FRT cassettes were verified by PCR using primers upstream and downstream of the target genes.

The fusion between ClbP N-terminal signal sequence, the alkaline phosphatase PhoA, and the three transmembrane helices of ClbP were constructed using the HiFi DNA assembly kit (New England Biolabs, Ipswich, MA, USA) with primers overlapping between each fragment. The constructions were verified by PCR and confirmed by sequencing. The blue-stained colony-forming units on LB plates with 40 mg/L of 5-bromo-4-chloro-3-indolyl phosphate revealed the presence of the PhoA alkaline phosphatase domain in the periplasm as previously reported (38).

To construct plasmids pmchEF and pmchCD, the genes were PCR-amplified and cloned into pCR-XL-TOPO (Invitrogen, Carlsbad, CA, USA).

To construct plasmid pIroB, the iroB gene was PCR-amplified with EcN genomic DNA as a template and primers IRSDNG7 and IRSDNG8, digested by EcoRI and BamHI and ligated into pBbA5a-RFP (obtained from Addgene) digested to remove the rfp gene.

The strain EcN clbP-S595R chromosomal isogenic mutant was constructed using a genome editing technique (39). EcN was transformed with pORTMAGE, then grown in LB at 30° C. and 300 rpm to reach OD600=0.5. An initial mutagenesis cycle was started by inducing the expression of Lambda recombinases and the dominant negative mutLE32K allele at 42° C. for 15 minutes at 250 rpm. The culture was then cooled to 0° C., washed in water and electroporated with 50 μM of oligonucleotide IRSDNG26 that includes the S95A mutation in the clbP gene sequence. In a control experiment, the lacZ gene was targeted by a specific mutagenic oligonucleotide. Following recovery in LB at 30° C. and 300 rpm for 1 hour, two other mutagenesis cycles were performed, and the bacteria were finally plated on MacConkey agar without any antibiotic. Approximately 33% of the isolates were LacZ negative in the control experiment. Sixty candidate clbP-S595R mutants were tested for loss of genotoxicity and megalocytosis phenotype in infected HeLa cells as previously described (40). Non genotoxic mutants that had lost the pORTMAGE plasmid were selected, and were finally verified for removal of a ClaI restriction site by S95A mutation in the PCR amplified clbP sequence.

Determination of the Genotoxic Effect Induced by Colibactin

The cellular senescence induced by colibactin was with the associated cell enlargement called megalocytosis and was determined for every EcN mutant constructed in this study in the Mcc gene cluster, in the iroA locus, and for the clbP-S95R mutant. As previously described (40), HeLa cells (ATCC, CCL-2) were infected for 4 hours. The cells were then washed and incubated with gentamicin for 72 hours before staining with Giemsa. The genotoxicity of EcN and the clbP-S95R chromosomal mutant was confirmed by an In-Cell Western procedure, as previously described (36). In brief, HeLa cells were infected in 96-well plates for 4 hours at a given multiplicity of infection (number of bacteria per cell at the onset of infection). Four hours after the end of infection cells were fixed, permeabilized and stained with rabbit monoclonal anti-gamma-H2AX (Cell Signaling, 20E4, 1:200) followed by an infrared fluorescent secondary antibody. DNA was counterstained with RedDot2 (Biotum). Fluorescence was recorded with an Odyssey infrared imaging system (Li-Cor).

Competitive Growth Assay

Strains were grown in lysogeny broth (LB Lennox, Invitrogen) overnight at 37° C. with shaking at 240 rpm. Rifampicin, streptomycin, kanamycin, carbenicillin or chloramphenicol was added as required to the medium.

The media used for co-culture experiments were either M63 minimal medium with final concentrations of 15 mM ammonium sulfate, 1 mM magnesium sulfate heptahydrate, 100 mM monopotassic phosphate, 2.5 g/L glucose, 1 mg/L thiamine, and 1 g/L Bacto tryptone (BD Biosciences, Le Pont de Claix, France), or Dulbecco's Modified Eagle Medium (DMEM) GlutaMAX (Invitrogen) supplemented with 25 mM Hepes, 10% (v/v) Fetal Calf Serum (FCS, Eurobio, Courtaboeuf, France), and 1% (v/v) Non Essential Amino Acids (NEAA, Invitrogen).

500 µL of each overnight culture were cultured in 9.5 mL of co-culture medium and incubated for 2h at 37° C. with shaking at 240 rpm. Both the producing and the target strains (EcN and LF82 respectively) were inoculated from these 2-hour-cultures at 106 CFU/mL in 10 mL of co-culture medium as previously described (3) and incubated for 24 h at 37° C. with shaking at 240 rpm. For CFU numeration, the culture broth was serial-diluted in PBS and plated on selective LB agar plates containing the antibiotic required (e.g. rifampicin for LF82 (41)). In the total results section, only the growth of the target strains (mainly LF82) is reported. As a control, the growth of the competitive strains (mainly EcN and EcN mutants) was systematically checked (data not shown).

Animal Infections

The animal infections were performed following the European directives for the protection of animal used for scientific purposes (2010/63/EU). The protocol was approved by a local ethic committee (number of protocol: 2019041710292271). Female C57BL/6 (Janvier) were housed in ventilated cages, 5 animals per cage, with ad libitum access to food and water.

The animals were administered by oral gavage 20 mg of streptomycin, then 24 h later, infected per os with $10^9$ S. Typhimurium strain IR715 (nalidixic acid resistant) or co-administered with $10^9$ S. Typhimurium and $10^9$ EcN, EcN ΔclbP or EcN clbPS95R (with the rpsLK42R allele to confer resistance to streptomycin).

Fecal shedding of S. Typhimurium and EcN was determined by homogenization of feces in PBS, serial dilution and plating on LB agar plates supplemented with nalidixic acid or streptomycin.

The severity of the salmonellosis was evaluated by daily scoring of weight loss, signs of abdominal pain, fever and diarrhea.

The experiment was terminated at 4 days after infection to avoid lethality.

The experiment was repeated three times with five animals per group, and the clinical score was scored blindly (without knowledge of the infecting bacteria) in two out of the three independent experiments.

Bioinformatic Analysis

Genes involved in McCH47 and MccM synthesis were searched using BLASTn and the CA58 Mcc gene cluster as a reference: mchB and mcmA which encode precursor proteins, the immunity genes mchI and mcmI, genes mchE and mchF which encode a specific efflux pump, and genes mcmK and mcmL (and their respective homologs in the E. coli H47 Mcc gene cluster, mchS1 and mchA) responsible for posttranslational modifications. A query cover >80%, an identity >90%, and an E value <1e 40 were chosen as cutoff values for significance. The genes clbB and clbP, as respective markers for the 5' and 3' regions of the pks island, were identified using the same method, and so were genes iroN and iroB as markers for the 5' and 3' regions of the salmochelin gene cluster (iroA locus). Phylogroups were determined in silico based on the presence/absence of 4 genes: arpA, chuA, yjaA, and tspE4.C2 (and trpA to distinguish the A and C phylogroups) (42). The phylogenetic tree was constructed with the rpoC sequence. The sequences were collected using PATRIC 3.5.8 (43), aligned by multiple sequence comparison by log expectation (MUSCLE) with the MEGA7.0.26 software (44), and the phylogenetic tree was constructed according to the maximum likelihood method with MEGA7.0.26.

Statistical Analyses

Statistical analyses were carried out using GraphPad Prism 7.0a (GraphPad, San Diego, CA, USA). P values were calculated using one-way ANOVA followed by Bonferroni post-tests. CFU/ml were log-transformed for the analyses. P values <0.05 were considered significant and are denoted by ★, P<0.01 is denoted by ★★, and P<0.001 by ★★★.

Results

EcN Antibacterial Activity Requires ClbP but not the Other Components of the Colibactin Synthesis Pathway In order to specifically decouple the genotoxic activity from the probiotic activity, we tested the antibacterial activity of the EcN mutant deleted for ClbP that allows the maturation of precolibactin in genotoxic colibactin (24,25). We compared it to the pleiotropic ClbA mutant coding for a PPTase (27,35,36). We performed co-culture experiments with the wild-type EcN, the EcN ΔclbA and ΔclbP mutants, and the Crohn's disease-associated E. coli strain LF82 which have been previously shown to be susceptible to EcN (45,46). CFU showed that the EcN strain strongly inhibited LF82 growth. EcN antibacterial activity on LF82 was not altered in a ΔclbA mutant but was completely lost in a ΔclbP mutant (FIG. 1). A kinetic experiment indicated that EcN inhibitory activity on LF82 started 6 hours post-inoculation and reached its maximum 8 hours post-inoculation, at the beginning of the stationary phase (data not shown). LF82 growth was not altered at any time by the ΔclbP mutant, further proving the ClbP-dependence of the EcN antibacterial effect. This EcN ClbP-dependent inhibitory activity was also observed with other pathogenic strains of *E. coli* (JJ186 and NRG857c) and closely related bacteria species, such as *Salmonella enterica* subsp. *enterica* Typhimurium, and *Enterobacter aerogenes* (data not shown).

To further determine whether other components of the colibactin synthesis pathway besides ClbP are required for EcN antibacterial activity, the inhibitory effect of mutants for the PKS ClbC and ClbO, the NRPS ClbH and ClbN, the hybrid PKS-NRPS ClbB, the putative amidase ClbL, the efflux pump ClbM, and the thioesterase ClbQ were assessed against LF82. EcN antibacterial activity against LF82 was not altered in any of these mutants (FIG. 1). These results confirm that colibactin itself or the cleavage product N-myristoyl-D-asparagine is not essential for EcN antibacterial activity against LF82 (and other Gram-negative bacteria, data not shown). Therefore, the probiotic activities of EcN are clearly associated with the presence of the pks/clb island and ClbP but not colibactin is involved in EcN inhibitory activity.

EcN ClbP-Dependent Antibacterial Activity Requires MccH47 and MccM

Previous studies have associated EcN antibacterial activity with MccH47 and MccM (4,11,14,15). Therefore, we performed co-culture experiments with LF82, EcN and mutants in MccH47 and MccM production systems. EcN antibacterial activity against LF82 was not affected by the deletion of the MccM precursor gene mcmA alone or the MccH47 precursor gene mchB alone (FIG. 2). In contrast, deletions of both mcmA and mchB almost completely abrogated the inhibitory effect of EcN on LF82. Similarly, deletion of the MccM and MccH47 efflux pump encoding genes mchE and mchF resulted in a loss of antibacterial activity (FIG. 2). The trans-complementation of mchE and mchF increased EcN inhibitory activity compared to the wild-type EcN strain (FIG. 2), probably because of an increase in Mcc export following overexpression of the MchE-MchF efflux pump. None of these mutations in the Mcc production system affected the ability of EcN to produce active colibactin (data not shown).

To further confirm the role of MccH47 and MccM in EcN antibacterial activity, plasmids that encode MccH47 or MccM immunity genes were transformed in LF82, and the resulting resistance of the strains was assessed against EcN (data not shown). EcN ΔmchB mutant antibacterial activity was almost completely abrogated on LF82 that carries the MccM immunity gene mcmI (data not shown). A similar result was obtained with the ΔmcmA mutant and LF82 that carries MccH47 immunity gene mchI (data not shown). Overall, these results confirmed that the EcN ClbP-dependent inhibitory activity against LF82 is due to MccH47 and MccM.

EcN ClbP-Dependent Antibacterial Activity is Due to the Production of Siderophore-Mcc MccH47 and MccM can be modified posttranslationally by the linkage of a catechol siderophore to form a "siderophore-Mcc" (13). Therefore, we hypothesized that the ClbP-dependent antibacterial activity might be dependent on these modified forms of microcins. In fact, EcN antibacterial activity against LF82 was strongly reduced in a ΔentE mutant deprived of the enzyme 2,3-dihydroxybenzoate-AMP ligase essential for siderophore enterobactin production (47). Similar results were obtained with the EcN ΔclbA ΔentD double mutant which was unable to produce enterobactin (36) (FIG. 3).

The two genes responsible for enterobactin glycosylation and esterification (mcmL and mcmK) are missing from the EcN Mcc gene cluster (18,48). As a result, whether MccH47 and MccM are siderophore-Mcc or unmodified Mcc is still being debated (13). Considering that EcN carries the McmL and McmK homologs, glucosyltransferase IroB and esterase IroD respectively (13), we investigated the interplay between the Mcc and the salmochelin production systems. The antibacterial activity of EcN mutants for genes that encode the glucosyltransferase IroB, the cytoplasmic esterase IroD, the periplasmic esterase IroE, and the export protein IroC (49,50) was compared to the activity of the wild-type EcN strain. Only iroB deletion led to a significant decrease in EcN antibacterial activity (FIG. 3). Complementation of the ΔiroB mutant fully restored the antibacterial activity. None of these mutations in the iroA locus affected EcN ability to cause megalocytosis linked with the colibactin genotoxic effect (data not shown). These results suggest that IroB could be responsible for enterobactin glycosylation, which enables the linkage of Mcc precursor proteins to the siderophore-derived moiety in the absence of McmL.

MchC and MchD are respective homologous to MceJ and MceI of *K. pneumoniae* strain E492 (13). These proteins form a complex responsible for the linkage of glycosylated enterobactin derivatives to MccE492 the precursor peptide McrA (51). The EcN mutant for mchC and mchD lost the antibacterial effect against LF82, whereas complementation restored the initial phenotype (FIG. 2). These results indicate that the posttranslational modification of MccH47 and MccM with an enterobactin-derived moiety is required for EcN antibacterial activity. In short, EcN ClbP-dependent antibacterial activity is due to siderophore-Mcc.

The ClbP Transmembrane Domain, Rather Than the Periplasmic Peptidase Catalytic Site, is Required for the Antibacterial Activity of EcN To further elucidate the role of ClbP in siderophore-Mcc production, we examined whether ClbP catalytic activity is required for EcN antibacterial activity. S95 and K98 are key residues for ClbP peptidase activity, and mutants for these residues fail to cleave precolibactin to release mature active genotoxin (24,25). Co-culture experiments were performed with LF82 and the EcN ΔclbP mutant complemented with plasmids that encode the wild-type ClbP protein, or the ClbP protein that harbors the substitutions S95A or K98T. EcN ΔclbP mutants complemented with ClbP S95A or K98T demonstrated antibacterial activities similar to those of the wild-type ClbP protein (FIG. 4), whereas they lost their ability to cause megalocytosis linked with the colibactin genotoxic effect (data not shown).

To exclude the role of another putative catalytic site of ClbP enzymatic domain, this enzymatic domain was replaced by alkaline phosphatase enzymatic domain of PhoA, as previously reported (38). The PhoA domain was fused with the ClbP N-terminal signal sequence which allows the translocation to periplasm, and the ClbP C-terminal sequence from amino-acid 390; the residues forming the three transmembrane helices being 390-412, 433-455, and 465-485 (24). An EcN ΔclbP mutant transformed with a plasmid bearing this fusion demonstrated a similar inhibitory activity against LF82 as the EcN WT strain (FIG. 4), whereas it did not cause megalocytosis (data not shown). Therefore, the C-terminal domain of ClbP that comprises the three transmembrane helices is essential for EcN antibacterial activity, as opposed to the ClbP periplasmic peptidase domain which is crucial only for genotoxic activity.

To confirm this observation, and as a proof of the concept that a non-genotoxic EcN probiotic strain could be engineered, we used genome editing to construct an EcN mutant strain that exhibits a single nucleotide mutation in the chromosomic clbP gene, which leads to an S95R mutation in the ClbP catalytic site at the amino-acid level. This mutant did not produce colibactin and is not genotoxic but still exhibited an antibacterial activity towards LF82 that is similar to that of the wild-type genotoxic EcN strain (FIG. 5).

Figure 8A:
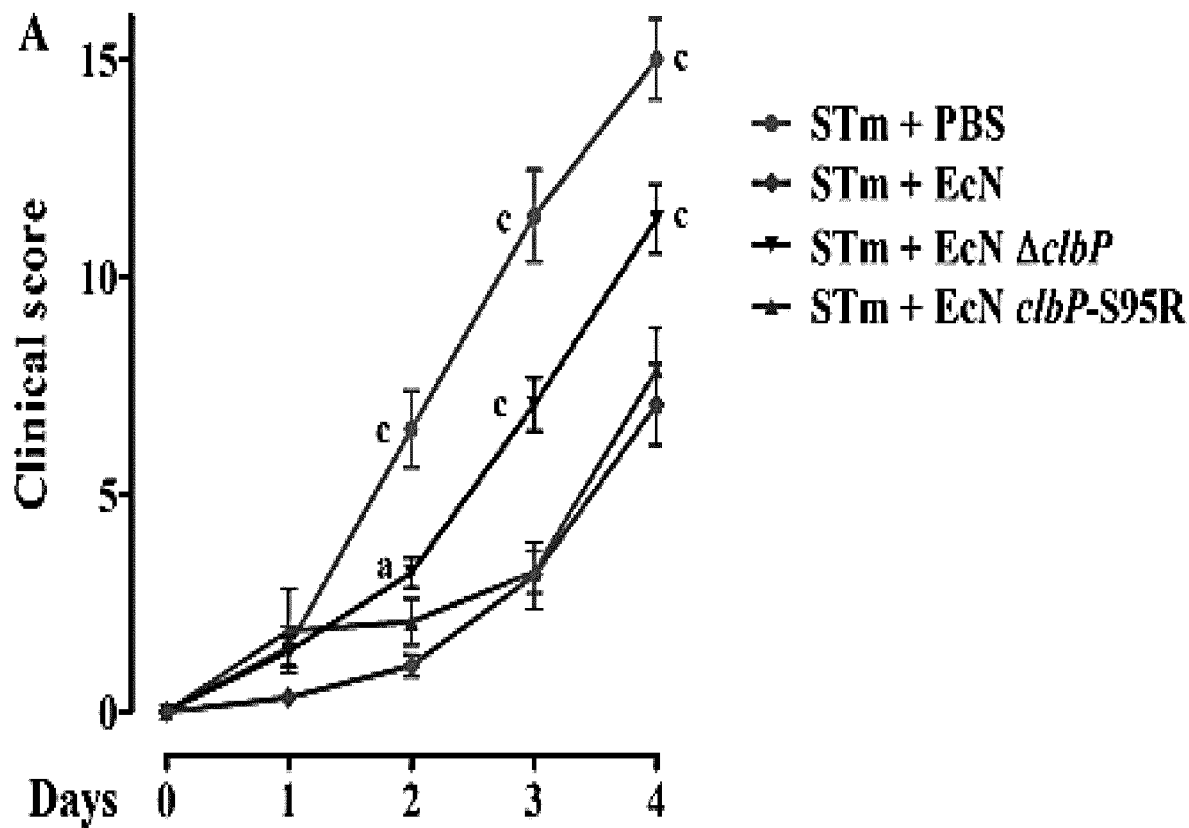
Figure 8B:
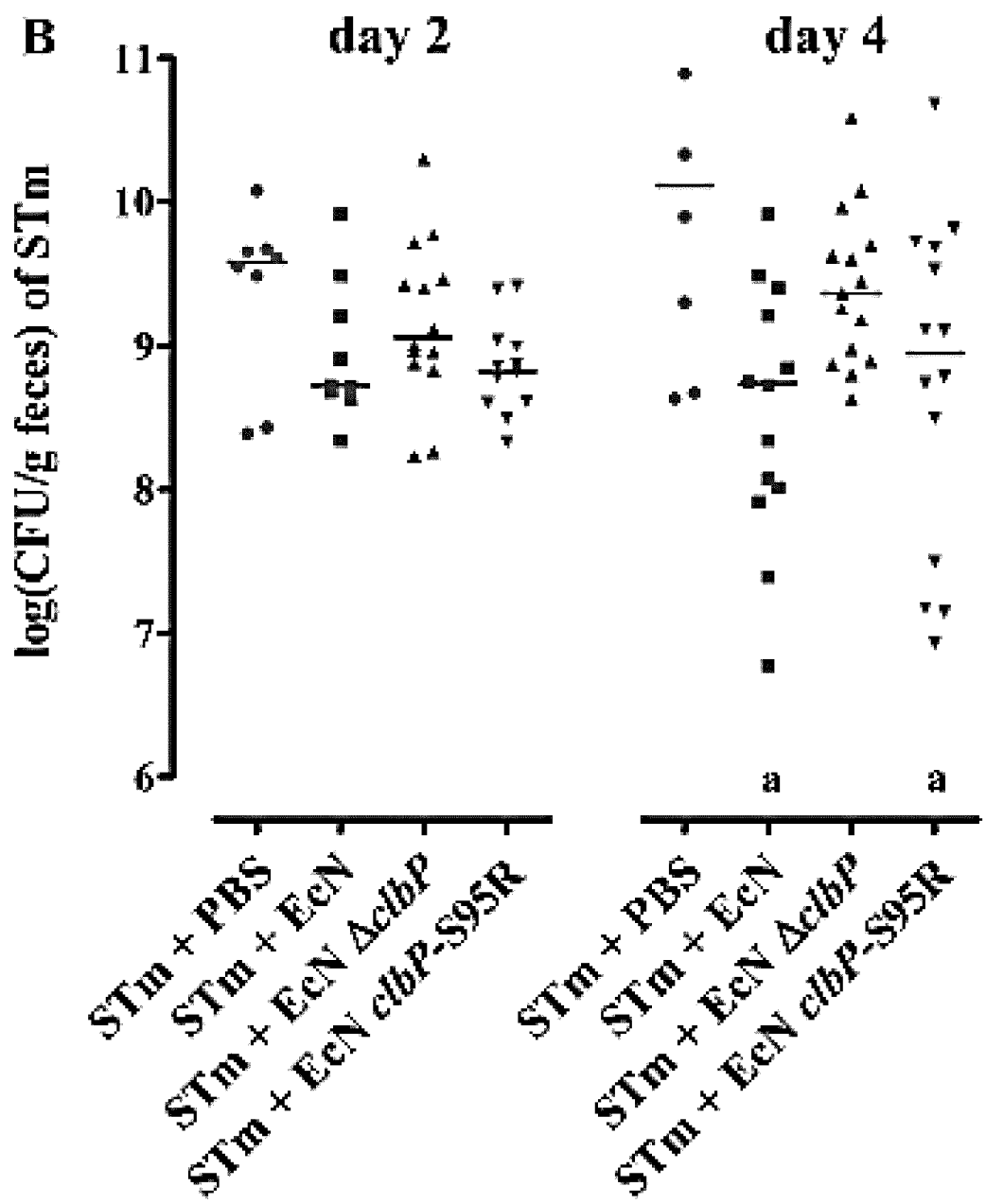
Figure 8C:
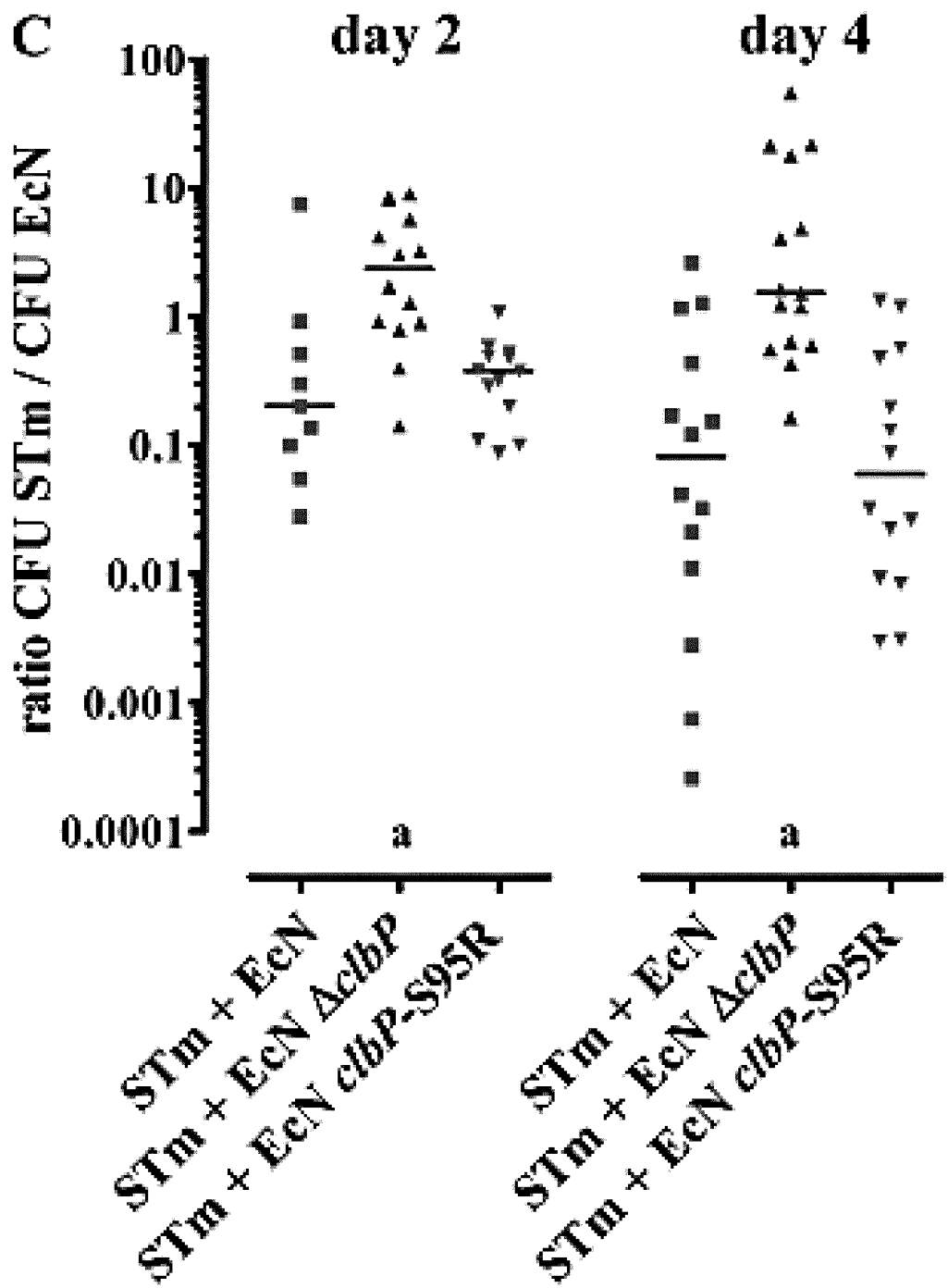

An EcN Strain with a Point Mutation in the clbP Gene is Non-Genotoxic but Keeps the Antagonist Activity, and Reduces S. Typhimurium Intestinal Colonization and Virulence The EcN probiotic is well known to offer protection against enteric pathogens such as Salmonella, by competing for iron and producing the siderophore-microcins (3,4). Thus, we examined whether the EcN wild-type, ΔclbP and clbP-S95R mutants reduces S. Typhimurium intestinal colonization and pathogenesis using an in vivo model. We utilized C57BL/6 mice treated with streptomycin (to ensure a high colonization) then 24 h later infected with S. Typhimurium alone, or co-administered with S. Typhimurium and each EcN strain (3,4,66). The mice were monitored for clinical signs (weight loss, diarrhea, signs of abdominal pain) and the bacterial colonization was examined by enumeration of the feces, during 4 days (the point where the experiment must be arrested because of the lethality). When administered alone, S. Typhimurium readily colonized the intestine and this was associated with a high clinical score linked to a strong enteric salmonellosis (FIG. 8). In animals co-administered with the wild-type EcN, there was a marked reduction in the clinical scores and in S. Typhimurium fecal colonization (FIG. 8A-B). By day 2 following infection, EcN significantly outcompeted S. Typhimurium (FIG. 8C). In contrast, animals co-administered with the EcN ΔclbP mutant exhibited higher clinical scores and reduced antagonism of S. Typhimurium colonization, demonstrating the role of ClbP in EcN beneficial effect during acute Salmonella colitis. The EcN clbP-S95R strain reduced substantially the fecal shedding and outcompeted S. Typhimurium, and diminished the clinical scores, similarly to the wild-type EcN (FIG. 8).

Altogether, these results show that it is possible to decouple the genotoxic activity of EcN from its probiotic (antibacterial) activity, but also that the biosynthetic pathways of colibactin and siderophore-microcins are more entangled than initially thought.

The ClbP Dependent Antibacterial Activity is Observed in a Subset of E. coli Strains That Carry a Truncated Mcc Gene Cluster and the pks Island Comparative genomic analyses have shown that EcN is closely related to E. coli pyelonephritis strain CFT073 and the asymptomatic bacteriuria strain ABU83972 (18). These three strains, as well as the reference strain ATCC®25922, carry the pks island, the iroA locus, and a truncated Mcc gene cluster deprived of genes mcmL/mchA and mcmK/mchS1. Therefore, we assessed whether the siderophore-Mcc antibacterial effect of these strains was ClbP-dependent, as observed in EcN. The inhibitory effect of two sets of E. coli strains was tested in co-culture experiments against LF82, as well as their respective ΔclbP mutants: i) strains similar to EcN that carry both a truncated Mcc gene cluster and the pks island: strains CFT073, ABU83972, and ATCC®25922; and ii) strains that carry the pks island but which are deprived of Mcc encoding genes: the human commensal strain M1/5, the meningitis-causing strain SP15, the murine commensal strain NC101, and the laboratory strain MG1655 that hosts a bacterial artificial chromosome (BAC) bearing the pks island. The three wild-type strains that carry both a truncated Mcc gene cluster and the pks island exhibited a marked inhibitory effect as observed in EcN (data not shown). The inhibitory effect of all three corresponding ΔclbP mutant strains was significantly reduced, whereas ClbP complementation restored the initial phenotype (data not shown). In contrast, in strains carrying only the pks island, there was no significant difference in LF82 growth whether it was cultivated with the wild-type strains or the ΔclbP mutants (data not shown). Cumulatively, these results show that the peptidase ClbP is involved in MccH47 and MccM antibacterial activity in E. coli strains that carry both the pks island and a truncated form of the Mcc gene cluster. Our results also show that this association is present in both pathogenic strains and probiotic strains.

Distribution of pks, Salmochelin and the MccH47 and MccM Ggene Clusters in an E. coli Population We demonstrated that strains of E. coli that carry a truncated Mcc gene cluster exhibit a siderophore-Mcc-dependent antibacterial activity (data not shown). This antibacterial activity requires ClbP from the biosynthetic pathway that produces the genotoxin colibactin and IroB from the biosynthetic pathway that produces the siderophore salmochelin. Consequently, we checked this association between the pks island, the iro locus and the Mcc island in E. coli strains with genomes available in GenBank. Interestingly, all strains that lacked the mcmL and mcmK genes responsible for posttranslational modifications belonged to the B2 phylogroup and carried the pks island and iroA (data not shown), except for strain 1105 deprived of pks island. Conversely, the strains that carry mcmL/mchA and mcmK/mchS1 belonged to B1, C or D phylogroups and lacked the pks island. These particular associations of genetic determinants led to the hypothesis that the truncated island is present almost exclusively in strains that carry pks and the iroA locus. It suggests that this interplay between colibactin, salmochelin, and the siderophore-Mcc biosynthetic pathways is due to a co-selection in strains that is either pathogenic or probiotic.

Production of Beneficial Compounds Likely Involved in the Probiotic Activity of Nissle 1917 by the Nissle clbPS95R Strain Other metabolites than colibactin that are synthesized by the enzymes encoded on the pks island might have a role on the probiotic properties of Nissle 1917. It was recently shown that the metabolite C12AsnGABAOH is produced by Nissle 1917 wild-type (but not by a clbN mutant, indicating that the pks-encoded machinery has a role in its production) (34). C12-Asn-GABAOH was shown to inhibit nociceptors activation in neurons. Nociceptor neurons in the intestinal tract play an important role in protecting against enteropathogens and intestinal homeostasis, as they regulate M cell density and inflammation. Thus, it is important that we ensure that a non-genotoxic modified strain retain production of C12AsnGABAOH with a role in the anti-inflammatory property of Nissle.

We have quantified by HPLC-QQQ (34) N-acyl-Asn-GABAOH in bacterial cultures of Nissle 1917 wild type, Nissle clbN mutant and Nissle clbPS95R. The Nissle clbPS95R still produces the beneficial GABAOH lipopeptide similarly to the wild type strain (FIG. 9).

Genetic Stability of Nissle clbPS95R

To verify that the Nissle clbPS95R strain is genetically stable, we sequenced its genome DNA before and after oral gavage of a mouse (together with a pathogenic Salmonella (67)) and reisolation from the feces. The genomes were compared to that of the wild-type strain, which was also sequenced. The Nissle clbPS95R strain shown only 2 bp change (out of 5441200 bp) compared to the wild-type. No difference was found between Nissle clbPS95R before and after passage through the mouse intestine (data not shown). Thus, the Nissle clbPS95R appear genetically stable.

Discussion

Since Fleming discovered penicillin in 1928, antibiotics have contributed to the increase in human life expectancy. Many infections which were previously fatal became curable. Unfortunately, the overuse and misuse of antibiotics, in parallel with the lack of new antibacterial drugs enabled multi-resistant bacteria to emerge and spread (52). According to the World Health Organization (WHO), this phenomenon "poses a substantial threat to morbidity and mortality worldwide" (53). The trend is especially worrying for Gram-negative bacteria. For instance, the number of deaths attributable to $3^{rd}$ generation cephalosporin-resistant or carbapenem-resistant E. coli increased by more than 4 times in Europe between 2007 and 2015 (54). Of the antibiotics that are currently being developed for intravenous administration, only a small proportion (15 out of 44) demonstrates some activity against Gram-negative bacteria, and all these molecules are derived from known antibiotic classes. Consequently, the WHO established that research and development of new antibiotics against Gram-negative bacteria was a "critical priority" (53).

In the search for new antimicrobials, microcins seem a promising alternative to "conventional" antibiotics. In fact, many microcins exhibit potent narrow-spectrum antimicrobial activity, whereas antibiotics can eliminate beneficial bacteria, alter the microbiota and promote the selection of resistant strains (55,56). A major challenge in using microcins is their delivery in sufficient quantities to the site of infection, especially after oral administration because they are often degraded in the upper digestive tract (57,58). Engineered probiotic bacteria were consequently proposed as in situ producers of microcins to fight against enteropathogens (59) or to reduce colonization by multi-resistant bacteria (60).

EcN has been used as a probiotic for over a century, with numerous therapeutic benefits described. However, serious concerns about the safety of EcN administration have emerged over the years. EcN was reported to be responsible for severe sepsis in an infant (61) and its genome was shown to have the pathogenicity island pks (21,35), which codes for colibactin, a bona fide virulence factor for E. coli strains responsible for extraintestinal infections (26,27). In addition, the carriage of colibactin producing E. coli could also be deleterious to gut homeostasis. In adult rats, it increased intestinal epithelial permeability, led to signs of genotoxic damages in intestinal cells, such as crypt fission, and increased cell proliferation (28). In mice predisposed to colorectal cancer, pks-positive E. coli increased the size and the number of tumors (31,62). In human beings, several studies reported that pks-positive E. coli were over-represented in colorectal cancer biopsies compared to controls (31,32,63). On a whole, these studies suggest that colibactin-producing bacteria could promote tumorigenesis. Therefore, our goal was to understand the interplay between the production of the genotoxin colibactin and the beneficial effects related to the pks island in the probiotic activity of EcN. Consequently, we attempted to disarm EcN while keeping its probiotic properties.

In a previous attempt, our team constructed a non-genotoxic EcN PPTase ClbA mutant, which also lost its probiotic activity (35). Subsequently, it was discovered that the PPTase ClbA contributes to the synthesis of enterobactin (and therefore salmochelin) and yersiniabactin (36). In this study, we demonstrated that there is collaboration between the salmochelin (iroB) and the Mcc gene clusters, both of which are located on EcN genomic island I, and the pks island (clbP) (FIG. 6). The interweaving is so strong between these determinants, that a single protein, ClbP is involved both in colibactin and Mcc production. Up until now, ClbP had only been described as a peptidase that removes the N-acyl-D-asparagine prodrug scaffold from precolibactin (24,25). Although the complete C-terminal domain with the three transmembrane helices is required for the bioactivity of ClbP, the catalytic activity is performed by the N-terminal periplasmic domain (25,38). In this study, we demonstrated that the C-terminal domain of ClbP, deprived of the known enzymatic function, is necessary for EcN antibacterial activity due to MccH47 and MccM. It suggests that the ClbP C-terminal transmembrane domain could facilitate the export of the MccH47 and MccM of EcN through the MchE-MchF efflux pump (FIG. 7).

Using both functional and bioinformatic analyses, we demonstrated interplay between siderophore-Mcc, salmochelin, and colibactin assembly lines. Strikingly, two groups of E. coli strains emerged. On one hand, all strains that carry a "truncated" MccH47 and MccM gene cluster (i.e. strains such as EcN lacking mcmL/mchA and mcmK/mchS1) are B2 strains that also bear the pks island and the iroA locus. It should be noted that isolates from urine were over-represented in this group of strains (CFT073, clones D i14 and D i2, UPEC 26-1, and ABU 83972). On the other hand, the pks island and the iroA locus are absent in the non-B2 strains that carry a "complete" MccH47 and MccM gene cluster. All these strains were isolated from stools (except ACNO02 for which the origin is unknown). Therefore, we can hypothesize that these strains with a "complete" Mcc gene cluster are specialized in Mcc production in order to survive in the competitive intestinal environment, which is their exclusive niche. In contrast, extraintestinal pathogenic E. coli (ExPEC) must be efficient gut colonizers in order to emerge from the intestinal niche and infect other body sites (such as the urinary tract) to which they must subsequently adapt. That is why it has been suggested that ExPEC are "generalists" rather than specialized strains (64). The strains we examined in our study fit this model. They can express various virulence factors depending on their environment: MccH47 and M, siderophores and analgesic lipopeptides derived from the colibactin pathway, for instance. To be able to produce so many virulence or fitness factors with a genome of limited size (65), the elements of the assembly lines that produce these determinants must be versatile and intervene in several apparently independent metabolic pathways.

In conclusion, we discovered that the pks island is even more intimately connected to EcN probiotic activity than expected. This entanglement reflects the co-evolution of probiotic and pathogenic determinants to adapt to various environments. Decoupling the probiotic from the genotoxic activities by specifically targeting the enzymatic domain of ClbP opens the way to safe use of EcN.

TABLE 3

Strains and plasmids used in this study.

| Strain or plasmid | Genotype or phenotype | Source or reference |
|---|---|---|
| E. coli Nissle (EcN) | Probiotic strain; colibactin genotoxin producer; enterobactin and salmochellin siderophores producer; microcins H47 and M producer | DSM 6601, Mutaflor ® |
| EcN WT | EcN mutant in rpsl, Str$^R$ | [1, 2] |
| EcN ΔclbA | clbA mutant of strain EcN WT, Str$^R$, Kan$^R$ | [1] |
| EcN ΔclbB | clbB mutant of strain EcN WT, Str$^R$, Kan$^R$ | [3] |
| EcN ΔclbC | clbC mutant of strain EcN, Str$^R$, Chl$^R$ | [3] |
| EcN ΔclbH | clbH mutant of strain EcN WT, Str$^R$, Kan$^R$ | This study |
| EcN ΔclbL | clbL mutant of strain EcN WT, Str$^R$, Kan$^R$ | This study |
| EcN ΔclbM | clbM mutant of strain EcN WT, Str$^R$, Kan$^R$ | This study |
| EcN ΔclbN | clbN mutant of strain EcN WT, Str$^R$, Kan$^R$ | [3] |
| EcN ΔclbO | clbO mutant of strain EcN WT, Str$^R$, Kan$^R$ | This study |
| EcN ΔclbP | clbP mutant of strain EcN WT, Str$^R$, Kan$^R$ | [3] |
| EcN ΔclbP pclbP | EcN ΔclbP mutant complemented with pBRSKpclbP, Str$^R$, Kan$^R$, Carb$^R$ | This study |
| EcN ΔclbP pclbP-S95A | EcN ΔclbP mutant complemented with pclbP-S95A, Str$^R$, Kan$^R$, Carb$^R$ | This study |
| EcN ΔclbP pclbP-K98T | EcN ΔclbP mutant complemented with pclbP-K98T, Str$^R$, Kan$^R$, Carb$^R$ | This study |
| EcN ΔclbP pclbP-3H | EcN ΔclbP mutant complemented with pclbP-3H | This study |
| EcN clbP-S95R | EcN clbP-S95R chromosomal isogenic mutant | This study |
| EcN ΔclbQ | clbQ mutant of strain EcN WT, Str$^R$, Kan$^R$ | This study |
| EcN ΔmcmA | mcmA mutant of EcN WT, Str$^R$, Kan$^R$ | This study |
| EcN ΔmchB | mchB mutant of EcN WT, Str$^R$, Kan$^R$ | This study |
| EcN ΔmcmAΔmchB | mcmA mchB mutant of EcN WT, Str$^R$, Kan$^R$ | This study |
| EcN ΔmchCD | mchC mchD mutant of EcN WT, Str$^R$, Kan$^R$ | This study |
| EcN ΔmchCD::FRT | mchCD::FRT mutant of strain EcN WT, Str$^R$ | This study |
| EcN ΔmchCD pmchCD | EcN ΔmchCD::FRT complemented with TopoXL mchCD, Str$^R$, Kan$^R$ | This study |
| EcN ΔmchEF | mchE mchF mutant of EcN WT, Str$^R$, Kan$^R$ | This study |
| EcN ΔmchEF::FRT | mchEF::FRT mutant of strain EcN WT, Str$^R$ | This study |
| EcN ΔmchEF pmchEF | EcN ΔmchEF::FRT complemented with TopoXL mchEF, Str$^R$, Kan$^R$ | This study |
| EcN ΔentE | entE mutant of EcN WT, Str$^R$, Chl$^R$ | This study |
| EcN ΔentD | entD mutant of EcN WT, Str$^R$, Chl$^R$ | This study |
| EcN ΔentDΔclbA | clbA, entE mutant of EcN WT, Str$^R$, Kan$^R$ | This study |
| EcN ΔiroB | iroB mutant of EcN WT, Str$^R$, Chl$^R$ | This study |
| EcN ΔiroB piroB | EcN ΔiroB mutant complemented with pASK75 iroB | This study |
| EcN ΔiroC | iroC mutant of EcN WT, Str$^R$, Kan$^R$ | This study |
| EcN ΔiroD | iroD mutant of EcN WT, Str$^R$, Chl$^R$ | This study |
| EcN ΔiroE | iroE mutant of EcN WT, Str$^R$, Kan$^R$ | This study |
| E. coli LF82 | Strain isolated from an ileal biopsy of a patient with Crohn's disease; adherent-invasive E. coli, Rif$^R$ | [4] |
| LF82 pMcMi | LF82 carrying pMcMi, Rif$^R$, Carb$^R$ | This study |
| LF82 pMcHi | LF82 carrying pMcHi, Rif$^R$, Carb$^R$ | This study |
| E. coli M1/5 | Commensal E. coli strain isolated from feces of a healthy adult; B2 phylogenetic group; colibactin genotoxin producer; aerobactin, enterobactin and yersiniabactin siderophores producer | [5] |
| M1/5 ΔclbP | clbP mutant of strain M1/5, Kan$^R$ | [6] |
| E. coli SP15 | Strain isolated from spinal fluid of a neonate with meningitis; O18:K1 serotype; colibactin genotoxin producer; aerobactin, enterobactin, salmochelins and yersiniabactin siderophores producer | [7] |
| SP15 ΔclbP | clbP mutant of strain SP15, Kan$^R$ | This study |
| E. coli NC101 | Non-pathogenic murine E. Coli strain; colibactin genotoxin producer; | [8, 9] |
| NC101 ΔclbP | clbP mutant of strain NC101, Kan$^R$ | [10] |
| E. coli MG1655 bacpks | Enterobactin siderophore producer E. coli strain carrying a bacterial artificial chromosome bearing the entire pks island, Chl$^R$ | [11] |

TABLE 3-continued

Strains and plasmids used in this study.

| Strain or plasmid | Genotype or phenotype | Source or reference |
|---|---|---|
| MG1655 bacpks ΔclbP | clbP mutant of strain MG1655 bacpks, $Chl^R$ | This study |
| E. coli CFT073 | Strain isolated from a patient with pyelonephritis, colibactin genotoxin producer; enterobactin siderophores producer; microcins H47 and M producer | [12] |
| CFT073 ΔclbP | clbP mutant of strain CFT073, $Kan^R$ | This study |
| CFT ΔclbP pclbP | CFT073 ΔclbP mutant complemented with pBRSKpclbP, $Kan^R$, $Carb^R$ | This study |
| E. coli ABU83972 | Strain isolated from a patient with asymptomatic bacteriuria, colibactin genotoxin producer; enterobactin siderophores producer; microcins H47 and M producer | [13, 14] |
| ABU83972 ΔclbP | clbP mutant of strain ABU83972, $Kan^R$ | This study |
| ABU83972 ΔclbP pclbP | ABU83972 ΔclbP mutant complemented with pBRSKpclbP, $Kan^R$, $Carb^R$ | This study |
| E. coli ATCC ®25922 | Strain isolated from a patient in Seattle (1946), colibactin genotoxin producer; enterobactin siderophores producer; microcins H47 and M producer | DSM1103 |
| ATCC ®25922 ΔclbP | clbP mutant of strain ATCC ®25922, $Kan^R$ | This study |
| ATCC ®25922 ΔclbP pclbP | ATCC ®25922 ΔclbP mutant complemented with pBRSKpclbP, $Kan^R$, $Carb^R$ | This study |
| E. coli ST131 isolate JJ1886 | Strain isolated in the USA (2007) from a patient with fatal urosepsis, $Str^R$, $Kan^R$, $Carb^R$, $Chl^R$ | [15] |
| E. coli NRG857c | Strain isolated from the ileum of a Crohn's Disease patient, $Carb^R$, $Chl^R$ | [16] |
| Salmonella enterica serovar Typhimurium IR715 | $Nal^R$ derivative of S. enterica serovar Typhimurium ATCC14028 | [17] |
| Enterobacter aerogenes ATCC ®13048 | Strain isolated from sputum in the USA (Center for Disease Control and Prevention) | ATCC ®13048 |
| Klebsiella oxytoca ATCC ®13182 | Strain isolated from a pharyngeal tonsil | ATCC ®13182 |
| pclbP | pBRSK encoding clbP sequence | [18] |
| pclbP-S95A | pBRSK encoding the mutant S95A of ClbP (pOB902), $Carb^R$ | [18] |
| pclbP-K98T | pBRSK encoding the mutant K98T of ClbP (pOB903), $Carb^R$ | [18] |
| pclbP-3H | pASK74 carrying the fusion between ClbP N-terminal signal sequence, the alkaline phosphatase PhoA, and the 3 transmembrane helices of ClbP, $Carb^R$ | This study |
| pmchCD | pCR XL-TOPO vector encoding mchC and mchD from EcN, $Kan^R$ | This study |
| pmchEF | pCR XL-TOPO vector encoding mchE and mchF from EcN, $Kan^R$ | This study |
| pMcMi | Carrying mcmI from MccM gene cluster, $Carb^R$ | F. Moreno, unpublished data [19] |
| pMcHi | Carrying mchI from MccH47 gene cluster, ChlR | F. Moreno, unpublished data, [19] |

REFERENCES

Throughout this application, various references describe the state of the art to which this invention pertains. The disclosures of these references are hereby incorporated by reference into the present disclosure.

1. Wassenaar T M. Insights from 100 years of research with probiotic E. coli. Eur J Microbiol Immunol. 2016 Sep. 29; 6(3):147-61.
2. Sonnenborn U. Escherichia coli strain Nissle 1917—from bench to bedside and back: history of a special Escherichia coli strain with probiotic properties. FEMS Microbiol Lett [Internet]. 2016 Oct. 1 [cited 2017 Dec. 15]; 363(19). Available from: https://academic.oup.com/femsle/article/363/19/fnw212/2236266
3. Deriu E, Liu J Z, Pezeshki M, Edwards R A, Ochoa R J, Contreras H, et al. Probiotic bacteria reduce Salmonella Typhimurium intestinal colonization by competing for iron. Cell Host Microbe. 2013 Jul. 17; 14(1):26.
4. Sassone-Corsi M, Nuccio S-P, Liu H, Hernandez D, Vu C T, Takahashi A A, et al. Microcins mediate competition among Enterobacteriaceae in the inflamed gut. Nature. 2016 Dec. 8; 540(7632):280-3.
5. Rund S A, Rohde H, Sonnenborn U, Oelschlaeger T A. Antagonistic effects of probiotic Escherichia coli Nissle 1917 on EHEC strains of serotype 0104:H4 and 0157:H7. Int J Med Microbiol IJMM. 2013 January; 303(1):1-8.
6. Henker J, Laass M, Blokhin B M, Bolbot Y K, Maydannik V G, Elze M, et al. The probiotic Escherichia coli strain Nissle 1917 (EcN) stops acute diarrhoea in infants and toddlers. Eur J Pediatr. 2007 April; 166(4):311-8.
7. Möllenbrink M, Bruckschen E. [Treatment of chronic constipation with physiologic *Escherichia coli* bacteria. Results of a clinical study of the effectiveness and tolerance of microbiological therapy with the *Escherichia coli* Nissle 1917 strain (Mutaflor)]. Med Klin Munich Ger 1983.1994 Nov. 15; 89(11):587-93.
8. Kruis W, Chrubasik S, Boehm S, Stange C, Schulze J. A double-blind placebo-controlled trial to study therapeutic effects of probiotic *Escherichia coli* Nissle 1917 in subgroups of patients with irritable bowel syndrome. Int J Colorectal Dis. 2012 April; 27(4):467-74.
9. Losurdo G, Iannone A, Contaldo A, Ierardi E, Di Leo A, Principi M. *Escherichia coli* Nissle 1917 in ulcerative colitis treatment: systematic review and meta-analysis. J Gastrointest Liver Dis JGLD. 2015 December; 24(4):499-505.
10. Sonnenborn U, Schulze J. The non-pathogenic *Escherichia coli* strain Nissle 1917—features of a versatile probiotic. Microb Ecol Health Dis. 2009 September; 21(3/4):122-58.
11. Papavassiliou J. Biological characteristics of colicine X. Nature. 1961 Apr. 1; 190:110.
12. Patzer S I. The colicin G, H and X determinants encode microcins M and H47, which might utilize the catecholate siderophore receptors FepA, Cir, Fiu and IroN. Microbiology. 2003 Sep. 1; 149(9):2557-70.
13. Vassiliadis G, Destoumieux-Garzón D, Lombard C, Rebuffat S, Peduzzi J. Isolation and characterization of two members of the siderophore-microcin family, microcins M and H47. Antimicrob Agents Chemother. 2010 January; 54(1):288-97.
14. Asensio C, Pèrez-Diaz J C, Martinez M C, Baquero F. A new family of low molecular weight antibiotics from enterobacteria. Biochem Biophys Res Commun. 1976 Mar. 8; 69(1):7-14.
15. Duquesne S, Destoumieux-Garzón D, Peduzzi J, Rebuffat S. Microcins, gene-encoded antibacterial peptides from enterobacteria. Nat Prod Rep. 2007 Jul. 25; 24(4): 708-34.
16. Thomas X, Destoumieux-Garzón D, Peduzzi J, Afonso C, Blond A, Birlirakis N, et al. Siderophore peptide, a new type of post-translationally modified antibacterial peptide with potent activity. J Biol Chem. 2004 Jul. 2; 279(27): 28233-42.
17. Nolan E M, Fischbach M A, Koglin A, Walsh C T. Biosynthetic tailoring of microcin E492m: post-translational modification affords an antibacterial siderophore-peptide conjugate. J Am Chem Soc. 2007 Nov. 21; 129(46):14336-47.
18. Grozdanov L, Raasch C, Schulze J, Sonnenborn U, Gottschalk G, Hacker J, et al. Analysis of the genome structure of the 41arbour41g4lenic probiotic *Escherichia coli* strain Nissle 1917. J Bacteriol. 2004 August; 186 (16):5432-41.
19. Vejborg R M, Friis C, Hancock V, Schembri M A, Klemm P. A virulent parent with probiotic progeny: comparative genomics of *Escherichia coli* strains CFT073, Nissle 1917 and ABU 83972. Mol Genet Genomics. 2010 Mar. 31; 283(5):469-84.
20. Reister M, Hoffmeier K, Krezdorn N, Rotter B, Liang C, Rund S, et al. Complete genome sequence of the gram-negative probiotic *Escherichia coli* strain Nissle 1917. J Biotechnol. 2014 Oct. 10; 187:106-7.
21. Nougayrède J-P, Homburg S, Taieb F, Boury M, Brzuszkiewicz E, Gottschalk G, et al. *Escherichia coli* induces DNA double-strand breaks in eukaryotic cells. Science. 2006 Aug. 11; 313(5788):848-51.
22. Cuevas-Ramos G, Petit C R, Marcq I, Boury M, Oswald E, Nougayrède J-P. *Escherichia coli* induces DNA damage in vivo and triggers genomic instability in mammalian cells. Proc Natl Acad Sci USA. 2010 Jun. 22; 107(25): 11537-42.
23. Mousa J J, Yang Y, Tomkovich S, Shima A, Newsome R C, Tripathi P, et al. MATE transport of the *E. coli*-derived genotoxin colibactin. Nat Microbiol. 2016 Jan. 11; 1(1): nmicrobio120159.
24. Dubois D, Baron O, Cougnoux A, Delmas J, Pradel N, Boury M, et al. ClbP is a prototype of a peptidase subgroup involved in biosynthesis of nonribosomal peptides. J Biol Chem. 2011 Oct. 14; 286(41):35562-70.
25. Brotherton C A, Balskus E P. A prodrug resistance mechanism is involved in colibactin biosynthesis and cytotoxicity. J Am Chem Soc. 2013 Mar. 6; 135(9):3359-62.
26. Marcq I, Martin P, Payros D, Cuevas-Ramos G, Boury M, Watrin C, et al. The genotoxin colibactin exacerbates lymphopenia and decreases survival rate in mice infected with septicemic *Escherichia coli*. J Infect Dis. 2014 Jul. 15; 210(2):285-94.
27. McCarthy A J, Martin P, Cloup E, Stabler R A, Oswald E, Taylor P W. The genotoxin colibactin is a determinant of virulence in *Escherichia coli* K1 experimental neonatal systemic infection. Infect Immun. 2015 Sep. 1; 83(9): 3704-11.
28. Payros D, Secher T, Boury M, Brehin C, Ménard S, Salvador-Cartier C, et al. Maternally acquired genotoxic *Escherichia coli* alters offspring's intestinal homeostasis. Gut Microbes. 2014 May 1; 5(3):313-25.
29. Bossuet-Greif N, Vignard J, Taieb F, Mirey G, Dubois D, Petit C, et al. The colibactin genotoxin generates DNA interstrand cross-links in infected cells. mBio [Internet]. 2018 Mar. 20 [cited 2018 Nov. 21]; 9(2). Available from: https://www.ncbi.nlm.nih.gov/pmc/articles/PMC5874909/30.
30. Xue M, Shine E, Wang W, Crawford J M, Herzon S B. Characterization of natural colibactin-nucleobase adducts by tandem mass spectrometry and isotopic 42arbour42g. Support for DNA alkylation by cyclopropane ring opening. Biochemistry. 2018 Nov. 13; 57(45):6391-4.
31. Arthur J C, Pèrez-Chanona E, Mühlbauer M, Tomkovich S, Uronis J M, Fan T-J, et al. Intestinal inflammation targets cancer-inducing activity of the microbiota. Science. 2012 Oct. 5; 338(6103):120-3.
32. Buc E, Dubois D, Sauvanet P, Raisch J, Delmas J, Darfeuille-Michaud A, et al. High prevalence of mucosa-associated *E. coli* producing cyclomodulin and genotoxin in colon cancer. PloS ONE [Internet]. 2013 Feb. 14 [cited 2018 Oct. 24]; 8(2). Available from: https://www.ncbi.nlm.nih.gov/pmc/articles/PMC3572998/33.
33. Cougnoux A, Dalmasso G, Martinez R, Buc E, Delmas J, Gibold L, et al. Bacterial genotoxin colibactin promotes colon tumour growth by inducing a senescence-associated secretory phenotype. Gut. 2014 December; 63(12):1932-42.
34. Pèrez-Berezo T, Pujo J, Martin P, Faouder P, Galano J-M, Guy A, et al. Identification of an analgesic lipopeptide produced by the probiotic *Escherichia coli* strain Nissle 1917. Nat Commun. 2017 Nov. 3; 8(1):1314.
35. Olier M, Marcq I, Salvador-Cartier C, Secher T, Dobrindt U, Boury M, et al. Genotoxicity of *Escherichia coli* Nissle 1917 strain cannot be dissociated from its probiotic activity. Gut Microbes. 2012 Nov. 1; 3(6):501-9.

36. Martin P, Marcq I, Magistro G, Penary M, Garcie C, Payros D, et al. Interplay between siderophores and colibactin genotoxin biosynthetic pathways in *Escherichia coli*. PloS Pathog [Internet]. 2013 July [cited 2015 Dec. 8]; 9(7). Available from: http://www.ncbi.nlm.nih.gov/pmc/articles/PMC3708854/37.

37. Datsenko K A, Wanner B L. One-step inactivation of chromosomal genes in *Escherichia coli* K-12 using PCR products. Proc Natl Acad Sci U S A. 2000 Jun. 6; 97(12):6640-5.

38. Cougnoux A, Gibold L, Robin F, Dubois D, Pradel N, Darfeuille-Michaud A, et al. Analysis of structure-function relationships in the colibactin-maturating enzyme ClbP. J Mol Biol. 2012 decembre; 424(3-4):203-14.

39. Gallagher R R, Li Z, Lewis A O, Isaacs F J. Rapid editing and evolution of bacterial genomes using libraries of synthetic DNA. Nat Protoc. 2014 October; 9(10):2301-16.

40. Bossuet-Greif N, Belloy M, Boury M, Oswald E, Nougayrede J-P. Protocol for HeLa cells infection with *Escherichia coli* strains producing colibactin and quantification of the induced DNA-damage. BIO-Protoc [Internet]. 2017 [cited 2019 Jan. 21]; 7(16). Available from: https://bio-protocol.org/e2520

41. Boudeau J, Glasser A-L, Masseret E, Joly B, Darfeuille-Michaud A. Invasive ability of an *Escherichia coli* strain isolated from the ileal mucosa of a patient with Crohn's disease. Infect Immun. 1999 September; 67(9):4499-509.

42. Clermont O, Christenson J K, Denamur E, Gordon D M. The Clermont *Escherichia coli* phylo-typing method revisited: improvement of specificity and detection of new phylo-groups. Environ Microbiol Rep. 2013 Feb. 1; 5(1): 58-65.

43. Wattam A R, Davis J J, Assaf R, Boisvert S, Brettin T, Bun C, et al. Improvements to PATRIC, the all-bacterial bioinformatics database and analysis resource center. Nucleic Acids Res. 2017 Jan. 4; 45(D1):D535-42.

44. Kumar S, Stecher G, Tamura K. MEGA7: Molecular Evolutionary Genetics Analysis Version 7.0 for Bigger Datasets. Mol Biol Evol. 2016 Jul. 1; 33(7):1870-4.

45. Boudeau J, Glasser A-L, Julien S, Colombel J-F, Darfeuille-Michaud A. Inhibitory effect of probiotic *Escherichia coli* strain Nissle 1917 on adhesion to and invasion of intestinal epithelial cells by adherent-invasive *Escherichia coli* strains isolated from patients with Crohn's disease. Aliment Pharmacol Ther. 2003 juillet; 18(1):45-56.

46. Huebner C, Ding Y, Petermann I, Knapp C, Ferguson L R. The probiotic *Escherichia coli* Nissle 1917 reduces pathogen invasion and modulates cytokine expression in Caco-2 cells infected with Crohn's disease-associated *E. coli* LF82. Appl Environ Microbiol. 2011 Apr. 1; 77(7): 2541-4.

47. Rusnak F, Faraci W S, Walsh C T. Subcloning, expression, and purification of the enterobactin biosynthetic enzyme 2,3-dihydroxybenzoate-AMP ligase: demonstration of enzyme-bound (2,3-dihydroxybenzoyl)adenylate product. Biochemistry. 1989 Aug. 22; 28(17):6827-35.

48. Poey M E, Azpiroz M F, Laviña M. Comparative analysis of chromosome-encoded microcins. Antimicrob Agents Chemother. 2006 April; 50(4):1411-8.

49. Lin H, Fischbach M A, Liu D R, Walsh C T. In vitro characterization of salmochelin and enterobactin trilactone hydrolases IroD, IroE, and Fes. J Am Chem Soc. 2005 Aug. 10; 127(31):11075.

50. Zhu M, Valdebenito M, Winkelmann G, Hantke K. Functions of the siderophore esterases IroD and IroE in iron-salmochelin utilization. Microbiology. 2005; 151(7): 2363-72.

51. Nolan E M, Walsh C T. Investigations of the MceIJ-catalyzed posttranslational modification of the microcin E492 C-terminus: linkage of ribosomal and nonribosomal peptides to form "Trojan Horse" antibiotics. Biochemistry. 2008 Sep. 2; 47(35):9289-99.

52. Ventola C L. The Antibiotic Resistance Crisis. Pharm Ther. 2015 April; 40(4):277-83.

53. Tacconelli E, Carrara E, Savoldi A, Harbarth S, Mendelson M, Monnet D L, et al. Discovery, research, and development of new antibiotics: the WHO priority list of antibiotic-resistant bacteria and tuberculosis. Lancet Infect Dis. 2018 Mar. 1; 18(3): 318-27.

54. Cassini A, Hogberg L D, Plachouras D, Quattrocchi A, Hoxha A, Simonsen G S, et al. Attributable deaths and disability-adjusted life-years caused by infections with antibiotic-resistant bacteria in the EU and the European Economic Area in 2015: a population-level modelling analysis. Lancet Infect Dis [Internet]. 2018 Nov. 5 [cited 2018 Nov. 26]; 0(0). Available from: https://www.thelancet.com/journals/laninf/article/PIIS1473-3099(18) 30605-4/abstract 55. Cotter P D, Ross R P, Hill C. Bacteriocins—a viable alternative to antibiotics? Nat Rev Microbiol. 2013 February; 11(2):95-105.

56. Raffatellu M. Learning from bacterial competition in the host to develop antimicrobials. Nat Med. 2018 August; 24(8):1097-103.

57. Gardiner G E, Rea M C, O'Riordan B, O'Connor P, Morgan S M, Lawlor P G, et al. Fate of the two-component lantibiotic lacticin 3147 in the gastrointestinal tract. Appl Environ Microbiol. 2007 November; 73(21): 7103-9.

58. Naimi S, Zirah S, Hammami R, Fernandez B, Rebuffat S, Fliss I. Fate and biological activity of the antimicrobial lasso peptide microcin J25 under gastrointestinal tract conditions. Front Microbiol [Internet]. 2018 Aug. 3 [cited 2018 Nov. 27]; 9. Available from: https://www.ncbi.nlm.nih.gov/pmc/articles/PMC6085462/59.

59. Forkus B, Ritter S, Vlysidis M, Geldart K, Kaznessis Y N. Antimicrobial Probiotics Reduce *Salmonella enterica* in Turkey Gastrointestinal Tracts. Sci Rep. 2017 Jan. 17; 7:40695.

60. Geldart K G, Kommineni S, Forbes M, Hayward M, Dunny G M, Salzman N H, et al. Engineered *E. coli* Nissle 1917 for the reduction of vancomycin-resistant Enterococcus in the intestinal tract. Bioeng Transl Med. 2018 Sep. 8; 3(3):197-208.

61. Guenther K, Straube E, Pfister W, Guenther A, Huebler A. Sever sepsis after probiotic treatment with *Escherichia coli* Nissle 1917. Pediatr Infect Dis J. 2010 Feb. 1; 29(2):188-9.

62. Bonnet M, Buc E, Sauvanet P, Darcha C, Dubois D, Pereira B, et al. Colonization of the human gut by *E. coli* and colorectal cancer risk. Clin Cancer Res Off J Am Assoc Cancer Res. 2014 Feb. 15; 20(4):859-67.

63. Dejea C M, Fathi P, Craig J M, Boleij A, Taddese R, Geis A L, et al. Patients with familial adenomatous polyposis 45arbour colonic biofilms containing tumorigenic bacteria. Science. 2018 Feb. 2; 359(6375):592-7.

64. Johnson J R, Russo T A. Extraintestinal pathogenic *Escherichia coli*: "The other bad *E. coli*". J Lab Clin Med. 2002 Mar. 1; 139(3):155-62.

65. Hendrickson H. Order and disorder during *Escherichia coli* divergence. PloS Genet. 2009 January; 5(1): e1000335.
66. Barthel M, Hapfelmeier S, Quintanilla-Martinez L, Kremer M, Rohde M, Hogardt M, et al. Pretreatment of mice with streptomycin provides a *Salmonella enterica* serovar *Typhimurium* colitis model that allows analysis of both pathogen and host. Infect Immun. 2003 May; 71(5): 2839-58.
67. Massip C. et al. Deciphering the interplay between the genotoxic and probiotic activities of *Escherichia coli* Nissle 1917. PLoS Pathog. 2019 Sep. 23; 15(9): e1008029.

The invention claimed is:

1. An *Escherichia coli* strain Nissle 1917 (EcN) bacterium carrying a gene encoding a ClbP protein which is comprising an inactive for the peptidase domain,
wherein said EcN bacterium (i) has antibacterial activity; and ii) is devoid of the capacity to activate the genotoxin colibactin.

2. The EcN bacterium according to claim 1 wherein the ClbP protein comprising an inactive peptidase domain, is selected from the group consisting of:
ClbP protein mutated at position S95,
ClbP protein mutated at position K98,
ClbP protein mutated at position Y186, and
ClbP protein without peptidase domain.

3. The EcN bacterium according to claim 2, wherein the ClbP protein is mutated at position S95.

4. The EcN bacterium according to claim 2, wherein the ClbP protein is mutated at position K98.

5. The EcN bacterium according to claim 2, wherein the ClbP protein is mutated at position Y186.

6. The EcN bacterium according to claim 2 wherein the ClbP protein comprising an inactive peptidase domain, is selected from the group consisting of
ClbP S95A mutant (SEQ ID No 4),
ClbP K98T mutant (SEQ ID No 6),
ClbP S95R mutant (SEQ ID No 8),
ClbP Y186G mutant (SEQ ID No 10), and
ClbP protein with a peptidase domain substituted by an alkaline phosphatase enzymatic domain of PhoA (SEQ ID No 11).

7. A method of providing a probiotic to a subject in need thereof, comprising
administering to the subject a therapeutically effective amount of an EcN bacterium carrying a gene encoding a ClbP protein having an inactive peptidase domain, wherein said EcN bacterium (i) has antibacterial activity; and ii) is devoid of the capacity to activate the genotoxin colibactin.

8. A method of treating a gastro-intestinal disease in a subject in need thereof, comprising,
administering to the subject a therapeutically effective amount of an *Escherichia coli* strain Nissle 1917 (EcN) bacterium carrying a gene encoding a ClbP protein having an inactive peptidase domain, wherein said EcN bacterium (i) has antibacterial activity; and ii) is devoid of the capacity to activate the genotoxin colibactin.

9. The method according to claim 8 wherein the gastrointestinal disease is selected from the group consisting of bacterial gastrointestinal infections, gut inflammatory disease and visceral pain.

10. The method according to claim 9, wherein the bacterial gastrointestinal infections is *Salmonella enterica* serovar *Enteritidis*, a *Typhimurium* infection or an enterohemorrhagic *E. coli* infections.

11. The method according to claim 9, wherein the gut inflammatory disease is Inflammatory Bowel Diseases (IBD) or Irritable Bowel Syndrome (IBS).

12. The method according to claim 11, wherein the Inflammatory Bowel Diseases (IBD) is selected from the group consisting of Crohn's Disease, Ulcerative Colitis, Celiac disease, Gluten hypersensitivity and Pouchitis.

13. The method according to claim 9, wherein the visceral pain is pain associated with inflammatory bowel disease (IBD) or with Irritable Bowel Syndrome (IBS).

14. A method for treating gastro-intestinal disease in a subject thereof comprising administering to said subject a therapeutically effective amount of an EcN bacterium according claim 1.

15. The EcN bacterium according to claim 3, wherein the ClbP protein is not substituted with an amino acid that is a polar and non-charged equivalent of Serine.

16. The EcN bacterium according to claim 4, wherein the ClbP protein is not substituted with an amino acid that is a positively charged equivalent of Lysine.

17. The EcN bacterium according to claim 5, wherein the ClbP protein is not substituted with an amino acid that is a hydrophobic equivalent of Tyrosine.

* * * * *

SEQUENCE LISTING

```
<160> NUMBER OF SEQ ID NOS: 12

<210> SEQ ID NO 1
<211> LENGTH: 504
<212> TYPE: PRT
<213> ORGANISM: Escherichia coli

<400> SEQUENCE: 1

Met Thr Ile Met Glu His Val Ser Ile Lys Thr Leu Tyr His Leu Leu
1               5                   10                  15

Cys Cys Met Leu Leu Phe Ile Ser Ala Met Cys Ala Leu Ala Gln Glu
                20                  25                  30

His Glu Pro Ile Gly Ala Gln Asp Glu Arg Leu Ser Thr Leu Ile His
            35                  40                  45

Gln Arg Met Gln Glu Ala Lys Val Pro Ala Leu Ser Val Ser Val Thr
    50                  55                  60

Ile Lys Gly Val Arg Gln Arg Phe Val Tyr Gly Val Ala Asp Val Ala
65                  70                  75                  80

Ser Gln Lys Ala Asn Thr Leu Asp Thr Val Tyr Glu Leu Gly Ser Met
                85                  90                  95

Ser Lys Ala Phe Thr Gly Leu Val Val Gln Ile Leu Ile Gln Glu Gly
            100                 105                 110

Arg Leu Arg Gln Gly Asp Asp Ile Ile Thr Tyr Leu Pro Glu Met Arg
        115                 120                 125

Leu Asn Tyr Gln Gly Lys Pro Ala Ser Leu Thr Val Ala Asp Phe Leu
    130                 135                 140

Tyr His Thr Ser Gly Leu Pro Phe Ser Thr Leu Ala Arg Leu Glu Asn
145                 150                 155                 160

Pro Met Pro Gly Ser Ala Val Ala Gln Gln Leu Arg Asn Glu Asn Leu
                165                 170                 175

Leu Phe Ala Pro Gly Ala Lys Phe Ser Tyr Ala Ser Ala Asn Tyr Asp
            180                 185                 190

Val Leu Gly Ala Val Ile Glu Asn Val Thr Gly Lys Thr Phe Thr Glu
        195                 200                 205

Val Ile Ala Glu Arg Leu Thr Gln Pro Leu Gly Met Ser Ala Thr Val
    210                 215                 220

Ala Val Lys Gly Asp Glu Ile Ile Val Asn Lys Ala Ser Gly Tyr Lys
225                 230                 235                 240

Leu Gly Phe Gly Lys Pro Val Leu Phe His Ala Pro Leu Ala Arg Asn
                245                 250                 255

His Val Pro Ala Ala Tyr Ile His Ser Thr Leu Pro Asp Met Glu Ile
            260                 265                 270

Trp Ile Asp Ala Trp Leu His Arg Lys Ala Leu Pro Ala Thr Leu Arg
        275                 280                 285

Glu Ala Met Ser Asn Ser Trp Arg Gly Asn Ser Asp Val Pro Leu Ala
    290                 295                 300
```

```
Ala Asp Asn Arg Ile Leu Tyr Ala Ser Gly Trp Phe Ile Asp Gln Asn
305                 310                 315                 320

Gln Gly Pro Tyr Ile Ser His Gly Gly Gln Asn Pro Asn Phe Ser Ser
            325                 330                 335

Cys Ile Ala Leu Arg Pro Asp Gln Gln Ile Gly Ile Val Ala Leu Ala
                340                 345                 350

Asn Met Asn Ser Asn Leu Ile Leu Gln Leu Cys Ala Asp Ile Asp Asn
            355                 360                 365

Tyr Leu Arg Ile Gly Lys Tyr Ala Asp Gly Ala Gly Asp Ala Ile Thr
        370                 375                 380

Ala Thr Asp Thr Leu Phe Val Tyr Leu Thr Leu Leu Cys Phe Trp
385                 390                 395                 400

Gly Ala Val Val Val Arg Gly Ala Phe Arg Val Tyr Arg Ala Thr
                405                 410                 415

Ala His Gly Pro Gly Lys Gln Gln Arg Leu Arg Leu Arg Val Arg Asp
            420                 425                 430

Tyr Ile Ile Ala Leu Ala Val Pro Gly Leu Val Ala Ala Met Leu Tyr
        435                 440                 445

Val Ala Pro Gly Ile Leu Ser Pro Gly Leu Asp Trp Arg Phe Ile Leu
450                 455                 460

Val Trp Gly Pro Ser Ser Val Leu Ala Ile Pro Phe Gly Ile Ile Leu
465                 470                 475                 480

Leu Ala Phe Val Leu Thr Leu Asn His Gln Ile Lys Arg Ile Leu Leu
                485                 490                 495

His Asn Lys Glu Trp Asp Asp Glu
            500

<210> SEQ ID NO 2
<211> LENGTH: 1515
<212> TYPE: DNA
<213> ORGANISM: Escherichia coli

<400> SEQUENCE: 2
atgacaataa tggaacacgt tagcattaaa acattatatc atctcctgtg ctgtatgctg      60
ctctttattt ccgctatgtg cgctttggcg caagaacatg agcctatcgg ggcgcaagat     120
gagcgcctgt cgacattaat tcaccaacgg atgcaggagg ccaaggtccc agcccttccc     180
gtaagtgtga ccattaaggg ggtacgtcag cgatttgtct acggtgttgc cgatgtggct     240
agtcagaaag cgaatactct agacacagtt tacgagctgg gatcgatgag taaggcgttt     300
accggacttg tggtgcaaat actgattcag gaaggcagac tccggcaagg ggatgatatc     360
attacctatc tgccggaaat gcgcttgaat tatcagggaa acctgcttc cctgaccgtg     420
gctgatttcc tttatcatac atcaggattg ccttttcaa cactggctcg gctggaaaac     480
cctatgcctg ggagcgctgt ggcacagcaa ctgcgcaacg agaatctgct gtttgcgccg     540
ggtgcgaagt ttagctatgc ctccgccaat tatgatgtgt gggcgcggt gattgaaaat     600
gtgacgggaa aaacctttac agaggtcatt gcggaacgac tcacgcagcc gctgggcatg     660
tcggcgactg tggcagttaa ggggatgag attattgtca acaaggcaag cggctataaa     720
ctgggattcg gcaaacccgt tctgtttcat gcgcctctgg cccggaacca tgttcctgcc     780
gcctatatcc atagcactct gcctgatatg gaaatatgga tagacgcctg gttgcacaga     840
aaggctttgc cggcaacgct gcgtgaggcg atgagtaaca gttggcgtgg taatagtgat     900
gttccgcttg ccgcagacaa tcgtatcctc tatgccagcg gttggtttat cgaccagaat     960
```

-continued

```
caaggcccctt acatcagtca cggtgggcag aatccaaact tttcttcttg cattgcgttg    1020
cgaccggatc agcagattgg cattgttgcg ctggcaaata tgaattcgaa tctgatacta    1080
cagctttgcg cggatatcga taattatctg cgcattggca aatatgctga cggcgctggt    1140
gatgcaatta cagccaccga tacccttttc gtctacctca cgttgttgct gtgttttttgg    1200 ggggcggtgg ttgtagtgcg cggtgctttc cgtgtttatc gcgcaacggc gcatggccct    1260
ggaaaacagc agaggttacg tttacgcgta cgtgactata tcatcgcctt ggcggttcct    1320
gggctcgtgg ccgccatgct ctatgtcgca ccgggtatac tatctccagg acttgactgg    1380
cgttttatct tggtatgggg tccatcgagc gtgttggcga taccgttcgg aattatcctg    1440
ttagctttcg ttctgacatt aaatcatcaa attaaacgaa ttctattaca caacaaggag    1500
tgggacgatg agtaa                                                      1515
```

<210> SEQ ID NO 3
<211> LENGTH: 299
<212> TYPE: PRT
<213> ORGANISM: Artificial
<220> FEATURE:
<223> OTHER INFORMATION: Peptidase domain of ClbP protein

<400> SEQUENCE: 3

```
Gln Asp Glu Arg Leu Ser Thr Leu Ile His Gln Arg Met Gln Glu Ala
1               5                   10                  15

Lys Val Pro Ala Leu Ser Val Ser Val Thr Ile Lys Gly Val Arg Gln
            20                  25                  30

Arg Phe Val Tyr Gly Val Ala Asp Val Ala Ser Gln Lys Ala Asn Thr
        35                  40                  45

Leu Asp Thr Val Tyr Glu Leu Gly Ser Met Ser Lys Ala Phe Thr Gly
    50                  55                  60

Leu Val Val Gln Ile Leu Ile Gln Glu Gly Arg Leu Arg Gln Gly Asp
65                  70                  75                  80

Asp Ile Ile Thr Tyr Leu Pro Glu Met Arg Leu Asn Tyr Gln Gly Lys
                85                  90                  95

Pro Ala Ser Leu Thr Val Ala Asp Phe Leu Tyr His Thr Ser Gly Leu
            100                 105                 110

Pro Phe Ser Thr Leu Ala Arg Leu Glu Asn Pro Met Pro Gly Ser Ala
        115                 120                 125

Val Ala Gln Gln Leu Arg Asn Glu Asn Leu Leu Phe Ala Pro Gly Ala
    130                 135                 140

Lys Phe Ser Tyr Ala Ser Ala Asn Tyr Asp Val Leu Gly Ala Val Ile
145                 150                 155                 160

Glu Asn Val Thr Gly Lys Thr Phe Thr Glu Val Ile Ala Glu Arg Leu
                165                 170                 175

Thr Gln Pro Leu Gly Met Ser Ala Thr Val Ala Val Lys Gly Asp Glu
            180                 185                 190

Ile Ile Val Asn Lys Ala Ser Gly Tyr Lys Leu Gly Phe Gly Lys Pro
        195                 200                 205

Val Leu Phe His Ala Pro Leu Ala Arg Asn His Val Pro Ala Ala Tyr
    210                 215                 220

Ile His Ser Thr Leu Pro Asp Met Glu Ile Trp Ile Asp Ala Trp Leu
225                 230                 235                 240

His Arg Lys Ala Leu Pro Ala Thr Leu Arg Glu Ala Met Ser Asn Ser
                245                 250                 255

Trp Arg Gly Asn Ser Asp Val Pro Leu Ala Ala Asp Asn Arg Ile Leu
```

```
                260                 265                 270
Tyr Ala Ser Gly Trp Phe Ile Asp Gln Asn Gln Gly Pro Tyr Ile Ser
            275                 280                 285

His Gly Gly Gln Asn Pro Asn Phe Ser Ser Cys
            290                 295

<210> SEQ ID NO 4
<211> LENGTH: 504
<212> TYPE: PRT
<213> ORGANISM: Artificial
<220> FEATURE:
<223> OTHER INFORMATION: ClbP S95A

<400> SEQUENCE: 4

Met Thr Ile Met Glu His Val Ser Ile Lys Thr Leu Tyr His Leu Leu
1               5                   10                  15

Cys Cys Met Leu Leu Phe Ile Ser Ala Met Cys Ala Leu Ala Gln Glu
            20                  25                  30

His Glu Pro Ile Gly Ala Gln Asp Glu Arg Leu Ser Thr Leu Ile His
        35                  40                  45

Gln Arg Met Gln Glu Ala Lys Val Pro Ala Leu Ser Val Ser Val Thr
    50                  55                  60

Ile Lys Gly Val Arg Gln Arg Phe Val Tyr Gly Val Ala Asp Val Ala
65                  70                  75                  80

Ser Gln Lys Ala Asn Thr Leu Asp Thr Val Tyr Glu Leu Gly Ala Met
                85                  90                  95

Ser Lys Ala Phe Thr Gly Leu Val Val Gln Ile Leu Ile Gln Glu Gly
            100                 105                 110

Arg Leu Arg Gln Gly Asp Asp Ile Ile Thr Tyr Leu Pro Glu Met Arg
        115                 120                 125

Leu Asn Tyr Gln Gly Lys Pro Ala Ser Leu Thr Val Ala Asp Phe Leu
    130                 135                 140

Tyr His Thr Ser Gly Leu Pro Phe Ser Thr Leu Ala Arg Leu Glu Asn
145                 150                 155                 160

Pro Met Pro Gly Ser Ala Val Ala Gln Gln Leu Arg Asn Glu Asn Leu
                165                 170                 175

Leu Phe Ala Pro Gly Ala Lys Phe Ser Tyr Ala Ser Ala Asn Tyr Asp
            180                 185                 190

Val Leu Gly Ala Val Ile Glu Asn Val Thr Gly Lys Thr Phe Thr Glu
        195                 200                 205

Val Ile Ala Glu Arg Leu Thr Gln Pro Leu Gly Met Ser Ala Thr Val
    210                 215                 220

Ala Val Lys Gly Asp Glu Ile Ile Val Asn Lys Ala Ser Gly Tyr Lys
225                 230                 235                 240

Leu Gly Phe Gly Lys Pro Val Leu Phe His Ala Pro Leu Ala Arg Asn
                245                 250                 255

His Val Pro Ala Ala Tyr Ile His Ser Thr Leu Pro Asp Met Glu Ile
            260                 265                 270

Trp Ile Asp Ala Trp Leu His Arg Lys Ala Leu Pro Ala Thr Leu Arg
        275                 280                 285

Glu Ala Met Ser Asn Ser Trp Arg Gly Asn Ser Asp Val Pro Leu Ala
    290                 295                 300

Ala Asp Asn Arg Ile Leu Tyr Ala Ser Gly Trp Phe Ile Asp Gln Asn
305                 310                 315                 320

Gln Gly Pro Tyr Ile Ser His Gly Gly Gln Asn Pro Asn Phe Ser Ser
```

```
            325                 330                 335
Cys Ile Ala Leu Arg Pro Asp Gln Gln Ile Gly Ile Val Ala Leu Ala
        340                 345                 350

Asn Met Asn Ser Asn Leu Ile Leu Gln Leu Cys Ala Asp Ile Asp Asn
        355                 360                 365

Tyr Leu Arg Ile Gly Lys Tyr Ala Asp Gly Ala Gly Asp Ala Ile Thr
        370                 375                 380

Ala Thr Asp Thr Leu Phe Val Tyr Leu Thr Leu Leu Cys Phe Trp
385                 390                 395                 400

Gly Ala Val Val Val Arg Gly Ala Phe Arg Val Tyr Arg Ala Thr
                405                 410                 415

Ala His Gly Pro Gly Lys Gln Gln Arg Leu Arg Leu Arg Val Arg Asp
        420                 425                 430

Tyr Ile Ile Ala Leu Ala Val Pro Gly Leu Val Ala Ala Met Leu Tyr
            435                 440                 445

Val Ala Pro Gly Ile Leu Ser Pro Gly Leu Asp Trp Arg Phe Ile Leu
450                 455                 460

Val Trp Gly Pro Ser Ser Val Leu Ala Ile Pro Phe Gly Ile Ile Leu
465                 470                 475                 480

Leu Ala Phe Val Leu Thr Leu Asn His Gln Ile Lys Arg Ile Leu Leu
                485                 490                 495

His Asn Lys Glu Trp Asp Asp Glu
            500
```

<210> SEQ ID NO 5
<211> LENGTH: 1515
<212> TYPE: DNA
<213> ORGANISM: Artificial
<220> FEATURE:
<223> OTHER INFORMATION: ClbP S95A

<400> SEQUENCE: 5

```
atgacaataa tggaacacgt tagcattaaa acattatatc atctcctgtg ctgtatgctg      60
ctctttattt ccgctatgtg cgctttggcg caagaacatg agcctatcgg ggcgcaagat     120
gagcgcctgt cgacattaat tcaccaacgg atgcaggagg ccaaggtccc agcccttttcc    180 gtaagtgtga ccattaaggg ggtacgtcag cgatttgtct acggtgttgc cgatgtggct     240
agtcagaaag cgaatactct agacacagtt tacgagctgg gagcgatgag taaggcgttt     300
accggacttg tggtgcaaat actgattcag gaaggcagac tccggcaagg ggatgatatc     360
attacctatc tgccggaaat gcgcttgaat tatcagggaa aacctgcttc cctgaccgtg     420
gctgatttcc tttatcatac atcaggattg cctttttcaa cactggctcg gctggaaaac     480
cctatgcctg ggagcgctgt ggcacagcaa ctgcgcaacg agaatctgct gtttgcgccg     540
ggtgcgaagt ttagctatgc ctccgccaat tatgatgtgt gggcgcggt gattgaaaat     600 gtgacgggaa aaccttttac agaggtcatt gcggaacgac tcacgcagcc gctgggcatg     660
tcggcgactg tggcagttaa gggggatgag attattgtca caaggcaag cggctataaa      720 ctgggattcg gcaaacccgt tctgtttcat gcgcctctgg cccggaacca tgttcctgcc     780
gcctatatcc atagcactct gcctgatatg gaaatatgga tagacgcctg gttgcacaga     840
aaggctttgc cggcaacgct gcgtgaggcg atgagtaaca gttggcgtgg taatagtgat     900
gttccgcttg ccgcagacaa tcgtatcctc tatgccagcg gttggtttat cgaccagaat     960
caaggccctt acatcagtca cggtgggcag aatccaaact tttcttcttg cattgcgttg   1020
```

```
cgaccggatc agcagattgg cattgttgcg ctggcaaata tgaattcgaa tctgatacta  1080
cagctttgcg cggatatcga taattatctg cgcattggca aatatgctga cggcgctggt  1140
gatgcaatta cagccaccga tacccttttc gtctacctca cgttgttgct gtgttttggg  1200
ggggcggtgg ttgtagtgcg cggtgctttc cgtgtttatc gcgcaacggc gcatggccct  1260
ggaaaacagc agaggttacg tttacgcgta cgtgactata tcatcgcctt ggcggttcct  1320
gggctcgtgg ccgccatgct ctatgtcgca ccgggtatac tatctccagg acttgactgg  1380
cgttttatct tggtatgggg tccatcgagc gtgttggcga taccgttcgg aattatcctg  1440
ttagctttcg ttctgacatt aaatcatcaa attaaacgaa ttctattaca caacaaggag  1500
tgggacgatg agtaa                                                    1515
```

<210> SEQ ID NO 6
<211> LENGTH: 504
<212> TYPE: PRT
<213> ORGANISM: Artificial
<220> FEATURE:
<223> OTHER INFORMATION: ClbP K98T

<400> SEQUENCE: 6

```
Met Thr Ile Met Glu His Val Ser Ile Lys Thr Leu Tyr His Leu Leu
1               5                   10                  15

Cys Cys Met Leu Leu Phe Ile Ser Ala Met Cys Ala Leu Ala Gln Glu
            20                  25                  30

His Glu Pro Ile Gly Ala Gln Asp Glu Arg Leu Ser Thr Leu Ile His
        35                  40                  45

Gln Arg Met Gln Glu Ala Lys Val Pro Ala Leu Ser Val Ser Val Thr
    50                  55                  60

Ile Lys Gly Val Arg Gln Arg Phe Val Tyr Gly Val Ala Asp Val Ala
65                  70                  75                  80

Ser Gln Lys Ala Asn Thr Leu Asp Thr Val Tyr Glu Leu Gly Ser Met
                85                  90                  95

Ser Thr Ala Phe Thr Gly Leu Val Val Gln Ile Leu Ile Gln Glu Gly
            100                 105                 110

Arg Leu Arg Gln Gly Asp Asp Ile Ile Thr Tyr Leu Pro Glu Met Arg
        115                 120                 125

Leu Asn Tyr Gln Gly Lys Pro Ala Ser Leu Thr Val Ala Asp Phe Leu
    130                 135                 140

Tyr His Thr Ser Gly Leu Pro Phe Ser Thr Leu Ala Arg Leu Glu Asn
145                 150                 155                 160

Pro Met Pro Gly Ser Ala Val Ala Gln Gln Leu Arg Asn Glu Asn Leu
                165                 170                 175

Leu Phe Ala Pro Gly Ala Lys Phe Ser Tyr Ala Ser Ala Asn Tyr Asp
            180                 185                 190

Val Leu Gly Ala Val Ile Glu Asn Val Thr Gly Lys Thr Phe Thr Glu
        195                 200                 205

Val Ile Ala Glu Arg Leu Thr Gln Pro Leu Gly Met Ser Ala Thr Val
    210                 215                 220

Ala Val Lys Gly Asp Glu Ile Ile Val Asn Lys Ala Ser Gly Tyr Lys
225                 230                 235                 240

Leu Gly Phe Gly Lys Pro Val Leu Phe His Ala Pro Leu Ala Arg Asn
                245                 250                 255

His Val Pro Ala Ala Tyr Ile His Ser Thr Leu Pro Asp Met Glu Ile
            260                 265                 270
```

Trp Ile Asp Ala Trp Leu His Arg Lys Ala Leu Pro Ala Thr Leu Arg
            275                 280                 285

Glu Ala Met Ser Asn Ser Trp Arg Gly Asn Ser Asp Val Pro Leu Ala
    290                 295                 300

Ala Asp Asn Arg Ile Leu Tyr Ala Ser Gly Trp Phe Ile Asp Gln Asn
305                 310                 315                 320

Gln Gly Pro Tyr Ile Ser His Gly Gly Gln Asn Pro Asn Phe Ser Ser
                325                 330                 335

Cys Ile Ala Leu Arg Pro Asp Gln Gln Ile Gly Ile Val Ala Leu Ala
                340                 345                 350

Asn Met Asn Ser Asn Leu Ile Leu Gln Leu Cys Ala Asp Ile Asp Asn
            355                 360                 365

Tyr Leu Arg Ile Gly Lys Tyr Ala Asp Gly Ala Gly Asp Ala Ile Thr
    370                 375                 380

Ala Thr Asp Thr Leu Phe Val Tyr Leu Thr Leu Leu Leu Cys Phe Trp
385                 390                 395                 400

Gly Ala Val Val Val Arg Gly Ala Phe Arg Val Tyr Arg Ala Thr
                405                 410                 415

Ala His Gly Pro Gly Lys Gln Gln Arg Leu Arg Leu Arg Val Arg Asp
                420                 425                 430

Tyr Ile Ile Ala Leu Ala Val Pro Gly Leu Val Ala Ala Met Leu Tyr
    435                 440                 445

Val Ala Pro Gly Ile Leu Ser Pro Gly Leu Asp Trp Arg Phe Ile Leu
    450                 455                 460

Val Trp Gly Pro Ser Ser Val Leu Ala Ile Pro Phe Gly Ile Ile Leu
465                 470                 475                 480

Leu Ala Phe Val Leu Thr Leu Asn His Gln Ile Lys Arg Ile Leu Leu
                485                 490                 495

His Asn Lys Glu Trp Asp Asp Glu
            500

<210> SEQ ID NO 7
<211> LENGTH: 1515
<212> TYPE: DNA
<213> ORGANISM: Artificial
<220> FEATURE:
<223> OTHER INFORMATION: ClbP K98T

<400> SEQUENCE: 7

```
atgacaataa tggaacacgt tagcattaaa acattatatc atctcctgtg ctgtatgctg      60
ctctttattt ccgctatgtg cgctttggcg caagaacatg agcctatcgg ggcgcaagat     120
gagcgcctgt cgacattaat tcaccaacgg atgcaggagg ccaaggtccc agccctttcc     180
gtaagtgtga ccattaaggg ggtacgtcag cgatttgtct acggtgttgc cgatgtggct     240
agtcagaaag cgaatactct agacacagtt tacgagctgg gatcgatgag tactgcgttt     300
accggacttg tggtgcaaat actgattcag gaaggcagac tccggcaagg ggatgatatc     360
attacctatc tgccggaaat gcgcttgaat tatcagggaa aacctgcttc cctgaccgtg     420
gctgatttcc tttatcatac atcaggattg ccttttttcaa cactggctcg gctggaaaac     480
cctatgcctg ggagcgctgt ggcacagcaa ctgcgcaacg agaatctgct gtttgcgccg     540
ggtgcgaagt ttagctatgc ctccgccaat tatgatgtgt gggcgcggt gattgaaaat     600
gtgacgggaa aaccctttac agaggtcatt gcggaacgac tcacgcagcc gctgggcatg     660
tcggcgactg tggcagttaa gggggatgag attattgtca acaaggcaag cggctataaa     720
```

```
ctgggattcg gcaaacccgt tctgtttcat gcgcctctgg cccggaacca tgttcctgcc    780
gcctatatcc atagcactct gcctgatatg gaaatatgga tagacgcctg gttgcacaga    840
aaggctttgc cggcaacgct gcgtgaggcg atgagtaaca gttggcgtgg taatagtgat    900
gttccgcttg ccgcagacaa tcgtatcctc tatgccagcg gttggtttat cgaccagaat    960
caaggccctt acatcagtca cggtgggcag aatccaaact tttcttcttg cattgcgttg   1020
cgaccggatc agcagattgg cattgttgcg ctggcaaata tgaattcgaa tctgatacta   1080
cagctttgcg cggatatcga taattatctg cgcattggca aatatgctga cggcgctggt   1140
gatgcaatta cagccaccga tacccttttc gtctacctca cgttgttgct gtgttttggg   1200
ggggcggtgg ttgtagtgcg cggtgctttc cgtgtttatc gcgcaacggc gcatggccct   1260
ggaaaacagc agaggttacg tttacgcgta cgtgactata tcatcgcctt ggcggttcct   1320
gggctcgtgg ccgccatgct ctatgtcgca ccgggtatac tatctccagg acttgactgg   1380
cgttttatct tggtatgggg tccatcgagc gtgttggcga taccgttcgg aattatcctg   1440
ttagctttcg ttctgacatt aaatcatcaa attaaacgaa ttctattaca caacaaggag   1500
tgggacgatg agtaa                                                    1515
```

<210> SEQ ID NO 8
<211> LENGTH: 504
<212> TYPE: PRT
<213> ORGANISM: Artificial
<220> FEATURE:
<223> OTHER INFORMATION: ClbP S95R

<400> SEQUENCE: 8

```
Met Thr Ile Met Glu His Val Ser Ile Lys Thr Leu Tyr His Leu Leu
1               5                   10                  15

Cys Cys Met Leu Leu Phe Ile Ser Ala Met Cys Ala Leu Ala Gln Glu
            20                  25                  30

His Glu Pro Ile Gly Ala Gln Asp Glu Arg Leu Ser Thr Leu Ile His
        35                  40                  45

Gln Arg Met Gln Glu Ala Lys Val Pro Ala Leu Ser Val Ser Val Thr
    50                  55                  60

Ile Lys Gly Val Arg Gln Arg Phe Val Tyr Gly Val Ala Asp Val Ala
65                  70                  75                  80

Ser Gln Lys Ala Asn Thr Leu Asp Thr Val Tyr Glu Leu Gly Arg Met
                85                  90                  95

Ser Lys Ala Phe Thr Gly Leu Val Val Gln Ile Leu Ile Gln Glu Gly
            100                 105                 110

Arg Leu Arg Gln Gly Asp Asp Ile Ile Thr Tyr Leu Pro Glu Met Arg
        115                 120                 125

Leu Asn Tyr Gln Gly Lys Pro Ala Ser Leu Thr Val Ala Asp Phe Leu
    130                 135                 140

Tyr His Thr Ser Gly Leu Pro Phe Ser Thr Leu Ala Arg Leu Glu Asn
145                 150                 155                 160

Pro Met Pro Gly Ser Ala Val Ala Gln Gln Leu Arg Asn Glu Asn Leu
                165                 170                 175

Leu Phe Ala Pro Gly Ala Lys Phe Ser Tyr Ala Ser Ala Asn Tyr Asp
            180                 185                 190

Val Leu Gly Ala Val Ile Glu Asn Val Thr Gly Lys Thr Phe Thr Glu
        195                 200                 205

Val Ile Ala Glu Arg Leu Thr Gln Pro Leu Gly Met Ser Ala Thr Val
    210                 215                 220
```

Ala Val Lys Gly Asp Glu Ile Ile Val Asn Lys Ala Ser Gly Tyr Lys
225                 230                 235                 240

Leu Gly Phe Gly Lys Pro Val Leu Phe His Ala Pro Leu Ala Arg Asn
            245                 250                 255

His Val Pro Ala Ala Tyr Ile His Ser Thr Leu Pro Asp Met Glu Ile
        260                 265                 270

Trp Ile Asp Ala Trp Leu His Arg Lys Ala Leu Pro Ala Thr Leu Arg
    275                 280                 285

Glu Ala Met Ser Asn Ser Trp Arg Gly Asn Ser Asp Val Pro Leu Ala
290                 295                 300

Ala Asp Asn Arg Ile Leu Tyr Ala Ser Gly Trp Phe Ile Asp Gln Asn
305                 310                 315                 320

Gln Gly Pro Tyr Ile Ser His Gly Gly Gln Asn Pro Asn Phe Ser Ser
                325                 330                 335

Cys Ile Ala Leu Arg Pro Asp Gln Gln Ile Gly Ile Val Ala Leu Ala
            340                 345                 350

Asn Met Asn Ser Asn Leu Ile Leu Gln Leu Cys Ala Asp Ile Asp Asn
        355                 360                 365

Tyr Leu Arg Ile Gly Lys Tyr Ala Asp Gly Ala Gly Asp Ala Ile Thr
    370                 375                 380

Ala Thr Asp Thr Leu Phe Val Tyr Leu Thr Leu Leu Leu Cys Phe Trp
385                 390                 395                 400

Gly Ala Val Val Val Arg Gly Ala Phe Arg Val Tyr Arg Ala Thr
                405                 410                 415

Ala His Gly Pro Gly Lys Gln Gln Arg Leu Arg Leu Arg Val Arg Asp
            420                 425                 430

Tyr Ile Ile Ala Leu Ala Val Pro Gly Leu Val Ala Ala Met Leu Tyr
    435                 440                 445

Val Ala Pro Gly Ile Leu Ser Pro Gly Leu Asp Trp Arg Phe Ile Leu
450                 455                 460

Val Trp Gly Pro Ser Ser Val Leu Ala Ile Pro Phe Gly Ile Ile Leu
465                 470                 475                 480

Leu Ala Phe Val Leu Thr Leu Asn His Gln Ile Lys Arg Ile Leu Leu
                485                 490                 495

His Asn Lys Glu Trp Asp Asp Glu
            500

<210> SEQ ID NO 9
<211> LENGTH: 1515
<212> TYPE: DNA
<213> ORGANISM: Artificial
<220> FEATURE:
<223> OTHER INFORMATION: ClbP S95R

<400> SEQUENCE: 9
atgacaataa tggaacacgt tagcattaaa acattatatc atctcctgtg ctgtatgctg      60
ctctttattt ccgctatgtg cgctttggcg caagaacatg agcctatcgg ggcgcaagat     120
gagcgcctgt cgacattaat tcaccaacgg atgcaggagg ccaaggtccc agccctttcc     180
gtaagtgtga ccattaaggg ggtacgtcag cgatttgtct acggtgttgc cgatgtggct     240
agtcagaaag cgaatactct agacacagtt tacgagctgg gacggatgag taaggcgttt     300
accggacttg tggtgcaaat actgattcag gaaggcagac tccggcaagg ggatgatatc     360
attacctatc tgccggaaat gcgcttgaat tatcaggaa aacctgcttc cctgaccgtg      420

```
gctgatttcc tttatcatac atcaggattg ccttttttcaa cactggctcg gctggaaaac    480
cctatgcctg ggagcgctgt ggcacagcaa ctgcgcaacg agaatctgct gtttgcgccg    540
ggtgcgaagt ttagctatgc ctccgccaat tatgatgtgt gggcgcggt gattgaaaat    600
gtgacgggaa aaacctttac agaggtcatt gcggaacgac tcacgcagcc gctgggcatg    660
tcggcgactg tggcagttaa ggggatgag attattgtca acaaggcaag cggctataaa    720
ctgggattcg gcaaacccgt tctgtttcat gcgcctctgg cccggaacca tgttcctgcc    780
gcctatatcc atagcactct gcctgatatg gaaatatgga tagacgcctg gttgcacaga    840
aaggctttgc cggcaacgct gcgtgaggcg atgagtaaca gttggcgtgg taatagtgat    900
gttccgcttg ccgcagacaa tcgtatcctc tatgccagcg gttggtttat cgaccagaat    960
caaggcccct acatcagtca cggtgggcag aatccaaact tttcttcttg cattgcgttg   1020
cgaccggatc agcagattgg cattgttgcg ctggcaaata tgaattcgaa tctgatacta   1080
cagctttgcg cggatatcga taattatctg cgcattggca atatgctga cggcgctggt   1140
gatgcaatta cagccaccga taccctttttc gtctacctca cgttgttgct gtgttttttgg   1200
ggggcggtgg ttgtagtgcg cggtgctttc cgtgtttatc gcgcaacggc catggccct    1260
ggaaaacagc agaggttacg tttacgcgta cgtgactata tcatcgcctt ggcggttcct   1320
gggctcgtgg ccgccatgct ctatgtcgca ccgggtatac tatctccagg acttgactgg   1380
cgttttatct tggtatgggg tccatcgagc gtgttggcga taccgttcgg aattatcctg   1440
ttagctttcg ttctgacatt aaatcatcaa attaaacgaa ttctattaca caacaaggag   1500
tgggacgatg agtaa                                                    1515
```

<210> SEQ ID NO 10
<211> LENGTH: 504
<212> TYPE: PRT
<213> ORGANISM: Artificial
<220> FEATURE:
<223> OTHER INFORMATION: ClbP Y186G

<400> SEQUENCE: 10

Met Thr Ile Met Glu His Val Ser Ile Lys Thr Leu Tyr His Leu Leu
1               5                   10                  15

Cys Cys Met Leu Leu Phe Ile Ser Ala Met Cys Ala Leu Ala Gln Glu
            20                  25                  30

His Glu Pro Ile Gly Ala Gln Asp Glu Arg Leu Ser Thr Leu Ile His
        35                  40                  45

Gln Arg Met Gln Glu Ala Lys Val Pro Ala Leu Ser Val Ser Val Thr
    50                  55                  60

Ile Lys Gly Val Arg Gln Arg Phe Val Tyr Gly Val Ala Asp Val Ala
65                  70                  75                  80

Ser Gln Lys Ala Asn Thr Leu Asp Thr Val Tyr Glu Leu Gly Ser Met
                85                  90                  95

Ser Lys Ala Phe Thr Gly Leu Val Val Gln Ile Leu Ile Gln Glu Gly
            100                 105                 110

Arg Leu Arg Gln Gly Asp Asp Ile Ile Thr Tyr Leu Pro Glu Met Arg
        115                 120                 125

Leu Asn Tyr Gln Gly Lys Pro Ala Ser Leu Thr Val Ala Asp Phe Leu
    130                 135                 140

Tyr His Thr Ser Gly Leu Pro Phe Ser Thr Leu Ala Arg Leu Glu Asn
145                 150                 155                 160

Pro Met Pro Gly Ser Ala Val Ala Gln Gln Leu Arg Asn Glu Asn Leu

```
                    165                 170                 175

Leu Phe Ala Pro Gly Ala Lys Phe Ser Gly Ala Ser Ala Asn Tyr Asp
            180                 185                 190

Val Leu Gly Ala Val Ile Glu Asn Val Thr Gly Lys Thr Phe Thr Glu
        195                 200                 205

Val Ile Ala Glu Arg Leu Thr Gln Pro Leu Gly Met Ser Ala Thr Val
    210                 215                 220

Ala Val Lys Gly Asp Glu Ile Val Asn Lys Ala Ser Gly Tyr Lys
225                 230                 235                 240

Leu Gly Phe Gly Lys Pro Val Leu Phe His Ala Pro Leu Ala Arg Asn
                245                 250                 255

His Val Pro Ala Ala Tyr Ile His Ser Thr Leu Pro Asp Met Glu Ile
            260                 265                 270

Trp Ile Asp Ala Trp Leu His Arg Lys Ala Leu Pro Ala Thr Leu Arg
        275                 280                 285

Glu Ala Met Ser Asn Ser Trp Arg Gly Asn Ser Asp Val Pro Leu Ala
    290                 295                 300

Ala Asp Asn Arg Ile Leu Tyr Ala Ser Gly Trp Phe Ile Asp Gln Asn
305                 310                 315                 320

Gln Gly Pro Tyr Ile Ser His Gly Gly Gln Asn Pro Asn Phe Ser Ser
                325                 330                 335

Cys Ile Ala Leu Arg Pro Asp Gln Gln Ile Gly Ile Val Ala Leu Ala
            340                 345                 350

Asn Met Asn Ser Asn Leu Ile Leu Gln Leu Cys Ala Asp Ile Asp Asn
        355                 360                 365

Tyr Leu Arg Ile Gly Lys Tyr Ala Asp Gly Ala Gly Asp Ala Ile Thr
    370                 375                 380

Ala Thr Asp Thr Leu Phe Val Tyr Leu Thr Leu Leu Cys Phe Trp
385                 390                 395                 400

Gly Ala Val Val Val Arg Gly Ala Phe Arg Val Tyr Arg Ala Thr
                405                 410                 415

Ala His Gly Pro Gly Lys Gln Gln Arg Leu Arg Leu Arg Val Arg Asp
            420                 425                 430

Tyr Ile Ile Ala Leu Ala Val Pro Gly Leu Val Ala Ala Met Leu Tyr
        435                 440                 445

Val Ala Pro Gly Ile Leu Ser Pro Gly Leu Asp Trp Arg Phe Ile Leu
    450                 455                 460

Val Trp Gly Pro Ser Ser Val Leu Ala Ile Pro Phe Gly Ile Ile Leu
465                 470                 475                 480

Leu Ala Phe Val Leu Thr Leu Asn His Gln Ile Lys Arg Ile Leu Leu
                485                 490                 495

His Asn Lys Glu Trp Asp Asp Glu
            500

<210> SEQ ID NO 11
<211> LENGTH: 651
<212> TYPE: PRT
<213> ORGANISM: Artificial
<220> FEATURE:
<223> OTHER INFORMATION: ClbP-3H

<400> SEQUENCE: 11

Met Thr Ile Met Glu His Val Ser Ile Lys Thr Leu Tyr His Leu Leu
1               5                   10                  15

Cys Cys Met Leu Leu Phe Ile Ser Ala Met Cys Ala Leu Ala Gln Glu
```

```
            20                  25                  30
His Glu Pro Ile Gly Ala Met Pro Val Leu Glu Asn Arg Ala Ala Gln
        35                  40                  45

Gly Asp Ile Thr Ala Pro Gly Ala Arg Arg Leu Thr Gly Asp Gln
    50                  55                  60

Thr Ala Ala Leu Arg Asp Ser Leu Ser Asp Lys Pro Ala Lys Asn Ile
65                  70                  75                  80

Ile Leu Leu Ile Gly Asp Gly Met Gly Asp Ser Glu Ile Thr Ala Ala
                85                  90                  95

Arg Asn Tyr Ala Glu Gly Ala Gly Gly Phe Phe Lys Gly Ile Asp Ala
            100                 105                 110

Leu Pro Leu Thr Gly Gln Tyr Thr His Tyr Ala Leu Asn Lys Lys Thr
        115                 120                 125

Gly Lys Pro Asp Tyr Val Thr Asp Ser Ala Ala Ser Ala Thr Ala Trp
    130                 135                 140

Ser Thr Gly Val Lys Thr Tyr Asn Gly Ala Leu Gly Val Asp Ile His
145                 150                 155                 160

Glu Lys Asp His Pro Thr Ile Leu Glu Met Ala Lys Ala Ala Gly Leu
                165                 170                 175

Ala Thr Gly Asn Val Ser Thr Ala Glu Leu Gln Asp Ala Thr Pro Ala
            180                 185                 190

Ala Leu Val Ala His Val Thr Ser Arg Lys Cys Tyr Gly Pro Ser Ala
        195                 200                 205

Thr Ser Glu Lys Cys Pro Gly Asn Ala Leu Glu Lys Gly Gly Lys Gly
    210                 215                 220

Ser Ile Thr Glu Gln Leu Leu Asn Ala Arg Ala Asp Val Thr Leu Gly
225                 230                 235                 240

Gly Gly Ala Lys Thr Phe Ala Glu Thr Ala Thr Ala Gly Glu Trp Gln
                245                 250                 255

Gly Lys Thr Leu Arg Glu Gln Ala Gln Ala Arg Gly Tyr Gln Leu Val
            260                 265                 270

Ser Asp Ala Ala Ser Leu Asn Ser Val Thr Glu Ala Asn Gln Gln Lys
        275                 280                 285

Pro Leu Leu Gly Leu Phe Ala Asp Gly Asn Met Pro Val Arg Trp Leu
    290                 295                 300

Gly Pro Lys Ala Thr Tyr His Gly Asn Ile Asp Lys Pro Ala Val Thr
305                 310                 315                 320

Cys Thr Pro Asn Pro Gln Arg Asn Asp Ser Val Pro Thr Leu Ala Gln
                325                 330                 335

Met Thr Asp Lys Ala Ile Glu Leu Leu Ser Lys Asn Glu Lys Gly Phe
            340                 345                 350

Phe Leu Gln Val Glu Gly Ala Ser Ile Asp Lys Gln Asp His Ala Ala
        355                 360                 365

Asn Pro Cys Gly Gln Ile Gly Glu Thr Val Asp Leu Asp Glu Ala Val
    370                 375                 380

Gln Arg Ala Leu Glu Phe Ala Lys Lys Glu Gly Asn Thr Leu Val Ile
385                 390                 395                 400

Val Thr Ala Asp His Ala His Ala Ser Gln Ile Val Ala Pro Asp Thr
                405                 410                 415

Lys Ala Pro Gly Leu Thr Gln Ala Leu Asn Thr Lys Asp Gly Ala Val
            420                 425                 430

Met Val Met Ser Tyr Gly Asn Ser Glu Glu Asp Ser Gln Glu His Thr
        435                 440                 445
```

Gly Ser Gln Leu Arg Ile Ala Ala Tyr Gly Pro His Ala Ala Asn Val
          450                 455                 460

Val Gly Leu Thr Asp Gln Thr Asp Leu Phe Tyr Thr Met Lys Ala Ala
465                 470                 475                 480

Leu Gly Leu Lys Ile Ala Leu Arg Pro Asp Gln Gln Ile Gly Ile Val
              485                 490                 495

Ala Leu Ala Asn Met Asn Ser Asn Leu Ile Leu Gln Leu Cys Ala Asp
          500                 505                 510

Ile Asp Asn Tyr Leu Arg Ile Gly Lys Tyr Ala Asp Gly Ala Gly Asp
          515                 520                 525

Ala Ile Thr Ala Thr Asp Thr Leu Phe Val Tyr Leu Thr Leu Leu Leu
          530                 535                 540

Cys Phe Trp Gly Ala Val Val Val Arg Gly Ala Phe Arg Val Tyr
545                 550                 555                 560

Arg Ala Thr Ala His Gly Pro Gly Lys Gln Gln Arg Leu Arg Leu Arg
              565                 570                 575

Val Arg Asp Tyr Ile Ile Ala Leu Ala Val Pro Gly Leu Val Ala Ala
              580                 585                 590

Met Leu Tyr Val Ala Pro Gly Ile Leu Ser Pro Gly Leu Asp Trp Arg
          595                 600                 605

Phe Ile Leu Val Trp Gly Pro Ser Ser Val Leu Ala Ile Pro Phe Gly
610                 615                 620

Ile Ile Leu Leu Ala Phe Val Leu Thr Leu Asn His Gln Ile Lys Arg
625                 630                 635                 640

Ile Leu Leu His Asn Lys Glu Trp Asp Asp Glu
              645                 650

<210> SEQ ID NO 12
<211> LENGTH: 1338
<212> TYPE: DNA
<213> ORGANISM: Artificial
<220> FEATURE:
<223> OTHER INFORMATION: ClbP-3H

<400> SEQUENCE: 12

```
atgcctgttc tggaaaaccg ggctgctcag ggcgatatta ctgcaccegg cggtgctcgc      60
cgtttaacgg gtgatcagac tgccgctctg cgtgattctc ttagcgataa acctgcaaaa     120
aatattattt tgctgattgg cgatgggatg ggggactcgg aaattactgc cgcacgtaat     180
tatgccgaag gtgcgggcgg cttttttaaa ggtatagatg ccttaccgct taccgggcaa     240
tacactcact atgcgctgaa taaaaaaacc ggcaaaccgg actacgtcac cgactcggct     300
gcatcagcaa ccgcctggtc aaccggtgtc aaaaccctata cggcgcgct gggcgtcgat     360
attcacgaaa aagatcaccc aacgattctg gaaatggcaa agccgcagg tctggcgacc     420
ggtaacgttt ctaccgcaga gttgcaggat gccacgcccg ctgcgctggt ggcacatgtg     480
acctcgcgca atgctacgg tccgagcgcg accagtgaaa atgtcccggg taacgctctg     540
gaaaaaggcg aaaaggatc gattaccgaa cagctgctta cgctcgtgc gacgttacg      600
cttggcggcg gcgcaaaaac ctttgctgaa acggcaaccg ctggtgaatg cagggaaaa     660
acgctgcgtg aacaggcaca ggcgcgtggt tatcagttgg tgagcgatgc tgcctcactg     720
aattcggtga cggaagcgaa tcagcaaaaa cccctgcttg gcctgtttgc tgacggcaat     780
atgccagtgc gctggctagg accgaaagca acgtaccatg caatatcga taagcccgca     840
gtcacctgta cgccaaatcc gcaacgtaat gacagtgtac caaccctggc gcagatgacc     900
```

-continued

```
gacaaagcca ttgaattgtt gagtaaaaat gagaaaggct ttttcctgca agttgaaggt      960
gcgtcaatcg ataaacagga tcatgctgcg aatccttgtg ggcaaattgg cgagacggtc     1020
gatctcgatg aagccgtaca acgggcgctg gaattcgcta aaaaggaggg taacacgctg     1080
gtcatagtca ccgctgatca cgcccacgcc agccagattg ttgcgccgga taccaaagct     1140
ccgggcctca cccaggcgct aaataccaaa gatggcgcag tgatggtgat gagttacggg     1200
aactccgaag aggattcaca agaacatacc ggcagtcagt tgcgtattgc ggcgtatggc     1260
ccgcatgccg ccaatgttgt tggactgacc gaccagaccg atctcttcta caccatgaaa     1320
gccgctctgg ggctgaaa                                                   1338
```